US010519205B2

(12) United States Patent
Spudich et al.

(10) Patent No.: US 10,519,205 B2
(45) Date of Patent: Dec. 31, 2019

(54) COMPOSITIONS AND METHODS FOR USE OF ANION CHANNEL RHODOPSINS

(71) Applicant: BOARD OF REGENTS OF THE UNIVERSITY OF TEXAS SYSTEM, Austin, TX (US)

(72) Inventors: John Lee Spudich, Houston, TX (US); Elena G. Govorunova, Houston, TX (US); Oleg A. Sineshchekov, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 7 days.

(21) Appl. No.: 15/559,512

(22) PCT Filed: Mar. 18, 2016

(86) PCT No.: PCT/US2016/023095
§ 371 (c)(1),
(2) Date: Sep. 19, 2017

(87) PCT Pub. No.: WO2016/149599
PCT Pub. Date: Sep. 22, 2016

(65) Prior Publication Data
US 2018/0118793 A1 May 3, 2018

Related U.S. Application Data

(60) Provisional application No. 62/135,470, filed on Mar. 19, 2015, provisional application No. 62/149,812, filed on Apr. 20, 2015, provisional application No. 62/261,821, filed on Dec. 1, 2015.

(51) Int. Cl.
| | | |
|---|---|---|
| A01N 63/00 | (2006.01) |
| C12N 15/63 | (2006.01) |
| C07H 21/04 | (2006.01) |
| C07K 14/405 | (2006.01) |
| A61P 27/02 | (2006.01) |
| A61K 48/00 | (2006.01) |
| C12N 15/79 | (2006.01) |
| C12N 15/74 | (2006.01) |
| C12N 15/82 | (2006.01) |
| A61N 5/06 | (2006.01) |
| A61K 38/00 | (2006.01) |

(52) U.S. Cl.
CPC ........ *C07K 14/405* (2013.01); *A61K 48/0058* (2013.01); *A61P 27/02* (2018.01); *A61K 38/00* (2013.01); *A61N 5/062* (2013.01); *C07H 21/04* (2013.01); *C12N 15/74* (2013.01); *C12N 15/79* (2013.01); *C12N 15/82* (2013.01); *C12N 2510/00* (2013.01)

(58) Field of Classification Search
CPC ........ C12N 15/74; C12N 15/79; C12N 15/82; C12N 2510/00; C07H 21/04

USPC .......... 424/93.2, 93.21; 435/320.1; 536/23.1, 536/23.7, 24.1
See application file for complete search history.

(56) References Cited

U.S. PATENT DOCUMENTS

2012/0190629 A1   7/2012   Tomita et al.
2012/0214188 A1   8/2012   Klapoetke et al.

FOREIGN PATENT DOCUMENTS

WO   WO 2016/149599   9/1916

OTHER PUBLICATIONS

Kotterman et al., 2014, Nature Reviews, vol. 15, p. 445-451.*
Kaur et al., 2009, Current Gene Therapy, vol. 9. p. 434-458.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Klapoetke et al., 2014, GenEMBL Accession No. KF992074, computer printout pp. 6-7, submitted Dec. 19, 2013.*
Extended European Search Report and Opinion issued in corresponding European Application No. 16765813.7, dated Oct. 8, 2018.
Klapoetke, Nathan C., et al. "Independent Optical Excitation of Distinct Neural Populations." *Nature Methods* 11.3 (2014): 338.
Uniprot Accession No. L1IFZ3, Uncharacterized Protein (online), <http://www.uniprot.org/uniprot/ L1IFZ3>, dated Mar. 6, 2013.
Berndt et al., "Structural foundations of optogenetics: Determinants of channelrhodopsin ion selectivity," *Proc. Natl. Acad. Sci. USA*, 113:822-829, 2015.
Berndt et al., "Structure-guided transformation of channelrhodopsin into a light-activated chloride channel," *Science*, 344(6182):420-424, 2014.
GenBank Accession KF992074. Synthetic cinstruct PsChR1 gene (online), <http://www.ncbi.nlm.nih.gov/nuccore/KF992074>, 2014.
GenBank Accession No. KP171708.1. Synthetic construct ACR1 gene, partial cds. (online), <http://www.ncbi.nlm.nih.gov/nuccore/KP171708>, 2015.
GenBank Accession No. KX879687.1. Synthetic construct clone R1ACR_741 anion channel rhodopsin gene, partial cds. (online), <http://www.ncbi.nlm.nih.gov/nuccore/KX879687.1>, 2017.
Govorunova et al., "Anion channelrhodopsins for inhibitory cardiac optogenetics," *Sci. Rep.*, 6;33530, 2016.
Govorunova et al., "Natural light-gated anion channels: A family of microbial rhodopsins for advanced optogenetics," *Science*, 349(6248):647-650, 2015.

(Continued)

*Primary Examiner* — Shin Lin Chen
(74) *Attorney, Agent, or Firm* — Parker Highlander PLLC

(57) ABSTRACT

Methods and compositions used to identify and characterize a new class of rhodopsins derived from algae, which are highly sensitive and efficient anion-conducting channelrhodopsins. The rhodopsin domain of these anion-conducting channelrhodopsins have been cloned and expressed in mammalian systems and thus may be used in, among others, optogenetic applications and as therapeutic agents for electrically active cell mediated disorders.

12 Claims, 21 Drawing Sheets

Specification includes a Sequence Listing.

(56) References Cited

OTHER PUBLICATIONS

Govorunova et al., "New channelrhodopsin with a red-shifted spectrum and rapid kinetics from Mesostigma viride," *mBio 2*, e00115-00111, 2011.

Govorunova et al., "Proteomonas sulcata ACR1: A fast anion channelrhodopsin," *Photochem. Photobiol.* 92:257-263, 2016.

International Preliminary Report on Patentability issued in corresponding PCT Application No. PCT/US2016/023095, dated Sep. 19, 2017.

International Search Report and Written Opinion issued in corresponding PCT Application No. PCT/US2016/023095, dated Aug. 22, 2016.

Mardinly et al., "Precise multimodal optical control of neural ensemble activity," *Nat. Neurosci.*, 2018.

Sineshchekov et al., "Gating mechanisms of a natural anion channelrhodopsin," *Proc. Natl. Acad. Sci. USA*, 112:14236-14241, 2015.

Uniprot Accession No. L1J207. Uncharacterized Protein (online), <http://www.uniprot.org/uniprot/L1J207>, 2013.

Wietek et al., "An improved chloride-conducting channelrhodopsin for light-induced inhibition of neuronal activity in vivo," *Sci. Rep.* 5:14807, 2015.

Wietek et al., "Conversion of Channelrhodopsin into a Light-Gated Chloride Channel," *Science*, 344, 409 (2014).

* cited by examiner

```
                  helix 2
GtACR1     WEAIYLPTTE----MITYSL  74   SEQ ID NO: 32
GtACR2     WESVYLPFVE----SITYAL  70   SEQ ID NO: 33
Gt161302   WEFVLVPLTE----CFVYGL  67   SEQ ID NO: 34
CrChR1     WEEIYVATIEMIKFIIEYFH 139   SEQ ID NO: 35
CrChR2     WEEIYVCAIEMVKVILEFFF 100   SEQ ID NO: 36
CaChR1     WEEVYVCCIELVFICFELYH 146   SEQ ID NO: 37
MvChR1     WEVWFVACIETSIYITAITS 119   SEQ ID NO: 38
HsHR       RPRLIWGATLMIPLVSISSY  77   SEQ ID NO: 39
NmHR       ALSCIVMVSAGLILNSQAVM  71   SEQ ID NO: 40
```

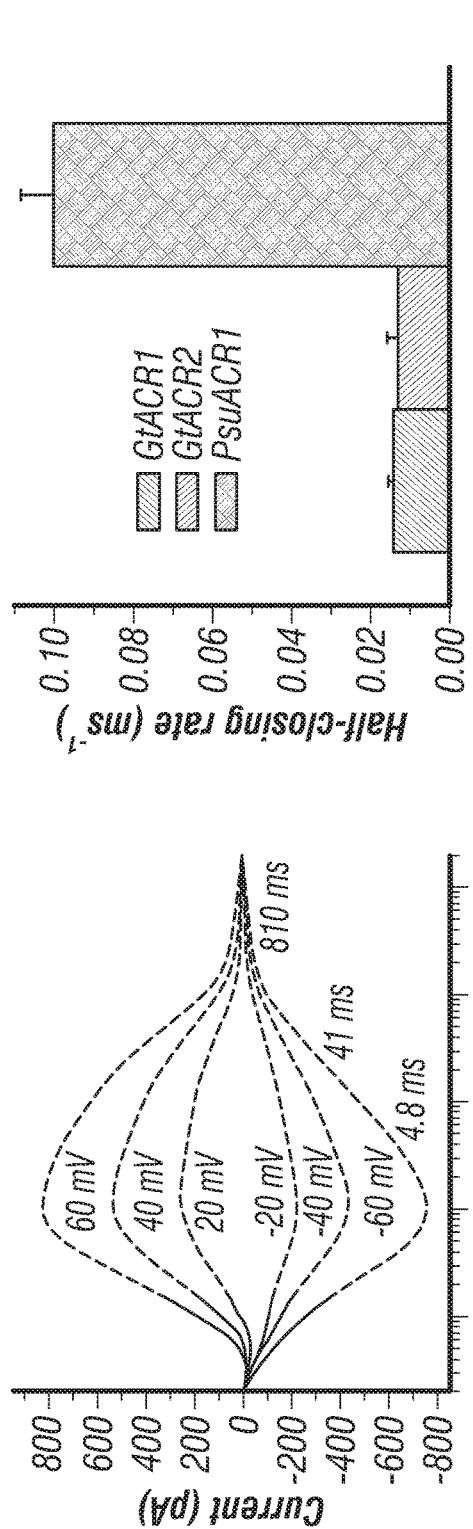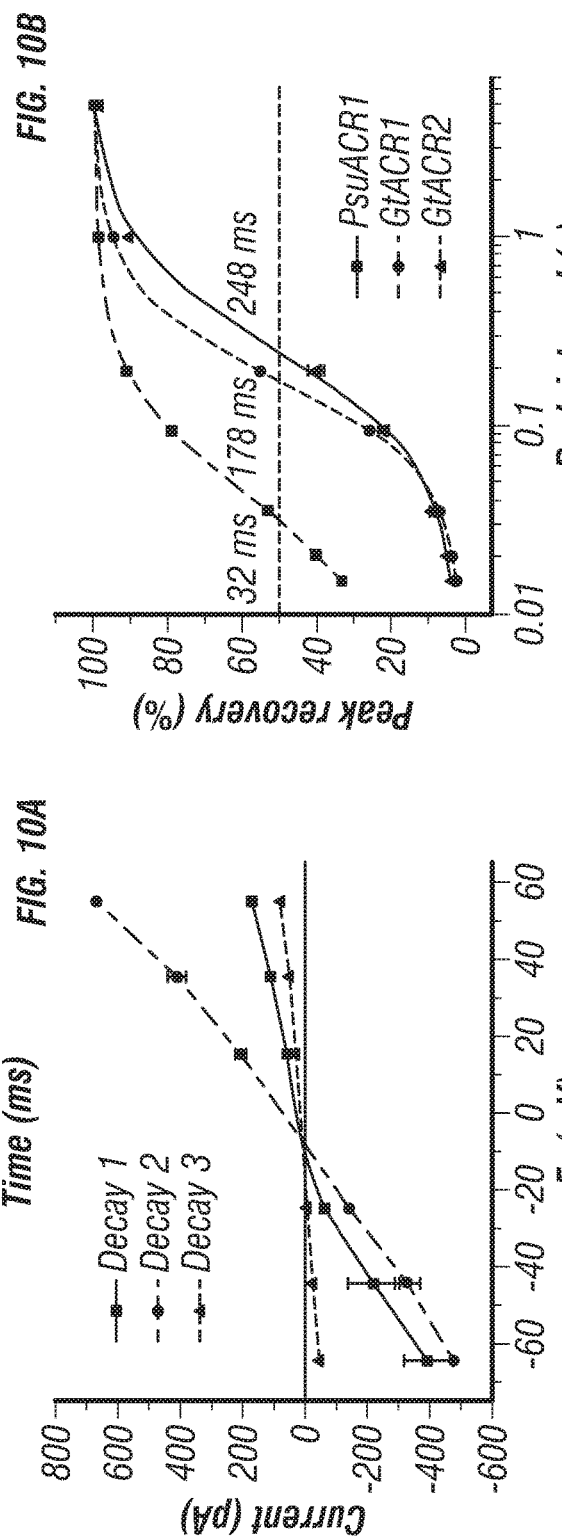

FIG. 12

COMPOSITIONS AND METHODS FOR USE OF ANION CHANNEL RHODOPSINS

This application is a national phase application under 35 U.S.C. § 371 of International Application No. PCT/US2016/023095, filed Mar. 18, 2016, which claims benefit of priority to U.S. Provisional Application Ser. No. 62/135,470, filed Mar. 19, 2015, No. 62/149,812, filed Apr. 20, 2015, and No. 62/261,821, filed Dec. 1, 2015, the entire contents of which are hereby incorporated by reference.

This invention was made with U.S. Government support under Grant Nos. MH098288 and GM027750, awarded by the National Institutes of Health. The government has certain rights in the invention.

BACKGROUND OF THE INVENTION

1. Field of the Invention

This disclosure generally relates to methods and compositions that utilize channelrhodopsins derived from algae, and more particularly to anion-conducting channelrhodopsins which have novel characteristics, for optogenetic applications or for use as therapeutic agents.

2. Description of Related Art

Optogenetics (Deisseroth. *Nat Methods* 8 (1): 26-9, 2011), refers to using optical methods for probing and controlling genetically targeted neurons within intact neural circuits. Optogenetics involves the introduction of light-activated channels and enzymes that allow manipulation of neural activity with millisecond precision while maintaining cell-type resolution through the use of specific targeting mechanisms. Because the brain is a high-speed system, millisecond-scale temporal precision is central to the concept of optogenetics, which allows probing the causal role of specific action potential patterns in defined cells.

Light control of motility behavior (phototaxis and photophobic responses) in green flagellate algae is mediated by sensory rhodopsins homologous to phototaxis receptors and light-driven ion transporters in prokaryotic organisms. In the phototaxis process, excitation of the algal sensory rhodopsins leads to generation of transmembrane photoreceptor currents. When expressed in animal cells, the algal phototaxis receptors function as light-gated cation channels, which has earned them the name "channelrhodopsins". Channelrhodopsins have become useful molecular tools for light control of cellular activity.

Originally, the source of these light-activated channels and enzymes were several microbial opsins, including Channelrhodopsin-2 (ChR2) a single-component light-activated cation channel from algae, which allowed millisecond-scale temporal control in mammals, required only one gene to be expressed in order to work, and responded to visible-spectrum light with a chromophore (retinal) that was already present and supplied to ChR2 by the mammalian brain tissue. The experimental utility of ChR2 was quickly proven in a variety of animal models ranging from behaving mammals to classical model organisms such as flies, worms, and zebrafish, and hundreds of groups have employed ChR2 and related microbial proteins to study neural circuits. Currently, several members of this family have been recruited as molecular tools for optogenetics, i.e. regulation of cellular activity with light. Phototaxis receptors from green (chlorophyte) flagellate algae (6), best known as channelrhodopsins (ChRs) owing to their function as light-gated cation channels are widely used to depolarize genetically targeted populations of excitable cells.

Hyperpolarizing rhodopsin ion pumps have been employed to suppress neuron firing, but they transport only a single charge per captured photon and therefore have limited capacity. Recently, ChRs were engineered to conduct Cl−, but these optogenetic tools still retain some cation conductance and could be made highly light-sensitive only at the expense of greatly slowing the channel kinetics with additional mutations (J. Wietek et al., Science 344, 409 (2014) and A. Berndt, S. Y. Lee, C. Ramakrishnan, K. Deisseroth, Science 344, 420 (2014)). Ideal for optogenetic hyperpolarization would be natural light-gated anion channels optimized by evolution to be highly conductive and anion-selective.

Described herein are modified and optimized rhodopsin domains derived from a newly identified class of channelrhodopsins, Anion Channel Rhodopsins (ACRs), light-gated anion channels that provide highly sensitive and efficient membrane hyperpolarization and neuronal silencing through light-gated chloride conduction.

SUMMARY OF THE INVENTION

The presently disclosed methods and compositions are based, in part, on the discovery and identification of a novel class of channelrhodopsins, Anion Channel Rhodopsins (ACRs). Light-gated rhodopsin cation channels from chlorophyte algae have transformed neuroscience research through their use as membrane-depolarizing optogenetic tools for targeted photoactivation of neuron firing. Photo-suppression of neuronal action potentials has been limited by the lack of equally efficient tools for membrane hyperpolarization. Described herein are Anion Channel Rhodopsins (ACRs), a new family of light-gated anion channels that provide highly sensitive and efficient membrane hyperpolarization and neuronal silencing through light-gated chloride conduction. ACRs strictly conduct anions, completely excluding protons and larger cations, and hyperpolarize the membrane with 100-fold faster kinetics at 3000-fold lower light intensity than the most efficient currently available optogenetic proteins. Sequences encoding 7TM domains of *G. theta* opsins (295, 291 and 288 aa, corresponding to the JGI protein models 111593, 146828 and 161302, respectively) were optimized for human codon usage and were synthesized. The sequence information encoding the functional constructs 111593 (GtACR1: SEQ ID NO 1) and 146828 (GtACR2: SEQ ID NO: 3) will be represented in GenBank (accession numbers KP171708 and KP171709, respectively). Illumination of neurons expressing GtACR2 fully inhibited their action potential spikes. These ACRs provide new membrane-hyperpolarizing tools for use in establishing a high level of membrane potential for use as optogenetic tools for neuronal silencing of excited cells for among others, neuronal or neurologic disorders, such as but not limited to Parkinson's disease and epilepsy, as well as for cardiac disorders. Thus, ACRs provided herein can serve as new membrane-hyperpolarizing tools for use treatment of epilepsy, as well as for cardiac disorders.

In some embodiments herein is disclosed a recombinant nucleic acid operatively linked to a heterologous promoter sequence, said recombinant nucleic acid comprising: a sequence that encodes a peptide with at least 90%, 91%, 92%, 93%, 94%, 95%, 96%, 97%, 98% or 99% identical to a sequence selected from the group consisting of SEQ ID NO: 1, SEQ ID NO: 3 or SEQ ID NO: 13; or a sequence that encodes a peptide comprising 225 contiguous amino acids selected from SEQ ID NO: 1, SEQ ID NO: 3, or SEQ ID NO: 13; or a sequence that hybridizes to the nucleotide sequence of SEQ ID NO:2, SEQ ID NO: 4, SEQ ID NOs: 14-15 or the complement thereof. In another embodiment the recombinant nucleic acid comprises an expression vector. In another embodiment of the recombinant nucleic acid the sequence that hybridized to the nucleotide sequence of SEQ ID NO:2, SEQ ID NO: 4, SEQ ID NOs: 14-15 or the complement thereof, further comprises hybridization to filter-bound DNA in 0.5 M NaHPO4, 7% sodium dodecyl sulfate, 1 mM EDTA at 65° C., and washing in 0.2×SSC/0.1% SDS at 42° C. In a further embodiment a recombinant host cell comprising a recombinant nucleic acid operatively linked to a heterologous promoter sequence, said recombinant nucleic acid comprising: a sequence that encodes a peptide with at least 70% homology to an amino acid sequence selected from SEQ ID NO: 1, SEQ ID NO: 3 or SEQ ID NO: 13; or a sequence that encodes a peptide comprising 225 contiguous amino acids selected from SEQ ID NO: 1, SEQ ID NO: 3 or SEQ ID NO: 13; or a sequence that hybridizes to the nucleotide sequence of SEQ ID NO:2, SEQ ID NO: 4, SEQ ID NOs:14-15 or the complement thereof is disclosed.

In further embodiments, ACRs can be used as membrane-depolarizing tools, with or without induction of action potentials, in compartments of neurons or cardiomyocytes. Thus, in some aspects, ACR coding sequences of the embodiments further comprise a signal sequence that targets the encoding mRNA or polypeptide a compartment of a host cell.

In some embodiments a host cell is an: isolated human cell; a non-human mammalian cell; a bacterial cell; a yeast cell; an insect cell; or a plant cell.

In alternative embodiments, the nucleic acid sequences described can be targeted to the genome of a cell using a CRISPR-associated protein-9 nuclease (Cas9) based system for genome-editing and genome targeting. In some embodiments, delivery to some cells may require delivery systems, such as, but not limited to those based on lentivirus (LVs), adenovirus (AdV) and adenoassociated (AAV).

In some embodiments a method of restoring photosensitivity to a retina of a subject suffering from vision loss or blindness is disclosed, said method comprising: delivering to the OFF-bipolar neurons of the retina of said subject an expression vector comprising a polynucleotide that encodes an amino acid sequence at least about 90%, 91%, 92%, 93%, 94%, 95%, 96%, 97%, 98% or 99% identical to a sequence selected from the group consisting of SEQ ID NO: 1, SEQ ID NO: 3 or SEQ ID NO: 13 which encodes a rhodopsin domain of an ACR expressible in a retinal neuron; and expressing said vector in said retinal neuron, wherein the expressed rhodopsin renders said retinal neuron photosensitive, thereby restoring photosensitivity to enable light-induced silencing of such neuron in said retina or a portion thereof. In a further embodiment the subject is mammalian, and in a still further embodiment the subject is human. In an embodiment of the method of restoring photosensitivity to a retina of a subject suffering from vision loss or blindness is disclosed, said method comprising: delivering to the retina of said subject an expression vector wherein the delivering comprises a pharmaceutically acceptable carrying agent.

In some further embodiments, there is provided an isolated nucleic acid molecule comprising a sequence encoding an anion-conducting channelrhodopsin having a sequence at least about 90%, 91%, 92%, 93%, 94%, 95%, 96%, 97%, 98% or 99% identical to a sequence according to SEQ ID NOs: 15-24. In certain aspects, the isolated nucleic acid molecule comprises a sequence that hybridized to the nucleotide sequence of one of SEQ ID NOs: 15-24 under stringent conditions comprising hybridization to filter-bound DNA in 0.5 M NaHPO4, 7% sodium dodecyl sulfate, 1 mM EDTA at 65° C., and washing in 0.2×SSC/0.1% SDS at 42° C. and encodes an anion-conducting channelrhodopsin. In some aspects, the nucleic acid is a DNA. In other aspects, the nucleic acid is a RNA (e.g., mRNA). In further embodiments, there is provided an expression vector comprising a nucleic acid molecule provided herein, such as a sequence at least about 90% identical to a sequence according to SEQ ID NOs: 15-24.

In even further embodiment, there is provided a recombinant host cell comprising a nucleic acid provided herein (e.g., a sequence at least about 90% identical to a sequence according to SEQ ID NOs: 15-24). In some aspects, the host cell is an isolated human cell. In other aspects, the host cell is a non-human mammalian cell. In some aspects, the host cell is a bacterial cell. In certain aspects, the host cell is a yeast cell. In other aspects, the host cell is an insect cell. In some aspects, the host cell is a plant cell. In certain aspects, host cell is an isolated neuronal cell. In particular, the host cell is an isolated electrically active cell.

In another embodiment, there is provided a method of treating a subject suffering from a disorder that involves electrically active cells comprising expressing in the subject an effective amount of an anion-conducting channelrhodopsin at the site of the electrically active cells. In some aspects, the subject is suffering from neuropathic pain the method comprising expressing in the subject an effective amount of an anion-conducting channelrhodopsin at the site of the pain. In certain aspects, the subject has an amputated limb, diabetes, multiple sclerosis or has undergone a surgery.

In certain aspects, expressing comprises administering an anion-conducting channelrhodopsin to the subject. In some aspects, the anion-conducting channelrhodopsin comprises an amino acid sequence at least about 90%, 91%, 92%, 93%, 94%, 95%, 96%, 97%, 98% or 99% identical to a sequence of SEQ ID NOs: 1, 3 or 13. In certain aspects, the anion-conducting channelrhodopsin is encoded by a sequence at about 90%, 91%, 92%, 93%, 94%, 95%, 96%, 97%, 98% or 99% identical to sequence according to SEQ ID NOs: 2, 4 or 14-17. In some aspects, the anion-conducting channelrhodopsin further comprises a cell-penetrating peptide (CPP) sequence or a cellular receptor-binding sequence. As used herein the terms "cell penetrating peptide" refers to segments of polypeptide sequence that allow a polypeptide to cross the cell membrane (e.g., the plasma membrane in the case a eukaryotic cell). Examples of CPP segments include, but are not limited to, segments derived from HIV Tat (e.g., GRKKRRQRRRPPQ; SEQ ID NO: 25), herpes virus VP22, the *Drosophila* Antennapedia homeobox gene product, protegrin I, Penetratin (RQIKIWFQNRRMKWKK; SEQ ID NO: 26) or melittin (GIGAVLKVLTTGLPALISWIKRKRQQ; SEQ ID NO: 27). In certain aspects the CPP comprises the T1 (TKIESLKEHG; SEQ ID NO: 28), T2 (TQIENLKEKG; SEQ ID NO: 29), 26 (AALEALAEALEALAEALEALAEAAAA; SEQ ID NO:30) or INF7 (GLFEAIEGFIENGWEGMIEGWYGCG; SEQ ID NO: 31) CPP sequence.

In some aspects, expressing comprises administering a vector encoding an anion-conducting channelrhodopsin to the subject. In certain aspects, the vector is a RNA vector. In other aspects, the vector is a DNA vector. In some aspects, the vector is a plasmid, a viral vector or an episomal vector. In certain aspects, the vector further comprises an inducible expression cassette for a suicide gene.

In certain aspects, the sequence encoding the anion-conducting channelrhodopsin is operably linked to a heterologous promoter. In some aspects, the promoter is an inducible or a repressible promoter. In certain aspects, the promoter is a tissue or cell type specific promoter. In particular, the promoter is neuronal cell specific promoter.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 10: (a), Typical photocurrents (black solid lines) generated by PsuACR1 in response to laser photoexcitation (6 ns, 532 nm) at indicated voltages at the amplifier output. The current decay was fit with three exponentials (dashed lines), from which the time constants shown on the plot were derived. (b) Channel closing rates of three known ACRs calculated as reciprocals of the time needed for the peak amplitude to decrease to 50%. (c) The voltage dependence of the amplitudes of current decay components. (d) The dark recovery of the peak current for PsuACR1, GtACR1 and GtACR2 measured in double-flash experiments with 5-ms light pulses of the saturating intensity at 520, 515 and 470 nm, respectively. The numbers on the plot show the dark interval required for 50% peak recovery for each protein. The data points in panels b-d are mean values±SEM (n=3-8 cells).

Figure 12:
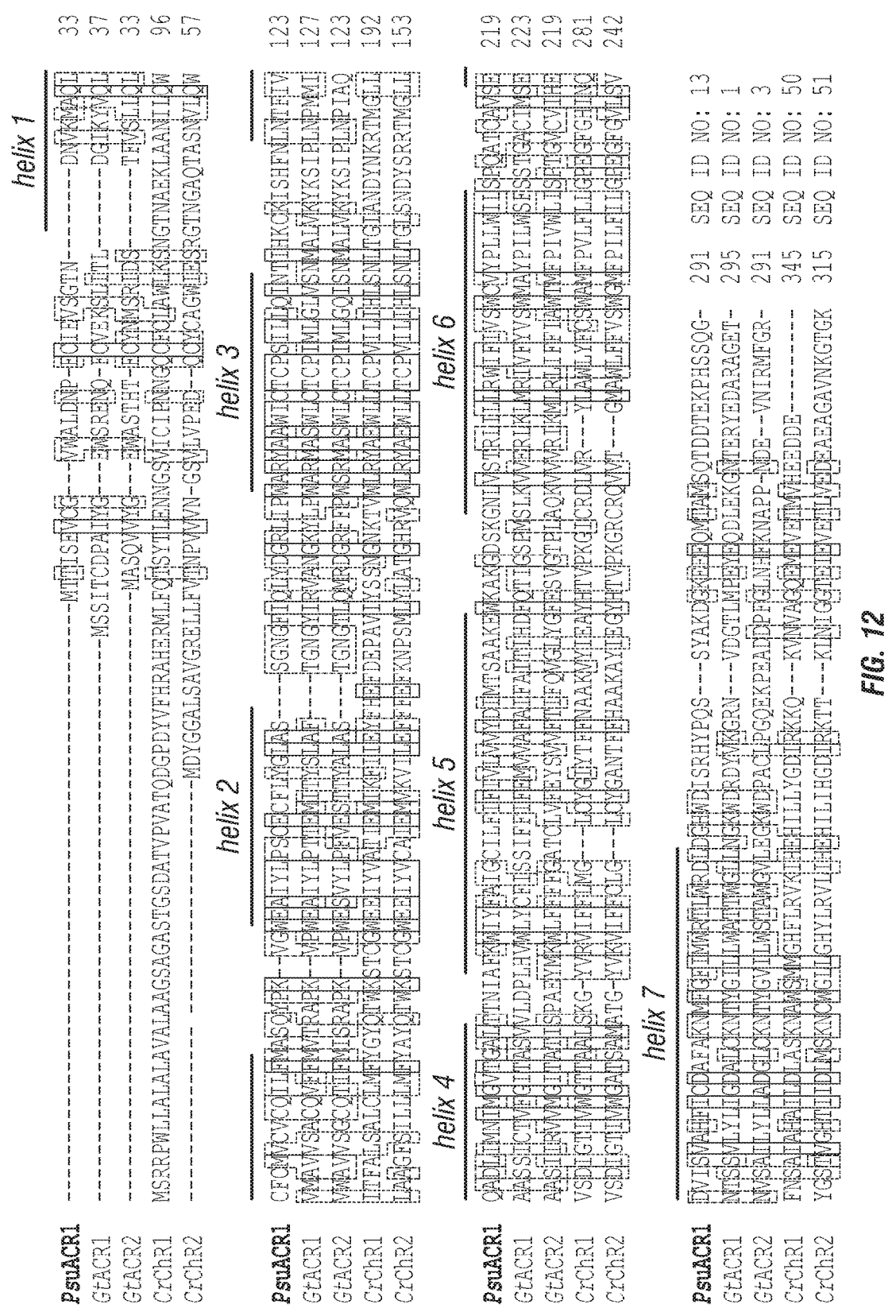

FIG. 12: A ClustalW alignment of the rhodopsin domains of ACRs and *C. reinhardtii* CCRs. The numbers at left show the last residue numbers of each sequence fragment. The carboxylate residues conserved in helices 2 and 3 of CCRs are highlighted red; the corresponding polar and non-polar residues in ACRs are highlighted green and yellow, respectively.

DESCRIPTION OF THE SEQUENCE LISTING

Figures 1A, 1B:
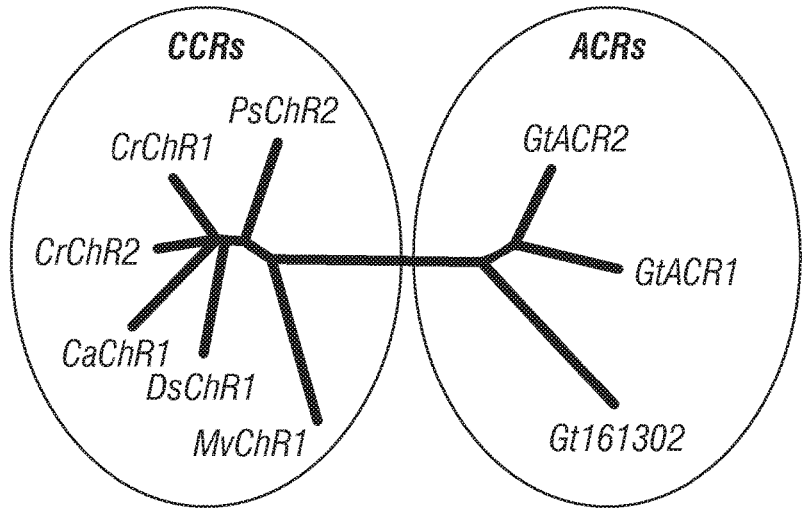
FIG. 1A-F: Phylogeny and photoactivity of *G. theta* ACRs. (A) Phylogenetic tree of cation channelrhodopsins (CCRs) and anion-conducting channelrhodopsins (ACRs). (B and C) ClustalW alignments of transmembrane helices 2 (B) and 3 (C). Abbreviated organism names are: Gt, *Guillardia theta*; Cr, *Chlamydomonas reinhardtii*; Ca, *Chlamydomonas augustae*; Mv, *Mesostigma viride*; Hs, *Halobacterium salinarum*; Nm, *Nonlabens marinus*. The last residue numbers are shown on the right. Conserved Glu residues in the helix 2 are highlighted yellow, and Glu residues in the position of bacteriorhodopsin Asp85 are highlighted red. (D) (Main figure) Photocurrents of GtACR1, GtACR2, and CrChR2 in HEK293 cells in response to a saturating light pulse at −60 mV. (Inset) Mean amplitudes of peak (solid bars) and stationary (hatched bars) currents (n=18-20 cells). Based on noise analysis, the unitary conductance of GtACR2 was 25-fold greater than that reported for the most widely used cation-conducting channelrhodopsin CrChR2. (E) Dependence of the peak and stationary current amplitudes and rise rates on stimulus intensity. (F) Action spectra of photocurrents.

The Sequence Listing shows the amino acid and nucleic acid sequences of anion channel rhodopsin domains that were derived from Sequences encoding 7TM domains of *G. theta* opsins (295, 291 and 288 aa, corresponding to the JGI protein models 111593, 146828 and 161302, respectively) were optimized for human codon usage and were synthesized.

SEQ ID NO: 1 is the amino acid sequence of GtACR1.
SEQ ID NO: 2 is a nucleic acid sequence that encodes GtACR1.
SEQ ID NO: 3 is the amino acid sequence of GtACR2.
SEQ ID NO: 4 is a nucleic acid sequence that encodes GtACR2.
SEQ ID NO: 5 is the amino acid sequence of Gt161302.
SEQ ID NO: 6 is a nucleic acid sequence that encodes Gt161302.
SEQ ID NO: 7 is the amino acid sequence of CrChR1 (*Chlamydomonas reinhardtii* channelrhodopsin 1, aka *Chlamydomonas* sensory rhodopsin A: GenBank accession number AF508965).
SEQ ID NO: 8 is the amino acid sequence of CrChR2 (*Chlamydomonas reinhardtii* channelrhodopsin 2, aka *Chlamydomonas* sensory rhodopsin B: GenBank accession number AF508966).
SEQ ID NO: 9 is the amino acid sequence of CaChR1 (*Chlamydomonas* (*Chloromonas*) *augustae* channelrhodopsin 1: GenBank accession number JN596951).
SEQ ID NO: 10 is the amino acid sequence of MvChR1 (*Mesostigma viride* channelrhodopsin 1: GenBank accession number JF922293).
SEQ ID NO: 11 is the amino acid sequence of HsHR (*Halobacterium salinarum* halorhodopsin: GenBank accession number WP_010902090.1).
SEQ ID NO: 12 is the amino acid sequence of NmHR (*Nonlabens marinus* chloride pumping rhodopsin: GenBank accession number BAO55276.1).
SEQ ID NO: 13 is the amino acid sequence of PsuACR1.
SEQ ID NO: 14 is a synthetic nucleic acid sequence that encodes PsuACR1.
SEQ ID NO: 15 is a synthetic nucleic acid sequence that encodes PsuACR1.
SEQ ID NO: 16 is a synthetic nucleic acid sequence that encodes GtACR1.
SEQ ID NO: 17 is a synthetic nucleic acid sequence that encodes GtACR2.
SEQ ID NO: 18 is a synthetic nucleic acid sequence that encodes Gt161302.
SEQ ID NO: 19 is a synthetic nucleic acid sequence that encodes CrChR1.
SEQ ID NO: 20 is a synthetic nucleic acid sequence that encodes CrChR2.
SEQ ID NO: 21 is a synthetic nucleic acid sequence that encodes CaChR1.
SEQ ID NO: 22 is a synthetic nucleic acid sequence that encodes MChR1.
SEQ ID NO: 23 is a synthetic nucleic acid sequence that encodes HsHR.
SEQ ID NO: 24 is a synthetic nucleic acid sequence that encodes NmHR.

DESCRIPTION OF ILLUSTRATIVE EMBODIMENTS

Until recently channelrhodopsins have been phototaxis receptors that function as light-gated cation channels that when transfected into animal cells, are used for photoactivation of neuron firing. Described herein are a new class of light gated channels, anion channel rhodopsins (ACRs), that provide highly sensitive and efficient membrane hyperpolarization and neuronal silencing through light-gated chloride conduction. ACRs strictly conduct anions, completely excluding protons and larger cations, and hyperpolarize the membrane with 100-fold faster kinetics at 3000-fold lower light intensity than the most efficient currently available optogenetic proteins.

By screening phototaxis receptor currents among several algal species, highly efficient ACRs with rapid kinetics was identified and characterized. In some embodiments, the disclosed methods provide a technology that facilities the identification and characterization of particularly useful channelrhodopsins from algae.

I. Definitions

In this disclosure, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements and components comprising one unit and elements or components that comprise more than one unit unless specifically stated otherwise.

As used herein, the term "about," when used in conjunction with a percentage or other numerical amount, means plus or minus 10% of that percentage or other numerical amount. For example, the term "about 80%," would encompass 80% plus or minus 8%.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls As used herein, and unless otherwise indicated, the term a disorder that involves electrically active cells, such as but not limited to neuronal dysfunction, a neuron mediated disorder, ocular disorder or cardiac disorder, for which the present methods and compositions may be used include, but are not limited to, neuronal dysfunctions, disorders of the brain, the central nervous system, the peripheral nervous system, neurological conditions, disorders of memory and leaning disorders, cardiac arrhythmias, Parkinson's disease, epilepsy, ocular disorders, spinal cord injury, nerve pain associated with, but not limited to autoimmune diseases (for example, multiple sclerosis, Guillain-Barré syndrome, myasthenia gravis, lupus, and inflammatory bowel disease); cancer and the chemotherapy and radiation used to treat it; compression/trauma (for example, pinched nerves in the neck, crush injuries, and carpal tunnel syndrome); diabetic neuropathy; medication side effects; and toxic substances; motor neuron diseases (for example amyotrophic lateral sclerosis, progressive bulbar palsy, progressive muscular atrophy and primary lateral sclerosis); nutritional deficiencies (for example vitamins B6 and B12); Infectious disease; itch sensations associated with, but not limited to eczema, atopic dermatitis, dry skin and allergic itches; diseases and disorders that alter vagal nerve activity, among others.

As used herein, and unless otherwise indicated, the term ocular disorders for which the present methods and compositions may be used to improve one or more parameters of vision include, but are not limited to, developmental abnormalities that affect both anterior and posterior segments of the eye. Anterior segment disorders include, but are not limited to, glaucoma, cataracts, corneal dystrophy, keratoconus. Posterior segment disorders include, but are not limited to, blinding disorders caused by photoreceptor malfunction and/or death caused by retinal dystrophies and degenerations. Retinal disorders include congenital stationary night blindness, age-related macular degeneration, congenital cone dystrophies, and a large group of retinitis pigmentosa (RP)—related disorders.

As used herein, and unless otherwise indicated, the terms "treat," "treating," "treatment" and "therapy" contemplate an action that occurs while a patient is suffering from a disorder that involves electrically active cells, such as but not limited to neuronal dysfunction, a neuron mediated disorder, ocular disorder or cardiac disorder, and which reduces the severity of one or more symptoms or effect of such a disorder. Where the context allows, the terms "treat," "treating," and "treatment" also refers to actions taken toward ensuring that individuals at increased risk of a disorder that involves electrically active cells, such as but not limited to neuronal dysfunction, a neuron mediated disorder, ocular disorder or cardiac disorder and which reduces the severity are able to receive appropriate surgical and/or other medical intervention prior to onset of a disorder that involves electrically active cells, such as but not limited to neuronal dysfunction, a neuron mediated disorder, ocular disorder or cardiac disorder and which reduces the severity. As used herein, and unless otherwise indicated, the terms "prevent," "preventing," and "prevention" contemplate an action that occurs before a patient begins to suffer from a disorder that involves electrically active cells, such as but not limited to neuronal dysfunction, a neuron mediated disorder, ocular disorder or cardiac disorder, that delays the onset of, and/or inhibits or reduces the severity of a disorder that involves electrically active cells, such as but not limited to neuronal dysfunction, a neuron mediated disorder, ocular disorder or cardiac disorder.

As used herein, and unless otherwise indicated, the terms "manage," "managing," and "management" encompass preventing, delaying, or reducing the severity of a recurrence of a disorder that involves electrically active cells, such as but not limited to neuronal dysfunction, a neuron mediated disorder, ocular disorder or cardiac disorder in a patient who has already suffered from such a disease, disorder or condition. The terms encompass modulating the threshold, development, and/or duration of the disorder that involves electrically active cells or changing how a patient responds to the disorder that involves electrically active cells or the maintenance and/or establishment of a desirable membrane potential across the membrane of a cell.

As used herein, and unless otherwise specified, a "therapeutically effective amount" of a compound is an amount sufficient to provide any therapeutic benefit in the treatment or management of a disorder that involves electrically active cells, such as but not limited to neuronal dysfunction, a neuron mediated disorder, ocular disorder or cardiac disorder, or to delay or minimize one or more symptoms associated with a disorder that involves electrically active cells, such as but not limited to neuronal dysfunction, a neuron mediated disorder, ocular disorder or cardiac disorder. A therapeutically effective amount of a compound means an amount of the compound, alone or in combination with one or more other therapies and/or therapeutic agents that provide any therapeutic benefit in the treatment or management of a disorder that involves electrically active cells, such as but not limited to neuronal dysfunction, a neuron mediated disorder, ocular disorder or cardiac disorder.

The term "therapeutically effective amount" can encompass an amount that alleviates a disorder that involves electrically active cells, such as but not limited to neuronal dysfunction, a neuron mediated disorder, ocular disorder or cardiac disorder, improves or reduces a disorder that involves electrically active cells or improves overall therapy, or enhances the therapeutic efficacy of another therapeutic agent.

As used herein, and unless otherwise specified, a "prophylactically effective amount" of a compound is an amount sufficient to prevent or delay the onset of a disorder that involves electrically active cells, such as but not limited to neuronal dysfunction, a neuron mediated disorder, ocular disorder or cardiac disorder or one or more symptoms associated with a disorder that involves electrically active cells or prevent or delay its recurrence. A prophylactically effective amount of a compound means an amount of the compound, alone or in combination with one or more other treatment and/or prophylactic agent that provides a prophylactic benefit in the prevention of a disorder that involves electrically active cells, such as but not limited to neuronal dysfunction, a neuron mediated disorder, ocular disorder or cardiac disorder. The term "prophylactically effective amount" can encompass an amount that prevents a disorder that involves electrically active cells, such as but not limited to neuronal dysfunction, a neuron mediated disorder, ocular disorder or cardiac disorder, improves overall prophylaxis, or enhances the prophylactic efficacy of another prophylactic agent. The "prophylactically effective amount" can be prescribed prior to, for example, the development of a disorder that involves electrically active cells, such as but not limited to neuronal dysfunction, a neuron mediated disorder, ocular disorder or cardiac disorder.

As used herein, "patient" or "subject" includes mammalian organisms which are capable of suffering from a disorder that involves electrically active cells, such as but not limited to neuronal dysfunction, a neuron mediated disorder, ocular disorder or cardiac disorder, as described herein, such as human and non-human mammals, for example, but not limited to, rodents, mice, rats, non-human primates, companion animals such as dogs and cats as well as livestock, e.g., sheep, cow, horse, etc.

As used herein, the term "conservative substitution" generally refers to amino acid replacements that preserve the structure and functional properties of a protein or polypeptide. Such functionally equivalent (conservative substitution) peptide amino acid sequences include, but are not limited to, additions or substitutions of amino acid residues within the amino acid sequences encoded by a nucleotide sequence that result in a silent change, thus producing a functionally equivalent gene product. Conservative amino acid substitutions may be made on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

As used herein, a "redshift" is a shift to longer wavelength. In contrast a "blueshift" would be a shift to shorter wavelength. These terms apply to both light-emitting and light-absorbing objects.

As used herein the phrase "rhodopsin domain" refers to the "rhodopsin fold", a 7-transmembrane-helix (7TM) structure characteristic of rhodopsins. As used herein, the channelopsin is the apoprotein, while channelrhodopsin is the protein and retinal. As used herein the term "channelrhodopsin" describes retinylidene proteins (rhodopsins) that function as light-gated ion channels.

The percent identity or homology is determined with regard to the length of the relevant amino acid sequence. Therefore, if a polypeptide of the present invention is comprised within a larger polypeptide, the percent homology is determined with regard only to the portion of the polypeptide that corresponds to the polypeptide of the present invention and not the percent homology of the entirety of the larger polypeptide. "Percent identity" or "% identity," with reference to nucleic acid sequences, refers to the percentage of identical nucleotides between at least two polynucleotide sequences aligned using the Basic Local Alignment Search Tool (BLAST) engine. See Tatusova et al. (1999) FEMS Microbiol Lett. 174:247-250. The BLAST engine is provided to the public by the National Center for Biotechnology Information (NCBI), Bethesda, Md. To align two polynucleotide sequences, the BLAST which employs the "blastn" program is used.

"Percent identity" or "% identity," with reference to polypeptide sequences, refers to the percentage of identical amino acids between at least two polypeptide sequences aligned using the Basic Local Alignment Search Tool (BLAST) engine. See Tatusova et al. (1999) ibid. The BLAST engine is provided to the public by the National Center for Biotechnology Information (NCBI), Bethesda, Md. To align two polypeptide sequences, the BLAST which employs the "blastp" program is used.

II. Channelrhodopsins

Sequences encoding 7TM domains of *G. theta* opsins (295, 291 and 288 aa, corresponding to the Joint Genome Institute (JGI) sequencing project (http://genome.jgi.doe-.gov/Guith1/Guith1.home.html) protein models 111593, 146828 and 161302, respectively) were optimized for human codon usage and were synthesized and two have been identified and characterized as highly efficient ACRs with rapid kinetics. Some embodiments provided herein are amino acid and nucleic acid sequences of functional domains of novel ACRs that are also functionally characterized. Several such ACRs have been determined to have highly sensitive and efficient a ACRs domains of the channelrhodopsins were cloned and identified as GtACR1 (SEQ ID NO: 1 and 2), GtACR2 (SEQ ID NO: 3 and 4) or Gt161302 (SEQ ID NO: 5 and 6) which were derived from anion-conducting channelrhodopsins of *Guillardia theta*. The functional construct from 111593 is identified as GtACR1 (SEQ ID NO: 1 and 2) and the functional construct from 146828 is identified as GtACR2 (SEQ ID NO: 3 and 4) and were deposited in GenBank (accession numbers KP171708 and KP171709). Also provided in some embodiments is the use and composition of these novel ACR domains, identified as GtACR1, GtACR2 or Gt161302 (SEQ ID NO: 1, SEQ ID NO: 3 or SEQ ID NO: 5).

In some embodiments, are conserved variants of GtACR (for example, GtACR1 or GtACR2) or a peptide fragment thereof. A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues which are typically incorporated by chemical peptide synthesis rather than by synthesis in biological systems. These include, but are not limited to, peptidomimetics and other reversed or inverted forms of amino acid moieties.

In some embodiments, are any of the disclosed methods, wherein the rhodopsin domain of a highly efficient and sensitive anion-conducting channelrhodopsin having the amino acid sequence of all or part of SEQ ID NOS: 1 or 3, or a biologically active fragment thereof that retains the biological activity of the encoded rhodopsin domain of a highly efficient and sensitive anion-conducting channelrhodopsin or a biologically active conservative amino acid substitution variant of SEQ ID NOS: 1 or 3 or of said fragment.

A. Channelrhodopsin Polypeptides

In some embodiments, are isolated polypeptides that encode a rhodopsin domain of a highly efficient and sensitive anion-conducting channelrhodopsin. In some embodiments, an isolated polypeptide comprising the amino acid sequence of SEQ ID NO: 1, SEQ ID NO: 3 or SEQ ID NO: 13. In some embodiments, the isolated polypeptide has at least 85% homology to the amino acid sequence of SEQ ID NO: 1, SEQ ID NO: 3 or SEQ ID NO: 13. In some embodiments, the isolated polypeptide has between 85%-95%-100% homology to the amino acid sequence of SEQ ID NO: 1, SEQ ID NO: 3 or SEQ ID NO: 13.

In some embodiments, is a protein composition comprises a polypeptide having the amino acid sequence of SEQ ID NO: 1, SEQ ID NO: 3 or SEQ ID NO: 13.

The peptide amino acid sequences that can be used in various embodiments including the anion-conducting channelrhodopsin amino acid sequences described herein (SEQ ID NOS: 1 or 3), as well as analogues and derivatives thereof and functional fragments such as but not limited to the rhodopsin/7TM domain. In fact, in some embodiments the any desired peptide amino acid sequences encoded by particular nucleotide sequences can be used, as is the use of any polynucleotide sequences encoding all, or any portion, of desired peptide amino acid sequences. The degenerate nature of the genetic code is well-known, and, accordingly, each anion-conducting channelrhodopsin peptide amino acid-encoding nucleotide sequence is generically representative of the well-known nucleic acid "triplet" codon, or in many cases codons, that can encode the amino acid. As such, as contemplated herein, the anion-conducting channelrhodopsin peptide amino acid sequences described herein, when taken together with the genetic code (see, e.g., "Molecular Cell Biology", Table 4-1 at page 109 (Darnell et al., eds., W.H. Freeman & Company, New York, N.Y., 1986)), are generically representative of all the various permutations and combinations of nucleic acid sequences that can encode such amino acid sequences.

Such functionally equivalent peptide amino acid sequences (conservative substitutions) include, but are not limited to, additions or substitutions of amino acid residues within the amino acid sequences encoded by a nucleotide sequence, but that result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Naturally occurring residues may be divided into classes based on common side chain properties: hydrophobic (Met, Ala, Val, Leu, Ile); neutral hydrophilic (Cys, Ser, Thr, Asn, Gln); acidic (Asp, Glu); basic (His, Lys, Arg); residues that influence chain orientation (Gly, Pro); and aromatic (Trp, Tyr, Phe). For example, non-conservative substitutions may involve the exchange of a member of one of these classes for a member from another class.

In making substitutions, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein, in certain instances, is understood in the art (Kyte et al., J. Mol. Biol., 157:105-131 (1982)). It is known that in certain instances, certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

Substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included.

A skilled artisan will be able to determine suitable variants of a polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides.

In certain embodiments, even areas that may be important for biological activity or for structure may be subject to conservative amino acid substitutions without destroying the biological activity or without adversely affecting the polypeptide structure.

Additionally, in certain embodiments, one skilled in the art can review structure-function studies identifying residues in similar polypeptides that are important for activity or structure. In view of such a comparison, in certain embodiments, one can predict the importance of amino acid residues in a protein that correspond to amino acid residues which are important for activity or structure in similar proteins. In certain embodiments, one skilled in the art may opt for chemically similar amino acid substitutions for such predicted important amino acid residues.

In certain embodiments, one skilled in the art can also analyze the three-dimensional structure and amino acid sequence in relation to that structure in similar polypeptides. In certain embodiments, in view of such information, one skilled in the art may predict the alignment of amino acid residues of a polypeptide with respect to its three dimensional structure. In certain embodiments, one skilled in the art may choose not to make radical changes to amino acid residues predicted to be on the surface of the protein, since such residues may be involved in important interactions with other molecules.

Moreover, in certain embodiments, one skilled in the art may generate test variants containing a single amino acid substitution at each desired amino acid residue. In certain embodiments, the variants can then be screened using activity assays known to those skilled in the art. In certain embodiments, such variants could be used to gather information about suitable variants. For example, in certain embodiments, if one discovered that a change to a particular amino acid residue resulted in destroyed, undesirably reduced, or unsuitable activity, variants with such a change may be avoided. In other words, in certain embodiments, based on information gathered from such routine experiments, one skilled in the art can readily determine the amino acids where further substitutions should be avoided either alone or in combination with other mutations.

A number of scientific publications have been devoted to the prediction of secondary structure. See, e.g., Moult J., Curr. Op. in Biotech., 7(4):422-427 (1996), Chou et al., Biochemistry, 13(2):222-245 (1974); Chou et al., Biochemistry, 113(2):211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The growth of the protein structural database (PDB) has provided enhanced predictability of secondary structure, including the potential number of folds within a polypeptide's structure. See, e.g., Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (see, e.g., Jones, D., Curr. Opin. Struct. Biol., 7(3):377-87 (1997); Sippl et al., Structure, 4(1):15-19 (1996)), "profile analysis" (see, e.g., Bowie et al., Science, 253:164-170 (1991); Gribskov et al., Meth. Enzym., 183: 146-159 (1990); Gribskov et al., Proc. Nat. Acad. Sci., 84(13):4355-4358 (1987)), and "evolutionary linkage" (see, e.g., Holm et al., Nucl. Acid. Res., 27(1):244-247 (1999), and Brenner et al., Curr. Op. Struct. Biol., 7(3):369-376 (1997)).

In certain embodiments, a variant of the reference channelrhodopsin or rhodopsin domain (GtACR) includes a glycosylation variant wherein the number and/or type of glycosylation sites have been altered relative to the amino acid sequence of the reference anion-conducting channelrhodopsin or rhodopsin domain (GtACR). In certain embodiments, a variant of a polypeptide comprises a greater or a lesser number of N-linked glycosylation sites relative to a native polypeptide. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. In certain embodiments, a rearrangement of N-linked carbohydrate chains is provided, wherein one or more N-linked glycosylation sites (typically those that are naturally occurring) are eliminated and one or more new N-linked sites are created. Exemplary variants include cysteine variants wherein one or more cysteine residues are deleted from or substituted for another amino acid (e.g., serine) relative to the amino acid sequence of the reference channelrhodopsin or rhodopsin domain (GtACR). In certain embodiments, cysteine variants may be useful when polypeptides and proteins must be refolded into a biologically active conformation such as after the isolation of insoluble inclusion bodies. In certain embodiments, cysteine variants have fewer cysteine residues than the native polypeptide. In certain embodiments, cysteine variants have an even number of cysteine residues to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in a naturally-occurring sequence (in certain embodiments, in the portion of the polypeptide outside the domain(s) forming intermolecular contacts). In certain embodiments, a conservative amino acid substitution typically may not substantially change the structural characteristics of the reference sequence (e.g., in certain embodiments, a replacement amino acid should not tend to break a helix that occurs in the reference sequence, or disrupt other types of secondary structure that characterizes the reference sequence).

Examples of certain art-recognized polypeptide secondary and tertiary structures are described, for example, in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et at. Nature 354:105 (1991).

In other embodiments, are methods and compositions that provide an ACR with improved properties and characteristics that enhance the application of the compositions in, among other things, optogenetic techniques. Improved properties include, but are not limited to adaptation to human codon usage and synthesis. These embodiments provide greater sensitivity and efficient membrane hyperpolarization and neuronal silencing through light-gated chloride conduction.

B. Fusion Proteins

The use of fusion proteins in which a polypeptide or peptide, or a truncated or mutant version of peptide is fused to an unrelated or homologous protein, polypeptide, or peptide, and can be designed on the basis of the desired peptide encoding nucleic acid and/or amino acid sequences described herein. Such fusion proteins include, but are not limited to: IgFc fusions, which stabilize proteins or peptides and prolong half-life in vivo; fusions to any amino acid sequence that allows the fusion protein to be anchored to the cell membrane; or fusions to an enzyme, fluorescent protein, or luminescent protein that provides a marker function. Fusion proteins to homologous proteins include, but are not limited to, those that are produced from genes that are engineered to encode a portion of the anion-conducting channelrhodopsin fused to a portion of a homologous (orthologous or paralogous) protein of the same of related function. For example, chimeras between different channelrhodopsins may be made to combine beneficial properties uniquely present in each. In some aspects, a chimeric channelrhodopsin of the embodiments comprises about 50%, 55%, 60%, 65%, 70%, 75%, 80%, 85%, 90% or 95% of its sequence from a first channelrhodopsin and the remaining sequence from a second channelrhodopsin. In some aspects, a chimeric channelrhodopsin comprises the rhodopsin domain of a first channelrhodopsin and the remaining sequence from a second channelrhodopsin. In yet further aspects, a chimeric channelrhodopsin can comprise 1, 2, 3, 4, 5 or 6 of its transmembrane domains from a first channelrhodopsin and the remaining transmembrane domains from a second channelrhodopsin.

In certain embodiments, a fusion protein may be readily purified by utilizing an antibody that selectively binds to the fusion protein being expressed. In alternate embodiments, a fusion protein may be purified by subcloning peptide encoding nucleic acid sequence into a recombination plasmid, or a portion thereof, is translationally fused to an amino-terminal (N-terminal) or carboxy-terminal (C-terminal) tag consisting of six histidine residues (a "His-tag"; see, e.g., Janknecht et al., *Proc. Natl. Acad. Sci. USA* 88:8972-8976, 1991). Extracts from cells expressing such a construct are loaded onto Ni' nitriloacetic acid-agarose columns, and histidine-tagged proteins are selectively eluted with imidazole-containing buffers.

C. Nucleic Acids Encoding Channelrhodopsins

In some embodiments, a recombinant nucleic acid operatively linked to a heterologous promoter sequence, said recombinant nucleic acid comprising: a sequence that encodes a peptide with at least 85% homology to an amino acid sequence selected from SEQ ID NO: 1, SEQ ID NO: 3 or SEQ ID NO: 13; or a sequence that encodes a peptide comprising 225 contiguous amino acids selected from SEQ ID NO: 1, SEQ ID NO: 3 or SEQ ID NO: 13; or a sequence that hybridizes to the nucleotide sequence of SEQ ID NO:2, SEQ ID NO:4 or the complement thereof.

In some embodiments, are isolated nucleic acid molecules comprising a nucleotide sequence that encode highly efficient and sensitive anion-conducting channelrhodopsins derived from algae. In some embodiments, the rhodopsin domain encodes the peptides whose sequence is described in SEQ ID NO: 1, SEQ ID NO: 3 or SEQ ID NO: 13. In some embodiments, are isolated nucleic acid molecules comprising a nucleotide sequence that encodes the amino acid sequence shown in SEQ ID NO: 1 or SEQ ID NO: 3. In some embodiments, are expression vectors comprising a nucleic acid sequence that encodes the amino acid sequences of SEQ ID NO: 1, SEQ ID NO: 3 or SEQ ID NO: 13. In some embodiments, are host cells comprising an expression vector comprising a nucleic acid sequence that encodes the amino acid sequences of SEQ ID NO: 1 or SEQ ID NO: 3 or a nucleic acid sequence, fragment of portion thereof of the nucleic acid sequences of SEQ ID NO:2 or SEQ ID NO:4.

In some embodiments, are isolated nucleic acid molecules comprising a nucleotide sequence that was derived from cDNA and encode the rhodopsin domain of an ACR. In some embodiments, the rhodopsin domain encodes the peptides whose sequence is described in SEQ ID NO: 1, SEQ ID NO: 3 or SEQ ID NO: 13. In some embodiments, are isolated nucleic acid molecules that were derived from cDNA that comprise a nucleotide sequence that encodes the amino acid sequence shown in SEQ ID NO: 1, SEQ ID NO: 3 or SEQ ID NO: 13. In some embodiments, are expression vectors comprising a nucleic acid sequence that encodes the amino acid sequences of SEQ ID NO: 1, SEQ ID NO: 3 or SEQ ID NO: 13. In some embodiments, are host cells comprising a recombinant expression vector comprising a nucleic acid sequence that was derived from cDNA and encode the amino acid sequences of SEQ ID NO: 1, SEQ ID NO: 3 or SEQ ID NO: 13.

In some embodiments are isolated peptides comprising an amino acid sequence encoded by at least a portion of the cDNA derived nucleic acid sequences that encode the 7TM or rhodopsin domain of a highly efficient and sensitive ACR. In some embodiments, are isolated peptides comprising an amino acid sequence encoded by a cDNA derived nucleic acid sequence that encodes an amino acid sequence of SEQ ID NO: 1 or SEQ ID NO: 3.

In some embodiments are isolated peptides comprising a contiguous sequence encoded by a nucleic acid sequence that encodes the anion rhodopsin domain of a highly efficient and sensitive anion-conducting channelrhodopsin derived. In some embodiments, are isolated peptides comprising an amino acid sequence of SEQ ID NO: 1, SEQ ID NO: 3, or fragment thereof. In some embodiments, are isolated peptides comprising an amino acid sequence encoded by at least a portion of a nucleic acid sequence of a group consisting of SEQ ID NO:2, SEQ ID NO:4 or SEQ ID NO: 6 and which functions as a anion rhodopsin or anion-conducting channelrhodopsin.

In some embodiments, are isolated peptides comprising an amino acid sequence of SEQ ID NO: 1, SEQ ID NO: 3 or SEQ ID NO: 13 or a 7 TM domain/rhodopsin domain encoded by a cDNA derived nucleic acid sequence of SEQ ID NO:2, SEQ ID NO:4 or SEQ ID NO: 6 and which functions as an anion-conducting channelrhodopsin.

In some embodiments, isolated nucleic acid molecules are provided comprising a nucleotide sequence that encodes the rhodopsin of a highly efficient and sensitive anion-conducting channelrhodopsin. In some embodiments, the rhodopsin encodes a peptide whose sequence is shown in SEQ ID NO: 1, SEQ ID NO: 3 or SEQ ID NO: 13. In some embodiments, are isolated nucleic acid molecules comprising a nucleotide sequence that encodes the amino acid sequence shown in SEQ ID NO: 1, SEQ ID NO: 3 or SEQ ID NO: 13. In some embodiments, are expression vectors comprising a nucleic acid sequence that encodes the amino acid sequences of SEQ ID NO: 1, SEQ ID NO: 3 or SEQ ID NO: 13. In some embodiments, are host cells comprising a expression vector comprising a nucleic acid sequence that encodes the amino acid sequences of SEQ ID NO: 1, SEQ ID NO: 3 or SEQ ID NO: 13. In some embodiments, are peptides comprising a sequence that encodes the rhodopsin domain of a highly efficient and sensitive anion-conducting channelrhodopsin. In some embodiments, are isolated peptides comprising an amino acid sequence of SEQ ID NO: 1, SEQ ID NO: 3 or SEQ ID NO: 13. In some embodiments, the isolated peptides comprise an amino acid sequence of SEQ ID NO: 1, SEQ ID NO: 3 or SEQ ID NO: 13, or fragments thereof.

In some embodiments, are isolated nucleic acid molecules wherein said nucleic acid molecule has a sequence of SEQ ID NO: 2, SEQ ID NO: 4, or SEQ ID NOs: 14-15. In other embodiments, are expression vectors comprising a nucleic acid sequence selected from that shown in SEQ ID NO: 2, SEQ ID NO: 4, or SEQ ID NOs: 14-15 and those that encode the amino acid sequences shown in SEQ ID NO: 1, SEQ ID NO: 3 or SEQ ID NO: 13. In some embodiments, are host cells comprising a expression vector comprising a nucleic acid sequence shown in SEQ ID NO: 2, SEQ ID NO: 4, or SEQ ID NOs: 14-15 and those that encode the amino acid sequences of SEQ ID NO: 1, SEQ ID NO: 3 or SEQ ID NO: 13. In some embodiments, an isolated nucleic acid comprises a nucleotide sequence that encodes the rhodopsin domain of a highly efficient and sensitive anion-conducting channelrhodopsin. In some embodiments, the nucleotide sequence encodes at least 16 contiguous amino acids of SEQ ID NO: 1, SEQ ID NO: 3 or SEQ ID NO: 13. In some embodiments, the nucleotide sequence encodes at least 20 contiguous amino acids of SEQ ID NO: 1, SEQ ID NO: 3 or SEQ ID NO: 13. In some embodiments, the nucleotide sequence encodes at least 35 contiguous amino acids of SEQ ID NO: 1, or SEQ ID NO: 3. In some embodiments, the nucleotide sequence encodes at least 50 contiguous amino acids of SEQ ID NO:1 or SEQ ID NO: 3. In some embodiments, the nucleotide sequence encodes at least 75 contiguous amino acids of SEQ ID NO: 1, SEQ ID NO: 3 or SEQ ID NO: 13. In some embodiments, the nucleotide sequence encodes at least 33 contiguous amino acids of SEQ ID NO: 1, SEQ ID NO: 3 or SEQ ID NO: 13. In some embodiments, the nucleotide sequence encodes a peptide comprising any contiguous portion of SEQ ID NO: 1, SEQ ID NO: 3 or SEQ ID NO: 13.

In some embodiments, are isolated nucleic acids that comprise a nucleotide sequence that encodes the rhodopsin domain of a novel anion-conducting channelrhodopsins derived from *Guillardia theta*. In some embodiments, the nucleotide sequence encodes at least 16 contiguous amino acids of SEQ ID NO: 1, SEQ ID NO: 3 or SEQ ID NO: 13. In some embodiments, the nucleotide sequence encodes at least 20 contiguous amino acids of SEQ ID NO: 1, SEQ ID NO: 3 or SEQ ID NO: 13. In some embodiments, the nucleotide sequence encodes at least 35 contiguous amino acids of SEQ ID NO: 1, SEQ ID NO: 3 or SEQ ID NO: 13. In some embodiments, the nucleotide sequence encodes at least 50 contiguous amino acids of SEQ ID NO: 1, SEQ ID NO: 3 or SEQ ID NO: 13. In some embodiments, the nucleotide sequence encodes at least 75 contiguous amino acids of SEQ ID NO: 1, SEQ ID NO: 3 or SEQ ID NO: 13. In some embodiments, the nucleotide sequence encodes at least 33 contiguous amino acids of SEQ ID NO: 1, SEQ ID NO: 3 or SEQ ID NO: 13. In some embodiments, the nucleotide sequence encodes a peptide comprising SEQ ID NO: 1, SEQ ID NO: 3 or SEQ ID NO: 13.

In some embodiments, an isolated nucleic acid comprising a nucleotide sequence that encodes a functional domain of an anion-conducting channelrhodopsin of *Guillardia theta*. In some embodiments are isolated nucleic acid that encodes at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150, 175, 200, 205, 210, 215, 220, 225, 228, 229, 230, 235, 240 250, 255, 260, 265, 270, 275, 280, 285, 290, 295, 296 or more contiguous amino acids of SEQ ID NO: 1, SEQ ID NO: 3 or SEQ ID NO: 13 or fragments thereof. Further, in some embodiments, any range derivable between any of the above-described integers.

In other embodiments, the present invention provides for an isolated polypeptide or an isolated nucleic acid encoding a polypeptide having in some embodiments between about 70% and about 75%; in further embodiments between about 75% and about 80%; in further still embodiments between about 80% and 90%; or even more further between about 90% and about 99% of amino acids (for example 95%) that are identical to (or homologous to) the amino acids of SEQ ID NO: 1, SEQ ID NO: 3 or SEQ ID NO: 13 or fragments thereof.

In other embodiments, the present invention provides for an isolated nucleic acid encoding a polypeptide having between about 70% and about 75%; or more preferably between about 75% and about 80%; or more preferably between about 80% and about 90%; or even more preferably between about 90% and about 99% of amino acids that are identical to the amino acids of SEQ ID NO: 1, SEQ ID NO: 3 or SEQ ID NO: 13 or fragments thereof.

In some embodiments, the nucleic acid segments, regardless of the length of the coding sequence itself, may be combined with other DNA sequences, such as promoters, enhancers, polyadenylation signals, additional restriction enzyme sites, multiple cloning sites, other coding segments, and the like. In some embodiments, for example, are recombinant nucleic acids comprising a nucleotide sequence that encodes amino acids of SEQ ID NO: 1, SEQ ID NO:3 or fragments thereof, operably linked to a heterologous promoter.

In certain embodiments the invention provides an isolated nucleic acid obtained by amplification from a template nucleic acid using a primer selected from appropriate primer that can be used with SEQ ID NO:2 or SEQ D NO:4.

In some embodiments, are any of the disclosed methods wherein the expression vectors include, but are not limited to, AAV viral vector. In some embodiments, are any of the disclosed methods wherein the promoter is a constitutive promoter. In some embodiments, are any of the disclosed methods wherein the constitutive promoter includes, but is not limited to, a CMV promoter or a hybrid CMV enhancer/chicken β-actin (CAG) promoter. In some embodiments, are any of the disclosed methods wherein the promoter includes, but is not limited to, an inducible and/or a cell type-specific promoter, In some embodiments is a cDNA-derived nucleic acid comprising a nucleic acid sequence that encodes an amino acid sequence selected from SEQ ID NO: 1, SEQ ID NO: 3 or SEQ ID NO: 13. In some embodiments is a cDNA-derived nucleic acid comprising a nucleic acid sequence that encodes an amino acid sequence selected from SEQ ID NO: 1, SEQ ID NO: 3 or SEQ ID NO: 13, wherein the cDNA-derived nucleic acid comprises the nucleic acid sequence of SEQ ID NO: 2, SEQ ID NO: 4, or SEQ ID NOs: 14-15. In other embodiments is an expression vector comprising the cDNA-derived nucleic acid comprising a nucleic acid sequence that encodes an amino acid sequence selected from SEQ ID NO: 1, SEQ ID NO: 3 or SEQ ID NO: 13.

Channelrhodopsin nucleic acid sequences for use in the disclosed methods and compositions include, but are not limited to, the active portion of the presently disclosed algal derived anion-conducting channelrhodopsins GtACR1 (amino acid SEQ ID NO: 1, and nucleic acid sequence SEQ ID NO: 2) and GtACR2 (amino acid SEQ ID NO: 3, and nucleic acid sequence SEQ ID NO: 4), including but not limited to those described, such as but not limited to the nucleic acid sequences that encode the rhodopsin domain, an active portion of the presently disclosed algal derived anion-conducting channelrhodopsins, such as but not limited to the rhodopsin domains disclosed (SEQ ID NO: 1).

In some embodiments, the use of an active portion of a presently disclosed anion-conducting channelrhodopsin, such as but not limited to the rhodopsin domain, includes all or portions of the sequences described herein (and expression vectors comprising the same), and additionally contemplates the use of any nucleotide sequence encoding a contiguous an active portion of the presently disclosed anion-conducting channelrhodopsins, such as but not limited to the rhodopsin domain, open reading frame (ORF) that hybridizes to a complement of an anion-conducting channelrhodopsin or channelopsin sequence described herein under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. ("Current Protocols in Molecular Biology", Vol. 1 and 2 (Ausubel et al., eds., Green Publishing Associates, Incorporated, and John Wiley & Sons, Incorporated, New York, N.Y., 1989)), and encodes a functionally equivalent anion-conducting channelrhodopsin (or active portion thereof, such as but not limited to the rhodopsin domain) gene product or the active portion thereof. Additionally contemplated is the use of any nucleotide sequence that hybridizes to the complement of a DNA sequence that encodes an anion-conducting channelrhodopsin amino acid sequence under moderately stringent conditions, e.g., washing in 0.2×SSC/0.1% SDS at 42° C. ("Current Protocols in Molecular Biology", supra), yet still encodes a functionally equivalent anion-conducting channelrhodopsin product. Functional equivalents of anion-conducting channelrhodopsin include, but are not limited to, naturally occurring versions of anion-conducting channelrhodopsin present in other or the same species (orthologs, paralogs and more generally homologs), and mutant versions of anion-conducting channelrhodopsin, whether naturally occurring or engineered (by site directed mutagenesis, gene shuffling, or directed evolution, as described in, for example, U.S. Pat. No. 5,837,458) or active portion thereof, such as but not limited to the rhodopsin domain. The disclosure also includes the use of degenerate nucleic acid variants (due to the redundancy of the genetic code) of the identified channelrhodopsin polynucleotide sequences.

Additionally contemplated is the use of polynucleotides encoding anion-conducting channelrhodopsin ORFs, or their functional equivalents, encoded by polynucleotide sequences that are about 99, 95, 90, or about 85 percent similar to the corresponding regions of the anion-conducting channelrhodopsin sequences described herein (as measured by BLAST sequence comparison analysis using, for example, the University of Wisconsin GCG sequence analysis package (SEQUENCHER 3.0, Gene Codes Corporation, Ann Arbor, Mich.) using default parameters).

In certain embodiments, the invention concerns isolated nucleic acid segments and recombinant vectors which encode a protein or peptide that includes within its amino acid sequence an amino acid sequence of a channelrhodopsin or a functional portions or variant thereof, such as those identified and cloned: GtACR1 and GtACR2 (SEQ ID NOS: 1 and 3) and PsuACR1 (SEQ ID NO: 13). In some embodiments, a portion of a channelrhodopsin and has relatively few amino acids which are not identical to, or a biologically functional equivalent of, the amino acids of the full-length channelrhodopsin. The term "functional equivalent" is well understood in the art. Accordingly, sequences which have between about 70% and about 80%; or more preferably, between about 85% and about 90%; or even more preferably, between about 90 and 95% and about 99%; of amino acids which are identical or functionally equivalent to the amino acids of the identified and cloned: GtACR1 (SEQ ID NO: 1), GtACR2 (SEQ ID NO: 3) or PsuACR1 (SEQ ID NO: 13).

The nucleic acid segments of the present invention, regardless of the length of the coding sequence itself, may be combined with other sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to nucleic acids that encode the polypeptides of SEQ ID NOS: 1 and 3, such as about 10 to 15 or 20, 30, or 40 or so nucleotides, and which are up to 2000 or so base pairs in length. DNA segments with total lengths of about 8000, 7000, 6000, 5000, 4000, 3000, 2000, 1000, 500, 200, 100 and about 50 base pairs in length are also contemplated to be useful.

In some embodiments, isolated nucleic acids that encode the amino acids of a channelrhodopsin or fragment thereof and recombinant vectors incorporating nucleic acid sequences which encode a channelrhodopsin protein or peptide and that includes within its amino acid sequence an amino acid sequence in accordance with SEQ ID NOS: 1 and 3. In some embodiments, a purified nucleic acid segment that encodes a protein that encodes a channelrhodopsin or fragment thereof, the recombinant vector may be further defined as an expression vector comprising a promoter operatively linked to said channelrhodopsin-encoding nucleic acid segment.

In additional embodiments, is a host cell, made recombinant with a recombinant vector comprising channelrhodopsin-encoding nucleic acid segments. The recombinant host cell may be a prokaryotic cell or a eukaryotic cell. As used herein, the term "engineered" or "recombinant" cell is intended to refer to a cell into which a recombinant gene, such as a gene encoding a channelrhodopsin, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a copy of a genomic gene or a cDNA gene, or will include genes positioned adjacent to a promoter not naturally associated with the particular introduced gene. In some embodiments, nucleic acid molecules having sequence regions consisting of contiguous nucleotide stretches of about 14, 15-20, 30, 40, 50, or even of about 100 to about 200 nucleotides or so, identical or complementary to the channelrhodopsin-encoding nucleic acid sequences.

In some embodiments, the channelrhodopsin-encoding nucleic acid sequences described herein can be targeted to the genome of a host cell using clustered regularly interspaced short palindromic repeats (CRISPR) and CRISPR-associated (Cas) proteins. See Sander and Joung, *Nature Biotechnology*, 32(4): 347-355, incorporated herein by reference. In some embodiments, the CRISPR/Cas nuclease or CRISPR/Cas nuclease system includes a non-coding RNA molecule (guide) RNA, which sequence-specifically binds to DNA, and a Cas protein (e.g., Cas9), with nuclease functionality (e.g., two nuclease domains). In some embodiments, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. In some embodiments, the target site is selected based on its location immediately 5' of a protospacer adjacent motif (PAM) sequence, such as typically NGG, or NAG. In this respect, the gRNA is targeted to the desired sequence by modifying the first 20 nucleotides of the guide RNA to correspond to the target DNA sequence.

In some embodiments, the CRISPR system induces DSBs at the target site, followed by disruptions as discussed herein. In other embodiments, Cas9 variants, deemed "nickases" are used to nick a single strand at the target site. In some aspects, paired nickases are used, e.g., to improve specificity, each directed by a pair of different gRNAs targeting sequences such that upon introduction of the nicks simultaneously, a 5' overhang is introduced.

In some aspects, one or more guide RNAs (ribonucleic acids) direct an enzyme having nuclease activity expressed by the cell, such as a DNA binding protein having nuclease activity, to a target location on the DNA (deoxyribonucleic acid) wherein the enzyme cuts the DNA and an exogenous donor nucleic acid described herein is inserted into the DNA, such as by homologous recombination. Exemplary methods are described, for example, in US Patent Publication No. 20140357530 and International Publication No. WO2015006290, both incorporated herein by reference.

Accordingly, certain embodiments of the present disclosure are based on the use of exogenous DNA (e.g., channelrhodopsin-encoding nucleic acid sequences), nuclease enzymes such as DNA binding proteins and guide RNAs to co-localize to DNA and digest or cut the DNA with insertion of the exogenous DNA, such as by homologous recombination. Such DNA binding proteins are readily known to those of skill in the art to bind to DNA for various purposes. Such DNA binding proteins may be naturally occurring. DNA binding proteins included within the scope of the present disclosure include those which may be guided by RNA, referred to herein as guide RNA. According to this aspect, the guide RNA and the RNA guided DNA binding protein form a co-localization complex at the DNA. Such DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., Nature Reviews, Microbiology, Vol. 9, June 2011, pp. 467-477 including all supplementary information hereby incorporated by reference in its entirety.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain.

D. Recombinant Expression

While the desired peptide amino acid sequences described can be chemically synthesized (see, e.g., "Proteins: Structures and Molecular Principles" (Creighton, ed., W.H. Freeman & Company, New York, N.Y., 1984)), large polypeptides sequences may advantageously be produced by recombinant DNA technology using techniques well-known in the art for expressing nucleic acids containing a nucleic acid sequence that encodes the desired peptide. Such methods can be used to construct expression vectors containing peptide encoding nucleotide sequences and appropriate transcriptional and translational control signals. These methods include, for example, in vitro recombinant DNA techniques, synthetic techniques, and in vivo genetic recombination (see, e.g., "Molecular Cloning, A Laboratory Manual", supra, and "Current Protocols in Molecular Biology", supra). Alternatively, RNA and/or DNA encoding desired peptide encoding nucleotide sequences may be chemically synthesized using, for example, synthesizers (see, e.g., "Oligonucleotide Synthesis: A Practical Approach" (Gait, ed., IRL Press, Oxford, United Kingdom, 1984)).

A variety of host-expression vector systems may be utilized to express peptide encoding nucleotide sequences. When the desired peptide or polypeptide is soluble or a soluble derivative, the peptide or polypeptide can be recovered from the host cell culture, i.e., from the host cell in cases where the peptide or polypeptide is not secreted, and from the culture media in cases where the peptide or polypeptide is secreted by the host cell. However, suitable expression systems also encompass engineered host cells that express the desired polypeptide or functional equivalents anchored in the cell membrane. Purification or enrichment of the desired peptide from such expression systems can be accomplished using appropriate detergents and lipid micelles, and methods well-known to those skilled in the art. Furthermore, such engineered host cells themselves may be used in situations where it is desired not only to retain the structural and functional characteristics of the peptide, but to assess biological activity, e.g., in certain drug screening assays.

In certain applications, transient expression systems are desired. However, for long-term, high-yield production of recombinant proteins or peptides, stable expression is generally preferred. For example, cell lines that stably express the desired protein, polypeptide, peptide, or fusion protein may be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for about 1-2 days in an enriched media, and then switched to a selective media. The selectable marker in the recombinant plasmid confers resistance to the selection, and allows cells to stably integrate the plasmid into their chromosomes and grow to form foci, which in turn can be cloned and expanded into cell lines. This method may advantageously be used to engineer cell lines that express the desired gene products or portions thereof. Such engineered cell lines may be particularly useful in screening and evaluation of compounds that affect the endogenous activity of a desired protein, polypeptide or peptide.

A number of selection systems may be used, including, but not limited to, the herpes simplex virus thymidine kinase (Wigler et al., Cell 11:223-232, 1977), hypoxanthine-guanine phosphoribosyltransferase (Szybalska and Szybalski, *Proc. Natl. Acad. Sci. USA* 48:2026-2034, 1962), and adenine phosphoribosyltransferase (Lowy et al., *Cell* 22:817-823, 1980) genes, which can be employed in tk$^-$, hgprt$^-$ or aprt$^-$ cells, respectively. Anti-metabolite resistance can also be used as the basis of selection for the following genes: dihydrofolate reductase (dhfr), which confers resistance to methotrexate (Wigler et al., *Proc. Natl. Acad. Sci. USA* 77:3567-3570, 1980, and O'Hare et al., *Proc. Natl. Acad. Sci. USA* 78:1527-1531, 1981); guanine phosphoribosyl transferase (gpt), which confers resistance to mycophenolic acid (Mulligan and Berg, *Proc. Natl. Acad. Sci. USA* 78:2072-2076, 1981); neomycin phosphotransferase (neo), which confers resistance to the aminoglycoside G-418 (Colbere-Garapin et al., *J. Mol. Biol.* 150:1-14, 1981); and hygromycin B phosphotransferase (hpt), which confers resistance to hygromycin (Santerre et al., *Gene* 30:147-156, 1984).

Host cells/expression systems that may be used for purpose of providing compositions to be used in the disclosed methods include, but are not limited to, microorganisms such as bacteria (e.g., *E. coli, B. subtilis*) transformed with a recombinant bacteriophage DNA, plasmid DNA, or cosmid DNA expression vector containing a desired peptide encoding nucleotide sequence; yeast (e.g., *Saccharomyces cerevisiae, Pichia pastoris*) transformed with a recombinant yeast expression vector containing a desired peptide encoding nucleotide sequence; insect cell systems infected with a recombinant virus expression vector (e.g., baculovirus) containing a desired peptide encoding nucleotide sequence; plant cell systems infected with a recombinant virus expression vector (e.g., cauliflower mosaic virus, CaMV; tobacco mosaic virus, TMV), or transformed with a recombinant plasmid expression vector (e.g., Ti plasmid), containing a desired peptide encoding nucleotide sequence; or mammalian cell systems (e.g., COS, CHO, BHK, 293, 3T3) harboring a recombinant expression construct containing a desired peptide encoding nucleotide sequence and a promoter derived from the genome of mammalian cells (e.g., metallothionein promoter) or from mammalian viruses (e.g., the adenovirus late promoter, the vaccinia virus 7.5K promoter).

In bacterial systems, a number of different expression vectors may be advantageously selected depending upon the use intended for the desired gene product being expressed. For example, when a large quantity of such a protein is to be produced, such as for the generation of pharmaceutical compositions comprising a desired peptide, or for raising antibodies to the protein, vectors that direct the expression of high levels of fusion protein products that are readily purified may be desirable. Such vectors include, but are not limited to: the *E. coli* expression vector pUR278 (Ruther and Müller-Hill, *EMBO J.* 2:1791-1794, 1983), in which a desired peptide encoding sequence may be ligated individually into the vector in frame with the lacZ coding region so that a fusion protein is produced; pIN vectors (Inouye and Inouye, *Nucleic Acids Res.* 13:3101-3110, 1985, and Van Heeke and Schuster, *J. Biol. Chem.* 264:5503-5509, 1989); and the like. pGEX vectors (GE Healthcare, Piscataway, N.J.) may also be used to express a desired peptide moiety as a fusion protein with glutathione S-transferase (GST). In general, such fusion proteins are soluble and can easily be purified from lysed cells by adsorption to glutathione-agarose beads, followed by elution in the presence of free glutathione. The pGEX vectors are designed to include thrombin or factor Xa protease cleavage sites so that the cloned desired peptide encoding gene product can be released from the GST moiety.

In an exemplary insect system, *Autographa californica* nuclear polyhedrosis virus (AcNPV) is used as a vector to express a desired peptide encoding sequence. The virus grows in *Spodoptera frugiperda* cells. A desired peptide encoding sequence may be cloned individually into a non-essential region (for example the polyhedrin gene) of the virus, and placed under control of an AcNPV promoter (for example the polyhedrin promoter). Successful insertion of a desired peptide encoding sequence will result in inactivation of the polyhedrin gene and production of non-occluded recombinant virus (i.e., virus lacking the proteinaceous coat coded for by the polyhedrin gene). The recombinant viruses are then used to infect *Spodoptera frugiperda* cells in which the inserted polynucleotide is expressed (see, e.g., Smith et al., *J. Virol.* 46:584-593, 1983, and U.S. Pat. No. 4,215,051).

In mammalian host cells, a number of viral-based expression systems may be utilized. In cases where an adenovirus is used as an expression vector, a desired peptide encoding nucleotide sequence may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing desired peptide products in infected hosts (see, e.g., Logan and Shenk, *Proc. Natl. Acad. Sci. USA* 81:3655-3659, 1984). Specific initiation signals may also be required for efficient translation of inserted desired peptide encoding nucleotide sequences. These signals include the ATG initiation codon and adjacent sequences. In some cases exogenous translational control signals, including, perhaps, the ATG initiation codon, may be provided. Furthermore, the initiation codon should be in phase with the reading frame of the desired peptide encoding coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Nevins, *CRC Crit. Rev. Biochem.* 19:307-322, 1986).

In yeast, a number of vectors containing constitutive or inducible promoters may be used. For a review, see, e.g., "Current Protocols in Molecular Biology", supra, Ch. 13, Bitter et al., *Meth. Enzymol.* 153:516-544, 1987, "DNA Cloning", Vol. II, Ch. 3 (Glover, ed., IRL Press, Washington, D.C., 1986); Bitter, *Meth. Enzymol.* 152:673-684, 1987, "The Molecular Biology of the Yeast *Saccharomyces*: Life Cycle and Inheritance" (Strathern et al., eds., Cold Spring Harbor Press, Cold Spring Harbor, N.Y., 1981), and "The Molecular Biology of the Yeast *Saccharomyces*: Metabolism and Gene Expression" (Strathern et al., eds., Cold Spring Harbor Press, Cold Spring Harbor, N.Y., 1982).

In plants, a variety of different plant expression vectors can be used, and expression of a desired peptide encoding sequence may be driven by any of a number of promoters. For example, viral promoters such as the 35S RNA or 19S RNA promoters of CaMV (Brisson et al., *Nature* 310:511-514, 1984), or the coat protein promoter of TMV (Takamatsu et al., *EMBO J.* 6:307-311, 1987) may be used.

Alternatively, plant promoters such as the promoter of the small subunit of RUBISCO (Coruzzi et al., *EMBO J.* 3:1671-1679, 1984, and Broglie et al., Science 224:838-843, 1984), or heat shock promoters, e.g., soybean hsp17.5-E or hsp17.3-B (Gurley et al., *Mol. Cell. Biol.* 6:559-565, 1986) may be used. These constructs can be introduced into plant cells using, for example, Ti plasmids, Ri plasmids, plant virus vectors, direct DNA transformation, microinjection, or electroporation. For reviews of such techniques, see, e.g., Weissbach and Weissbach, in "Methods in Plant Molecular Biology", Section VIII (Schuler and Zielinski, eds., Academic Press, Inc., New York, N.Y., 1988), and "Plant Molecular Biology", $2^{nd}$ Ed., Ch. 7-9 (Grierson and Covey, eds., Blackie & Son, Ltd., Glasgow, Scotland, United Kingdom, 1988).

In addition, a host cell strain may be chosen that modulates the expression of the inserted desired peptide encoding sequence, or modifies and processes the desired peptide encoding nucleic acid sequence in a desired fashion. Such modifications (e.g., glycosylation) and processing (e.g., cleavage) of protein products may affect certain functions of the protein. Different host cells have characteristic and specific mechanisms for post-translational processing and modification of proteins and peptides. Appropriate cell lines or host systems can be chosen to ensure the correct or desired modification and processing of the desired protein, polypeptide, or peptide expressed. To this end, eukaryotic host cells that possess the cellular machinery for desired processing of the primary transcript, and glycosylation and/or phosphorylation of desired peptide encoding nucleic acid sequence be used. Such mammalian host cells include, but are not limited to, Chinese hamster ovary (CHO), VERO, baby hamster kidney (BHK), HeLa, monkey kidney (COS), MDCK, 293, 3T3, WI38, human hepatocellular carcinoma (e.g., Hep G2), and U937 cells.

In some embodiments, a recombinant host cell comprising one of the nucleic acid sequences described. In some embodiments, a protein composition comprising one of the polypeptides described.

III. Methods of Use

In some embodiments, molecular engineered variants (some with improved activity) of the described a highly efficient and sensitive anion-conducting channelrhodopsin by site-specific mutagenesis and chimera construction. In some embodiments, the channelrhodopsins serve as receptors for phototaxis and the photophobic response. Their photoexcitation initiates depolarization of the cell membrane.

In some embodiments, the rhodopsin domains of several anion-conducting channelrhodopsins were cloned and determined to have channel activity when they were expressed in mammalian HEK293 cells. Using these methods new anion-conducting channelrhodopsin variants, were determined to have improved properties with regards to, among other applications, optogenetics.

One of the major challenges for optogenetic applications, especially in living animals, are scattering of the stimulating light by biological tissues and its absorption by hemoglobin. Optogenetic tools with long-wavelength absorption would exhibit minimal light attenuation from these effects, but most microbial rhodopsins do not fall into this category. For instance, the absorption maximum of ChR2, which possesses several other useful properties and is thereby most frequently used as a depolarizing tool in optogenetics, is 470 nm.

Long-wavelength absorption by optogenetic tools is generally considered desirable to increase the penetration depth of the stimulus light by minimizing tissue scattering and absorption by hemoglobin. In some embodiments, the long-wavelength sensitivity of optogenetic microbial rhodopsins is enhanced using 3,4-Dehydroretinal (A2 retinal). A2 retinal (3,4-dehydroretinal) is a natural retinoid, its 11-cis form being found in photoreceptor cells of certain invertebrates, fish and amphibians, where it may constitute the only retinal, or an additional chromophore to A1 retinal. The presence of an additional double bond in the B-ionone ring of the chromophore results in pigments that absorb light at longer wavelengths, as compared to those formed with A1 (regular) retinal. Variations in A1/A2 ratio cause natural adaptive tuning of spectral sensitivity of vision in the organisms during adaptation to external conditions. Reconstitution of bleached microbial rhodopsins (bacteriorhodopsin, halorhodopsin, sensory rhodopsins I and II) in vitro with all-trans 3,4-dehydroretinal (A2 retinal) also shifts their absorption spectra to longer wavelengths. In some embodiments, spectral properties of optogenetic tools were modified by incorporation of all-trans A2 retinal. The addition of A2 retinal, both ion pumps and channelrhodopsins form functional pigments with significantly red-shifted absorption.

In some embodiments, the long-wavelength sensitivity of optogenetic microbial rhodopsins is enhanced using A2 retinal. In some embodiments, chromophore substitution provides a complementary strategy to improve the efficiency of optogenetic tools. Substitution of A1 retinal by A2 retinal significantly shifts the spectral sensitivity of tested rhodopsins to longer wavelengths typically without altering other aspects of their function.

Optogenetic techniques involve the introduction of light-activated channels and enzymes that allow manipulation of neural activity and control of neuronal function. Thus, in some embodiments, the disclosed methods and compositions can be introduced into cells and facilitate the manipulation of the cells activity and function. See, for example, US publication 20130090454 of U.S. application Ser. No. 13/622,809, as well as, Mattis, J., Tye, K. M., Ferenczi, E. A., Ramakrishnan, C., O'Shea, D. J., Prakash, R., Gunaydin, L. A., Hyun, M., Fenno, L. E., Gradinaru, V., Yizhar, O., and Deisseroth, K. (2012) Principles for applying optogenetic tools derived from direct comparative analysis of microbial opsins. Nat. Methods 9, 159-172; and Zhang, F., Vierock, J., Yizhar, O., Fenno, L. E., Tsunoda, S., Kianianmo-meni, A., Prigge, M., Berndt, A., Cushman, J., Polle, J., Magnuson, J., Hege-mann, P., and Deisseroth, K. (2011) The microbial opsin family of optogenetic tools. Cell 147, 1446-1457).

Optogenetic techniques, and thus the disclosed methods and compositions, can be used to characterize the functions of complex neural circuits and information processing in the normal brain and during various neurological conditions; functionally map the cerebral cortex; characterize and manipulate the process of learning and memory; characterize and manipulate the process of synaptic transmission and plasticity; provide light-controlled induction of gene expression; provide optical control of cell motility and other activities.

Clinical applications of the disclosed methods and compositions include (but are not limited to) optogenetic approaches to therapy such as: restoration of vision by introduction of channelrhodopsins in post-receptor neurons in the retina for ocular disorder gene-therapy treatment of age-dependent macular degeneration, diabetic retinopathy, and retinitis pigmentosa, as well as other conditions which result in loss of photoreceptor cells; control of cardiac function by using channelrhodopsins incorporated into excitable cardiac muscle cells in the atrioventricular bundle (bundle of His) to control heart beat rhythm rather than an electrical pacemaker device; restoration of dopamine-related movement dysfunction in Parkinsonian patients; amelioration of depression; recovery of breathing after spinal cord injury; provide noninvasive control of stem cell differentiation and assess specific contributions of transplanted cells to tissue and network function. Any group of electrically active cells may be amenable to ACR suppression, including, but not limited to those listed above and cardiomyocytes. Such ACRs are also potentially useful for efficient photoinhibition of cardiomyocyte action potentials thereby enabling treatment of cardiac dysfunctions including, but not limited to, tachycardia. In some embodiments, the presently described compositions and methods can be used to facilitate optical stimulation of cardiac cells and tissues, without negative electrophysiological effects of current cardiac anti-arrhythmia therapies and alleviate symptoms by stimulating or silencing specific regions with abnormal excitation in the heart or the brain. In some embodiments, such optogenetic-based techniques could be used to silence, restore or reset irregular heartbeat in patients some of which now receive implantable devices.

In some embodiments, the presently described compositions and methods can be used to influence cardiac cells or regions by either direct viral gene delivery (such as but not limited to AAV) or by delivery of ACR-carrying donor cells (such as but not limited to cardiomyocytes, Purkinje and His bundle cells, etc.) generated or transformed in culture.

In some embodiments, a method of membrane hyperpolarization of a cell in a subject suffering from a neuron mediated disorder, said method comprising: delivering to the cell of said subject an expression vector comprising a polynucleotide that encodes an amino acid sequence selected from the group consisting of SEQ ID NO: 1, SEQ ID NO: 3 or SEQ ID NO: 13, which encodes a rhodopsin domain of an anion-conducting channelrhodopsin expressible in said cell; and expressing said vector in said cell, wherein the expression of the rhodopsin results in membrane hyperpolarization.

In some embodiments, a method of neuronal silencing in a subject suffering from a neuron mediated disorder, said method comprising: delivering to a target neuron of said subject an expression vector comprising a polynucleotide that encodes an amino acid sequence selected from the group consisting of SEQ ID NO: 1, SEQ ID NO: 3 or SEQ ID NO: 13, which encodes a rhodopsin domain of an anion-conducting channelrhodopsin expressible in said target neuron; and expressing said vector in said target neuron, wherein the expression of the rhodopsin results in silencing of the signal from the target neuron.

In some embodiments, a method of restoring photosensitivity to a retina of a subject suffering from vision loss or blindness, said method comprising: delivering to the retina of said subject an expression vector comprising a polynucleotide that encodes an amino acid sequence selected from the group consisting of SEQ ID NO: 1, SEQ ID NO: 3 or SEQ ID NO: 13 which encodes a rhodopsin domain of an anion-conducting channelrhodopsin expressible in a retinal neuron; and expressing said vector in said retinal neuron, wherein the expressed rhodopsin renders a high level of membrane potential in said retinal neuron.

Therefore, in some embodiments an anion-conducting channelrhodopsin, light-gated anion channels that provide highly sensitive and efficient membrane hyperpolarization is provided as GtACR1 (SEQ ID NO: 1) and GtACR2 (SEQ ID NO: 3) which were derived from anion-conducting channelrhodopsin of *Guillardia theta* and may be used to enhance optogenetic techniques and optogenetic approaches to therapy.

Anion-conducting channelrhodopsins, functional or active portions thereof, such as but not limited to the rhodopsin domain, and functional equivalents include, but are not limited to, naturally occurring versions of ACR and those that are orthologs and homologs, and mutant versions of ACR, whether naturally occurring or engineered (by site directed mutagenesis, gene shuffling, or directed evolution, as described in, for example, U.S. Pat. No. 5,837,458). Also included are the use of degenerate nucleic acid variants (due to the redundancy of the genetic code) of the disclosed algae ACR derived polynucleotide sequences.

In some embodiments, are methods of treating a neuronal disorder, comprising: (a) delivering to a target neuron a nucleic acid expression vector that encodes a rhodopsin domain of a highly efficient and sensitive anion-conducting channelrhodopsin, expressible in said target neuron, said vector comprising an open reading frame encoding the rhodopsin domain of a highly efficient and sensitive anion-conducting channelrhodopsin, operatively linked to a promoter sequence, and optionally, a transcriptional regulatory sequence; and (b) expressing said vector in said target neuron, wherein the expressed rhodopsin that results in highly sensitive and efficient membrane hyperpolarization and neuronal silencing of said target neuron upon exposure to light. In some embodiments, the rhodopsin domain is encoded by SEQ ID NO: 1 or SEQ ID NO:3.

In some embodiments, are methods of treating a neuronal disorder, comprising: (a) delivering to a target neuron a nucleic acid expression vector that encodes a rhodopsin domain of an anion-conducting channelrhodopsin derived from algae, expressible in said target neuron, said vector comprising an open reading frame encoding the rhodopsin domain of an anion-conducting channelrhodopsin, operatively linked to a promoter sequence, and optionally, a transcriptional regulatory sequence; and (b) expressing said vector in said target neuron, wherein the expressed rhodopsin silences said target neuron upon exposure to light. In some embodiments, the rhodopsin domain is encoded by SEQ ID NO: 1, SEQ ID NO: 3 or SEQ ID NO: 13.

In some embodiments, are methods of restoring light sensitivity to a retina, comprising: (a) delivering to a retinal neuron a nucleic acid expression vector that encodes a rhodopsin domain of a highly efficient and sensitive anion-conducting channelrhodopsin, expressible in the retinal neuron; said vector comprising an open reading frame encoding the rhodopsin domain of a highly efficient and sensitive anion-conducting channelrhodopsin operatively linked to a promoter sequence, and optionally, a transcriptional regulatory sequence; and (b) expressing said vector in said retinal neuron, wherein the expressed rhodopsin renders said retinal neuron photosensitive, thereby restoring light sensitivity to said retina or a portion thereof. In some embodiments, the rhodopsin domain is encoded by SEQ ID NO: 1, SEQ ID NO: 3 or SEQ ID NO: 13.

In some embodiments, are methods of restoring light sensitivity to a retina, comprising: (a) delivering to a retinal neuron a nucleic acid expression vector that encodes a rhodopsin domain of a highly efficient and sensitive anion-conducting channelrhodopsin, expressible in the retinal neuron; said vector comprising an open reading frame encoding the rhodopsin domain of a highly efficient and sensitive anion-conducting channelrhodopsin operatively linked to a promoter sequence, and optionally, a transcriptional regulatory sequence; and (b) expressing said vector in said retinal neuron, wherein the expressed rhodopsin renders said retinal neuron photosensitive, thereby restoring light sensitivity to said retina or a portion thereof. In some embodiments, the rhodopsin domain is encoded by SEQ ID NO: 1, SEQ ID NO: 3 or SEQ ID NO: 13.

In some embodiments, are methods of restoring photosensitivity to a retina of a subject suffering from vision loss or blindness in whom retinal photoreceptor cells are degenerating or have degenerated and died, said method comprising: (a) delivering to the retina of said subject a nucleic acid vector that encodes a rhodopsin domain of a highly efficient and sensitive anion-conducting channelrhodopsin expressible in a retinal neuron; said vector comprising an open reading frame encoding the rhodopsin domain of a highly efficient and sensitive anion-conducting channelrhodopsin operatively linked to a promoter sequence, and optionally, a transcriptional regulatory sequence; and (b) expressing said vector in said retinal neuron, wherein the expressed rhodopsin renders said retinal neuron photosensitive, thereby restoring photosensitivity to said retina or a portion thereof. In some embodiments, the rhodopsin domain is encoded by SEQ ID NO: 1, SEQ ID NO: 3 or SEQ ID NO: 13.

In some embodiments, the presently described compositions and methods can be used to facilitate optical stimulation of cardiac cells and tissues, without negative electrophysiological effects of current cardiac anti-arrhythmia therapies and alleviate symptoms by stimulating or silencing specific regions with abnormal excitation in the heart or the brain. In some embodiments, such optogenetic based techniques could be used to silence, restore or reset irregular heartbeat in patients some of which now receive implantable devices.

In some embodiments, the presently described compositions and methods can be used to influence cardiac cells or regions by either direct viral gene delivery (such as but not limited to AAV) or by delivery of ACR-carrying donor cells (such as but not limited to cardiomyocytes, Purkinje and His bundle cells, etc.) generated or transformed in culture.

In some embodiments is a method of treating a disorder in an electrically active cell in a subject suffering from a disorder that involves electrically active cells, said method comprising: (a) delivering to the cell of said subject an expression vector comprising a polynucleotide that encodes an amino acid sequence selected from SEQ ID NO: 1, SEQ ID NO: 3 or SEQ ID NO: 13 expressible in said cell; and (b) expressing said vector in said electrically active cell, wherein the expressed rhodopsin silences the signal from said electrically active cell.

In some embodiments is a method of treating a disorder in an electrically active cell in a subject suffering from a disorder that involves electrically active cells, said method comprising: (a) delivering to said subject a transgenic cell comprising an expression vector comprising a polynucleotide that encodes an amino acid sequence selected from SEQ ID NO: 1, SEQ ID NO: 3 or SEQ ID NO: 13 expressible in said transgenic cell; and (b) expressing said vector in said transgenic cell, wherein the expression silences the signal from a electrically active cell.

In some embodiments is a method of silencing an electrically active cell in a subject suffering from an electrically active cell mediated disorder, said method comprising: (a) delivering to a target neuron of said subject an expression vector comprising a polynucleotide that encodes an amino acid sequence selected from SEQ ID NO: 1, SEQ ID NO: 3 or SEQ ID NO: 13 which encodes a rhodopsin domain of an anion-conducting channelrhodopsin expressible in said target neuron; and (b) expressing said vector in said target electrically active cell, wherein the expressed rhodopsin results in silencing of the signal from the electrically active cell. In some embodiments is a recombinant host cell, wherein said host cell is an isolated an electrically active cell.

In some embodiments, a method of treating a neuronal disorder comprises: (a) delivering to a target neuron a nucleic acid expression vector that encodes a rhodopsin domain of a highly efficient and sensitive anion-conducting channelrhodopsin, expressible in said target neuron; said vector comprising an open reading frame encoding the rhodopsin domain of a highly efficient and sensitive anion-conducting channelrhodopsin operatively linked to a promoter sequence, and optionally, transcriptional regulatory sequences; and (b) expressing the expression vector in the target neuron, wherein the expressed anion-conducting channelrhodopsin silences the target neuron upon exposure to light. In some embodiments an above-described expression vector also comprises one or more transcriptional regulatory sequences operably linked to the promoter and rhodopsin domain sequences. In some embodiments, the rhodopsin domain of a highly efficient and sensitive anion-conducting channelrhodopsin has the amino acid sequence of all or part of SEQ ID NOS: 1 or 3 and the rhodopsin domain sequences of SEQ ID NO: 1 or 3, or a biologically active fragment thereof that retains the biological activity of the encoded rhodopsin domain of a channelrhodopsin or is a biologically active conservative amino acid substitution variant of SEQ ID NOS: 1 or 3 or of said fragment. In some embodiments, the expression vector comprises an AAV viral vector. In some embodiments, the promoter is a constitutive promoter. In some embodiments, the constitutive promoter is a CMV promoter or a hybrid CMV enhancer/chicken β-actin (CAG) promoter. In some embodiments, the promoter is an inducible and/or a cell type-specific promoter.

In some embodiments, a method of restoring light sensitivity to a retina comprises (a) delivering to a retinal neuron in a subject a nucleic acid expression vector that encodes a rhodopsin domain of a highly efficient and sensitive anion-conducting channelrhodopsin, expressible in the retinal neuron; said expression vector comprising an open reading frame encoding the rhodopsin domain of a highly efficient and sensitive anion-conducting channelrhodopsin operatively linked to a promoter sequence, and optionally, one or more transcriptional regulatory sequences; and (b) expressing the expression vector in the retinal neuron, wherein the expressed rhodopsin renders the retinal neuron photosensitive, thereby restoring light sensitivity to the retina or a portion thereof. In some embodiments, the rhodopsin domain of a highly efficient and sensitive anion-conducting channelrhodopsin has the amino acid sequence of all or part of SEQ ID NOS: 1 or 3 and the rhodopsin domain sequences of SEQ ID NO: 1 or 3, or a biologically active fragment thereof that retains the biological activity of the encoded rhodopsin domain of a highly efficient and sensitive anion-conducting channelrhodopsin or is a biologically active conservative amino acid substitution variant of SEQ ID NOS: 1, 3 or 13 and the rhodopsin domain sequences of SEQ ID NO: 1, 3 or 13, or of said fragment. In some embodiments, the expression vector comprises an AAV (e.g., AAV2) viral vector. In some embodiments, the promoter is a constitutive promoter. In some embodiments, the constitutive promoter is a CMV promoter or a hybrid CMV enhancer/chicken β-actin (CAG) promoter. In some embodiments, the promoter is an inducible and/or a cell type-specific promoter.

In some embodiments, a method of restoring photosensitivity to a retina of a subject suffering from vision loss or blindness in whom retinal photoreceptor cells are degenerating or have degenerated and died comprises: (a) delivering to the retina of the subject a nucleic acid expression vector that encodes a rhodopsin domain of a highly efficient and sensitive anion-conducting channelrhodopsin expressible in retinal neurons; said expression vector comprising an open reading frame encoding the rhodopsin domain of a highly efficient and sensitive anion-conducting channelrhodopsin operatively linked to a promoter sequence, and optionally, transcriptional regulatory sequences; and (b) expressing the expression vector in the retinal neuron, wherein the expression of the rhodopsin renders the retinal neuron photosensitive, thereby restoring photosensitivity to said retina or a portion thereof. In some embodiments, the rhodopsin domain of a highly efficient and sensitive anion-conducting channelrhodopsin has the amino acid sequence of all or part of SEQ ID NOS: 1, 3 or 13 and the rhodopsin domain sequences of SEQ ID NO: 1, 3 or 13, or a biologically active fragment thereof that retains the biological activity of the encoded rhodopsin domain of a highly efficient and sensitive anion-conducting channelrhodopsin or is a biologically active conservative amino acid substitution variant of SEQ ID NOS: 1, 3 or 13 and the rhodopsin domain sequences of SEQ ID NO: 1, 3 or 13, or of said fragment. In some embodiments, the expression vector comprises an AAV (e.g., AAV2) viral vector. In some embodiments, the promoter is a constitutive promoter. In some embodiments, the constitutive promoter is a CMV promoter or a hybrid CMV enhancer/chicken β-actin (CAG) promoter. In other embodiments, the promoter is an inducible and/or a cell type-specific promoter.

A. Compositions as Therapeutics

The use of channelrhodopsins, or active fragments thereof such as but not limited to the rhodopsin domain as therapeutics. In certain embodiments the presently disclosed compositions and are used to improve optogenetic techniques and applications as well as can be used to aid in diagnosis, prevention, and/or treatment of among other things neuron mediated disorders, neurologic disorders (such as Parkinson's disease) and as therapy for ocular disorders.

In certain embodiments the presently disclosed compositions can be administered in combination with one or more additional compounds or agents ("additional active agents") for the treatment, management, and/or prevention of among other things neuron mediated disorders, neurologic disorders (such as Parkinson's disease) and as therapy for ocular disorders. Such therapies can be administered to a patient at therapeutically effective doses to treat or ameliorate, among other things, neuron mediated disorders, neurologic disorders (such as Parkinson's disease) and as therapy for ocular disorders. A therapeutically effective dose refers to that amount of the compound sufficient to result in any delay in onset, amelioration, or retardation of disease symptoms.

Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, expressed as the ratio $LD_{50}/ED_{50}$. Compositions that exhibit large therapeutic indices are preferred. Compounds that exhibit toxic side effects may be used in certain embodiments, however, care should usually be taken to design delivery systems that target such compositions preferentially to the site of affected tissue, in order to minimize potential damage to uninfected cells and, thereby, reduce side effects.

Data obtained from cell culture assays and animal studies can be used in formulating a range of dosages for use in humans. The dosages of such compositions lie preferably within a range of circulating concentrations that include the $ED_{50}$ with little or no toxicity. The dosage may vary within this range depending on the dosage form employed and the route of administration utilized. For any composition, the therapeutically effective dose can be estimated initially from cell culture assays. A dose may be formulated in animal models to achieve a circulating plasma concentration range that includes the $IC_{50}$ (i.e., the concentration of the test composition that achieves a half-maximal inhibition of symptoms) as determined in cell culture. Such information can be used to more accurately determine useful doses in humans. Plasma levels may be measured, for example, by high performance liquid chromatography.

When the therapeutic treatment of among other things neurologic disorders (such as Parkinson's disease) and as therapy for ocular disorders is contemplated, the appropriate dosage may also be determined using animal studies to determine the maximal tolerable dose, or MTD, of a bioactive agent per kilogram weight of the test subject. In general, at least one animal species tested is mammalian. Those skilled in the art regularly extrapolate doses for efficacy and avoiding toxicity to other species, including human. Before human studies of efficacy are undertaken, Phase I clinical studies help establish safe doses.

Additionally, the bioactive agent may be coupled or complexed with a variety of well-established compositions or structures that, for instance, enhance the stability of the bioactive agent, or otherwise enhance its pharmacological properties (e.g., increase in vivo half-life, reduce toxicity, etc.).

Such therapeutic agents can be administered by any number of methods known to those of ordinary skill in the art including, but not limited to, inhalation, subcutaneous (sub-q), intravenous (I.V.), intraperitoneal (I.P.), intramuscular (I.M.), or intrathecal injection, or topically applied (transderm, ointments, creams, salves, eye drops, and the like), as described in greater detail below.

B. Pharmaceutical Compositions

Pharmaceutical compositions for use in accordance with the presently described compositions may be formulated in conventional manners using one or more physiologically acceptable carriers or excipients.

The pharmaceutical compositions can comprise formulation materials for modifying, maintaining, or preserving, for example, the pH, osmolarity, viscosity, clarity, color, isotonicity, odor, sterility, stability, rate of dissolution or release, adsorption or penetration of the composition. Suitable formulation materials include, but are not limited to: amino acids (for example, glycine, glutamine, asparagine, arginine and lysine); antimicrobials; antioxidants (for example, ascorbic acid, sodium sulfite and sodium hydrogen-sulfite); buffers (for example, borate, bicarbonate, Tris-HCl, citrates, phosphates and other organic acids); bulking agents (for example, mannitol and glycine); chelating agents (for example, ethylenediamine tetraacetic acid (EDTA)); complexing agents (for example, caffeine, polyvinylpyrrolidone, beta-cyclodextrin, and hydroxypropyl-beta-cyclodextrin); fillers; monosaccharides, disaccharides, and other carbohydrates (for example, glucose, mannose and dextrins); proteins (for example, serum albumin, gelatin and immunoglobulins); coloring, flavoring, and diluting agents;

emulsifying agents; hydrophilic polymers (for example, polyvinylpyrrolidone); low molecular weight polypeptides; salt-forming counterions (for example, sodium); preservatives (for example, benzalkonium chloride, benzoic acid, salicylic acid, thimerosal, phenethyl alcohol, methylparaben, propylparaben, chlorhexidine, sorbic acid and hydrogen peroxide); solvents (for example, glycerin, propylene glycol and polyethylene glycol); sugar alcohols (for example, mannitol and sorbitol); suspending agents; surfactants or wetting agents (for example, pluronics, PEG, sorbitan esters, polysorbates (for example, polysorbate 20 and polysorbate 80), triton, tromethamine, lecithin, cholesterol, and tyloxapal); stability enhancing agents (for example, sucrose and sorbitol); tonicity enhancing agents (for example, alkali metal halides (for example, sodium or potassium chloride), mannitol, and sorbitol); delivery vehicles; diluents; excipients; and pharmaceutical adjuvants ("Remington's Pharmaceutical Sciences", 18$^{th}$ Ed. (Gennaro, ed., Mack Publishing Company, Easton, Pa., 1990)).

Additionally, the described therapeutic peptides can be linked to a half-life extending vehicle. Certain exemplary half-life extending vehicles are known in the art, and include, but are not limited to, the Fc domain, polyethylene glycol, and dextran (see, e.g., PCT Patent Application Publication No. WO 99/25044).

These agents may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The agents may also be formulated as compositions for rectal administration such as suppositories or retention enemas, e.g., containing conventional suppository bases such as cocoa butter or other glycerides.

In addition to the formulations described previously, the agents may also be formulated as a depot preparation. Such long acting formulations may be administered by implantation (for example subcutaneously or intramuscularly) or by intramuscular injection. For example, agents may be formulated with suitable polymeric or hydrophobic materials (for example as an emulsion in an acceptable oil), ion exchange resins, or as sparingly soluble derivatives, for example, as a sparingly soluble salt. The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

Active compositions can be administered by controlled release means or by delivery devices that are well-known to those of ordinary skill in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof, to provide the desired release profile in varying proportions. Exemplary sustained release matrices include, but are not limited to, polyesters, hydrogels, polylactides (see, e.g., U.S. Pat. No. 3,773,919 and European Patent Application Publication No. EP 058,481), copolymers of L-glutamic acid and gamma ethyl-L-glutamate (see, e.g., Sidman et al., *Biopolymers* 22:547-556, 1983), poly (2-hydroxyethyl-methacrylate) (see, e.g., Langer et al., *J. Biomed. Mater. Res.* 15:167-277, 1981, and Langer, *Chemtech* 12:98-105, 1982), ethylene vinyl acetate (Langer et al., supra), and poly-D(–)-3-hydroxybutyric acid (European Patent Application Publication No. EP 133,988). Sustained release compositions may include liposomes, which can be prepared by any of several methods known in the art (see, e.g., Eppstein et al., *Proc. Natl. Acad. Sci. USA* 82:3688-3692, 1985, and European Patent Application Publication Nos. EP 036,676, EP 088, 046, and EP 143,949). Suitable controlled-release formulations known to those of ordinary skill in the art, including those described herein, can be readily selected for use with the presently disclosed compositions. Certain embodiments encompass single unit dosage forms suitable for oral administration such as, but not limited to, tablets, capsules, gelcaps, and caplets that are adapted for controlled-release.

All controlled-release pharmaceutical products have a common goal of improving therapy over that achieved by their non-controlled counterparts. Ideally, use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of active ingredient that promptly produces the desired therapeutic effect, and gradually and continually release other amounts of active ingredient to maintain this level of therapeutic or prophylactic effect over an extended period of time. In order to maintain this relatively constant level of active ingredient in the body, the drug must be released from the dosage form at a rate that will replace the amount of active ingredient being metabolized and excreted from the body. Controlled-release of an active ingredient can be stimulated by various conditions including, but not limited to, pH, temperature, enzymes, water, or other physiological conditions or compositions.

In some cases, active ingredients of the disclosed methods and compositions are preferably not administered to a patient at the same time or by the same route of administration. Therefore, in some embodiments are kits that, when used by the medical practitioner, can simplify the administration of appropriate amounts of active ingredients to a patient.

A typical kit comprises a single unit dosage form of one or more of the therapeutic agents disclosed, alone or in combination with a single unit dosage form of another agent that may be used in combination with the disclosed compositions. Disclosed kits can further comprise devices that are used to administer the active ingredients. Examples of such devices include, but are not limited to, syringes, drip bags, patches, and inhalers.

Disclosed kits can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. However, in specific embodiments, the disclosed formulations do not contain any alcohols or other co-solvents, oils or proteins.

C. Transgenic Animals

The present disclosure provides methods and compositions for the creation and use of both human and non-human transgenic animals that carry an algae derived anion-conducting channelrhodopsin transgene in all their cells, as well as non-human transgenic animals that carry an algae derived anion-conducting channelrhodopsin transgene in some, but not all their cells, for example in certain electrically active cells. Human and non-human mammals of any species, including, but not limited to, mice, rats, rabbits, guinea pigs, pigs, micro-pigs, goats, and non-human primates, e.g., baboons, monkeys, and chimpanzees, can be used to generate transgenic animals carrying an algae derived anion-conducting channelrhodopsin polynucleotide (and/or expressing an algae derived polypeptide) may be integrated as a single transgene or in concatamers, e.g., head-to-head or head-to-tail tandems. An algae derived anion-conducting channelrhodopsin transgene may also be selectively introduced into and activated in a particular cell-type (see, e.g., Lakso et al., *Proc. Natl. Acad. Sci. USA* 89:6232-6236, 1992). The regulatory sequences required for such a cell-type specific activation will depend upon the particular cell-type of interest, and will be apparent to those of skill in the art.

Should it be desired that an algae-derived anion-conducting channelrhodopsin, or fragment thereof, transgene be integrated into the chromosomal site of the endogenous copy of the mammalian anion-conducting channelrhodopsin gene, gene targeting is generally preferred. Briefly, when such a technique is to be utilized, vectors containing some nucleotide sequences homologous to the endogenous anion-conducting channelrhodopsin gene are designed for the purpose of integrating, via homologous recombination with chromosomal sequences, into and disrupting the function of the endogenous channelrhodopsin gene (i.e., "knock-out" animals). In this way, the expression of the endogenous channelrhodopsin gene may also be eliminated by inserting non-functional sequences into the endogenous channelrhodopsin gene. The transgene may also be selectively introduced into a particular cell-type, thus inactivating the endogenous channelrhodopsin gene in only that cell-type (see, e.g., Gu et al., *Science* 265:103-106, 1994). The regulatory sequences required for such a cell-type specific inactivation will depend upon the particular cell-type of interest, and will be apparent to those of skill in the art.

Any technique known in the art may be used to introduce a channelrhodopsin, or fragment thereof, transgene into animals to produce the founder lines of transgenic animals. Such techniques include, but are not limited to: pronuclear microinjection (U.S. Pat. No. 4,873,191); retrovirus-mediated gene transfer into germ lines (van der Putten et al., *Proc. Natl. Acad. Sci. USA* 82:6148-6152, 1985); gene targeting in embryonic stem cells (Thompson et al., *Cell* 56:313-321, 1989); electroporation of embryos (Lo, *Mol. Cell. Biol.* 3:1803-1814, 1983); sperm-mediated gene transfer (Lavitrano et al., *Cell* 57:717-723, 1989); and positive-negative selection, as described in U.S. Pat. No. 5,464,764. For a review of such techniques, see, e.g., Gordon, *Int. Rev. Cytol.* 115:171-229, 1989.

Once transgenic animals have been generated, the expression of the recombinant channelrhodopsin gene, or fragment thereof, may be assayed utilizing standard techniques. Initial screening may be accomplished by Southern blot analysis or PCR techniques to analyze animal tissues to assay whether integration of the channelrhodopsin transgene has taken place. The level of mRNA expression of the channelrhodopsin transgene in the tissues of the transgenic animals may also be assessed using techniques that include, but are not limited to, Northern blot analysis of cell-type samples obtained from the animal, in situ hybridization analysis, and RT-PCR. Samples of an algae derived channelrhodopsin-expressing tissue can also be evaluated immunocytochemically using antibodies selective for the channelrhodopsin transgene product.

D. Transgene Based Therapies

In certain embodiments the presently disclosed compositions and are used to improve optogenetic techniques and applications as well as can be used to aid in diagnosis, prevention, and/or treatment of neurologic disorders, such as but not limited to Parkinson's disease, as well as for ocular disorders.

In some embodiments, methods and compositions are used to identify and characterize multiple channelrhodopsins derived from algae. The cloning and expression of the rhodopsin domain of the channelrhodopsins and expression in mammalian cells demonstrates that these channelrhodopsins have improved characteristics that can be used for optogenetic applications as well as therapeutic agents.

For example, a disclosed method and composition may be used in, among other things, retinal gene therapy for mammals (as described in, among others, U.S. Pat. Nos. 5,827,702, 7,824,869 and US Patent Publication Number 20100015095 as well as in WIPO publications WO 2000/15822 and WO 1998/48097). A genetically engineered ocular cell is produced by contacting the cell with an exogenous nucleic acid under conditions in which the exogenous nucleic acid is taken up by the cell for expression. The exogenous nucleic acid is described as a retrovirus, an adenovirus, an adeno-associated virus or a plasmid. Retinal gene transfer of a reporter gene, green fluorescent protein (GFP), using a recombinant adeno-associated virus (rAAV) was demonstrated in normal primates (Bennett, J et al. 1999 *Proc. Natl. Acad. Sci. USA* 96, 9920-25). The rescue of photoreceptors using gene therapy in a model of rapid degeneration of photoreceptors using mutations of the RP65 gene and replacement therapy with the normal gene to replace or supplant the mutant gene (See, for example, US Patent Publication 2004/0022766) has been used to treat a naturally-occurring dog model of severe disease of retinal degenerations—the RPE65 mutant dog, which is analogous to human LCA. By expressing photosensitive membrane-channels or molecules in surviving retinal neurons of the diseased retina by viral based gene therapy method, the present invention may produce permanent treatment of the vision loss or blindness with high spatial and temporal resolution for the restored vision.

The nucleic acids sequences that encode an active portion of the presently disclosed anion-conducting channelrhodopsins, include but are not limited to the nucleic acid sequences that encode the rhodopsin domains identified in SEQ ID NOS: 1, 3 and 13 or the rhodopsin domain sequences of SEQ ID NO: 2.

In some embodiments, there is provided a method of modifying a target polynucleotide in a eukaryotic cell, such as a neuron. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in an insertion of one or more channelrhodopsin-encoding nucleotides in said target polynucleotide.

An exemplary DNA binding protein is an RNA guided DNA binding protein of a Type II CRISPR System. An exemplary DNA binding protein is a Cas9 protein. According to one aspect, an engineered Cas9-gRNA system is provided which enables RNA-guided genome cutting in a site specific manner, if desired, and modification of the genome by insertion of exogenous channelrhodopsin-encoding nucleic acids provided herein. The guide RNAs are complementary to target sites or target loci on the DNA. The guide RNAs can be crRNA-tracrRNA chimeras. The Cas9 binds at or near target genomic DNA. The one or more guide RNAs bind at or near target genomic DNA. The Cas9 cuts the target genomic DNA and exogenous donor DNA is inserted into the DNA at the cut site.

Accordingly, methods are directed to the use of a guide RNA with a Cas9 protein and an exogenous channelrhodopsin-encoding nucleic acid to multiplex insertions of exogenous channelrhodopsin-encoding nucleic acids into DNA within a cell expressing Cas9 by cycling the insertion of nucleic acid encoding the RNA and exogenous donor nucleic acid, expressing the RNA, colocalizing the RNA, Cas9 and DNA in a manner to cut the DNA, and insertion of the exogenous donor nucleic acid. The method steps can be cycled in any desired number to result in any desired number of DNA modifications.

In some embodiments, introduction and expression of channelrhodopsins, such as those described herein, in ocular neuronal cells, for example, impart light sensitivity to such retinas and restoring one or more aspects of visual responses and functional vision to a subject suffering from such degeneration. By restoring light sensitivity to a retina lacking this capacity, due to disease, a mechanism for the most basic light-responses that are required for vision is provided. In some embodiments, the functional domains of anion-conducting channelrhodopsins, such as GtACR1 and GtACR2 may be used to restore light sensitivity to the retinas that have undergone rod and cone degeneration by expressing the channelrhodopsin in inner retinal neurons in vivo. In some embodiments these channelrhodopsins may be introduced using techniques that include, but are not limited to, retinal implants, cortical implants, lateral geniculate nucleus implants, or optic nerve implants In some embodiments, the anion-conducting channelrhodopsins are inserted into the retinal neurons that survived after the rods and cones have died in an area or portion of the retina of a subject, using the transfer of nucleic acids, alone or within an expression vector. Such expression vectors may be constructed, for example, by introduction of the desired nucleic acid sequence into a virus system known to be of use for gene therapy applications, such as, but not limited to, AAV (e.g., AAV2), retroviruses and alike.

In some embodiments the anion-conducting channelrhodopsins may be inserted into retinal interneurons. These cells then can become light sensitive and send signals via the optic nerve and higher order visual pathways to the visual cortex where visual perception occurs, as has been demonstrated electrophysiologicly in mice. In some embodiments, among other routes, intravitreal and/or subretinal injections may be used to deliver channelrhodopsin molecules or virus vectors expressing the same.

In some embodiments, the active portion of the presently disclosed algal derived anion-conducting channelrhodopsins, such as but not limited to the rhodopsin domain of these anion-conducting channelrhodopsins, can be used to restore light sensitivity to a retina, by delivering to retinal neurons a nucleic acid expression vector that encodes algal derived anion-conducting channelrhodopsins (such as but not limited to the rhodopsin domain of these anion-conducting channelrhodopsins) that is expressible in the neurons, which vector comprises an open reading frame encoding the rhodopsin, and operatively linked thereto, a promoter sequence, and optionally, transcriptional regulatory sequences; and expressing the vector in the neurons, thereby restoring light sensitivity.

In certain embodiments the channel rhodopsin can be algal derived anion-conducting channelrhodopsins such as, but not limited to functional domains of anion-conducting channelrhodopsins, such as, but not limited to, GtACR1, GtACR2 or Gt161302 or a biologically active fragment or conservative amino acid substitution variant thereof, such as but not limited to the rhodopsin domain. The vector system may be recombinant AAV (e.g., AAV2), the promoter may be a constitutive promoter such as, but not limited to, a CMV promoter or a hybrid CMV enhancer/chicken β-actin promoter (CAG).

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Molecular Biology Methods:

Sequences encoding 7TM domains of *G. theta* opsins (295, 291 and 288 aa, corresponding to the JGI protein models 111593, 146828 and 161302, respectively) were optimized for human codon usage and were synthesized (Genewiz, South Plainfield, N.J., USA) and cloned into the mammalian expression vector pcDNA3.1 (Life Technologies, Grand Island, N.Y., USA) in frame with an EYFP tag. The sequence information encoding the functional constructs 111593 (GtACR1) and 146828 (GtACR2) were deposited in GenBank (accession numbers KP171708 and KP171709, respectively). The gene encoding archaerhodopsin-3 (Arch) was kindly provided by Dr. Edward S. Boyden (Massachusetts Institute of Technology, Boston, Mass., USA). Mutations were introduced using a QuikChange XL site-directed mutagenesis kit (Agilent Technologies, Santa Clara, Calif., USA) and verified by DNA sequencing.

measured at 150 mM $NMG^+$ in the bath from the values measured at 150 mM $Na^+$ (pH 5.4), 150 mM $Na^+$ (pH 7.4), 150 mM $K^+$ (pH 7.4) or 75 mM $Ca^{2+}$ (pH 7.4). The $Cl^-$ concentration in the bath was 155.6 mM with all cations. In tests of anion permeability $E_{rev}$ shifts were calculated by subtraction of the Reference value measured at 150 mM $Asp^-$ from the value measured at 75 mM $SO_4^{2-}$ or 150 mM of $F^-$, $Br^-$, $I^-$ or $NO3^-$. The $Na^+$ concentration in the bath was 150 mM with all anions except F- (Table 1).

TABLE 1

Composition of pipette and bath solutions and liquid junction potentials in experiments with HEK293 cells.

| | NaCl | KCl | CaCl$_2$ | MgCl$_2$ | Na$_2$EGTA | HEPES | NMG | Glucose | NaAsp | NaF | NaBr | NaI | NaNO$_3$ | Na$_2$SO$_4$ | HCl | LJP pip. stand | LJP pip. Asp |
|---|---|---|---|---|---|---|---|---|---|---|---|---|---|---|---|---|---|
| Pipette standard | — | 126 | 0.5 | 2 | 5 | 25 | 12.2 | — | — | — | — | — | — | — | — | — | — |
| Pipette Asp | — | — | 0.5 | 2 | 5 | 25 | 12.2 | — | 126 | — | — | — | — | — | — | — | — |
| Bath standard | 150 | — | 1.8 | 1 | — | 10 | 4.6 | 5 | — | — | — | — | — | — | — | 4.7 | 12.9 |
| Bath Asp | — | — | 1.8 | 1 | — | 10 | 4.6 | 5 | 150 | — | — | — | — | — | — | -7 | — |
| Bath pH 5.4 | 150 | — | 1.8 | 1 | — | 10 | — | 5 | — | — | — | — | — | — | — | 4.7 | — |
| Bath K | — | 150 | 1.8 | 1 | — | 10 | 4.6 | 5 | — | — | — | — | — | — | — | 0.3 | — |
| Bath Ca | — | — | 75 | 1 | — | 10 | 4.6 | 5 | — | — | — | — | — | — | — | 8.4 | — |
| Bath NMG | 1.5 | — | 1.8 | 1 | — | 10 | 148.5 | 5 | — | — | — | — | — | — | 148.5 | 10.7 | — |
| Bath F | 5.6 | — | — | — | — | 10 | 4.6 | 5 | — | 150 | — | — | — | — | — | 13.8 | — |
| Bath Br | — | — | 1.8 | 1 | — | 10 | 4.6 | 5 | — | — | 150 | — | — | — | — | 4.5 | — |
| Bath I | — | — | 1.8 | 1 | — | 10 | 4.6 | 5 | — | — | — | 150 | — | — | — | 4.3 | — |
| Bath NO$_3$ | — | — | 1.8 | 1 | — | 10 | 4.6 | 5 | — | — | — | — | 150 | — | — | 3.3 | — |
| Bath SO$_4$ | — | — | 1.8 | 1 | — | 10 | 4.6 | 5 | — | — | — | — | — | 75 | — | -2.6 | — |

Abbreviations used:
Asp, aspartate;
EGTA, ethylene glycol tetraacetic acid;
HEPES, 4-(2-hydroxyethyl)-1-piperazineethanesulfonic acid;
LJP, liquid junction potential;
NMG, N-Methyl-D-glucamine.
All concentrations are in mM.

HEK293 Recording Methods:

HEK293 (human embryonic kidney) cells were transfected using the ScreenFectA transfection reagent (Waco Chemicals USA, Richmond, Va., USA). All-trans-retinal (Sigma, St Louis, Mo., USA) was added as a stock solution in ethanol at the final concentration of 5 µM. Measurements were performed 48-72 h after transfection with an Axopatch 200B amplifier (Molecular Devices, Union City, Calif., USA). The signals were digitized with a Digidata 1440A using pClamp 10 software (both from Molecular Devices). Patch pipettes with resistances of 2-5 MΩ were fabricated from borosilicate glass. The composition of solutions is shown in table 51. A 4 M salt bridge was used in all experiments; liquid junction potentials (LJP) were calculated using the ClampEx built-in LJP calculator. Continuous light pulses were provided by a Polychrome IV light source (T.I.L.L. Photonics GMBH, Grafelfing, Germany) in combination with a mechanical shutter (Uniblitz Model LS6, Vincent Associates, Rochester, N.Y., USA; half-opening time 0.5 ms). The light intensity was attenuated with the built-in Polychrome system or with neutral density filters. Maximal quantum density at the focal plane of the 40× objective lens was 8.5 mW/mm$^2$.

In experiments aimed to test cation permeability Erev shifts were calculated by subtraction of the reference value Neuronal Recording:

For neuronal expression the GtACR2-EYFP construct was transferred to the pFUGW lentivirus vector provided by Dr. Carlos Lois (Massachusetts Institute of Technology, Boston, Mass., USA). The lentivirus was produced by triple transfection of HEK293FT cells (Invitrogen Grand Island, N.Y., USA) with the envelope plasmid pCMV-VSVG, the packaging plasmid pΔ8.9 (both from Dr. Lois) and the pFUGW-GtACR2-EYFP plasmid using Lipofectamine 2000 (Invitrogen, Grand Island, N.Y., USA). Hippocampi of E18 Sprague Dawley rats were obtained as part of a kit from BrainBits (Springfield, Ill., USA), and primary neuronal cultures were prepared using the protocol provided by the company. Cells were cultured in NbActiv4 medium on poly-lysine coated coverslips and supplemented with 0.4 µM all-trans retinal (final concentration, in addition to retinyl acetate present in the medium). Patch-clamp measurements were carried out 10 to 19 days after transfection. The same photoexcitation source and measuring setup was used as described above for HEK cells. Spiking was measured in the current clamp mode. The composition of solutions is shown in Table 2.

TABLE 2

Composition of pipette and bath solutions and liquid junction potentials in experiments with neurons.

| | $K_2SO_4$ | KCl | NaCl | $CaCl_2$ | $MgCl_2$ | HEPES | Glucose | LJP |
|---|---|---|---|---|---|---|---|---|
| Pipette | 67.5 | — | — | — | 2 | — | — | — |
| Bath Tyrode | — | 2 | 125 | 3 | 1 | 25 | 30 | 11.3 |

Abbreviations used:
HEPES, 4-(2-hydroxyethyl)-1-piperazineethanesulfonic acid;
LJP, liquid junction potential;
NMDG, N-Methyl-D-glucamine.
All concentrations are in mM.

Example 2—Characterization of Rhodopsins

Of the approximately 50 known ChRs from chlorophytes, all that have been tested are exclusively cation channels. However, several rhodopsin sequences that have been cloned from these organisms did not exhibit channel activity. The nuclear genome sequence of the cryptophyte *Guillardia theta* has been completely sequenced (B. A. Curtis et al., Nature 492, 59 (2012)). A BLAST search of model proteins returned 53 hits with homology to microbial (type I) rhodopsins. None were highly homologous to ChRs, but the models of one particular cluster (FIG. 1A) do contain some key residues characteristic of chlorophyte ChRs (FIG. 1B).

The sequences encoding the 7TM domains of *G. theta* proteins 111593, 146828 and 161302 were well expressed in HEK293 cells. The first two constructs generated photocurrents, whereas the third did not. As shown below, the first two function as light-gated anion channels; therefore we named them GtACR1 and GtACR2 (*Guillardia theta* Anion Channel Rhodopsins 1 and 2).

Figures 1C, 1D:
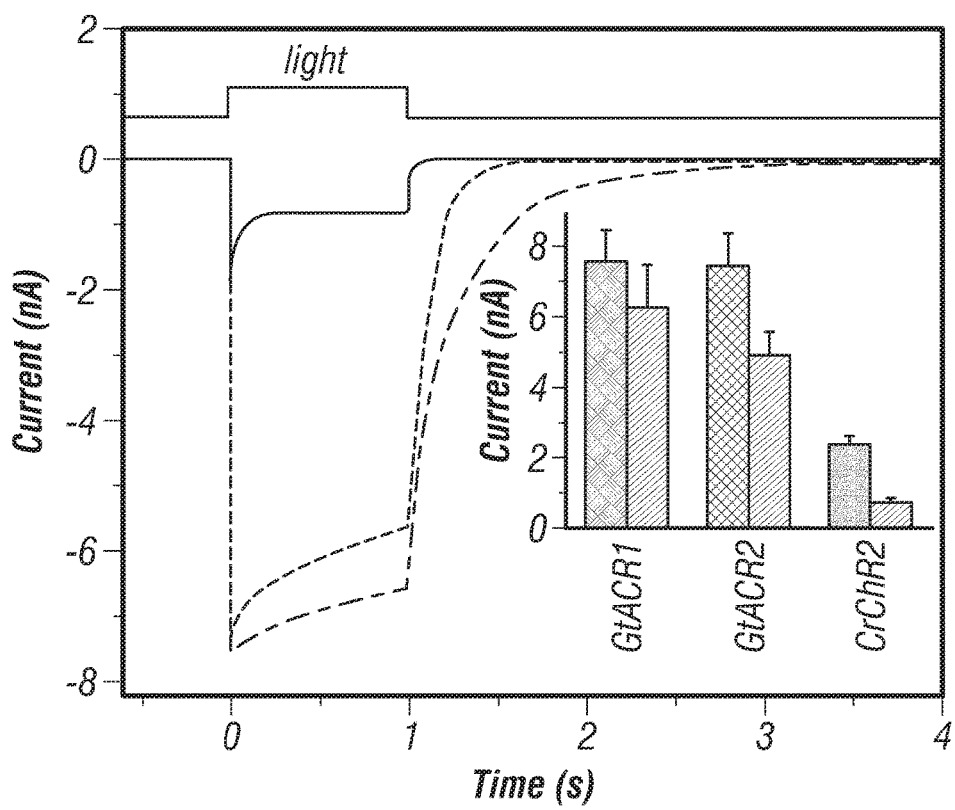
Figure 1E:
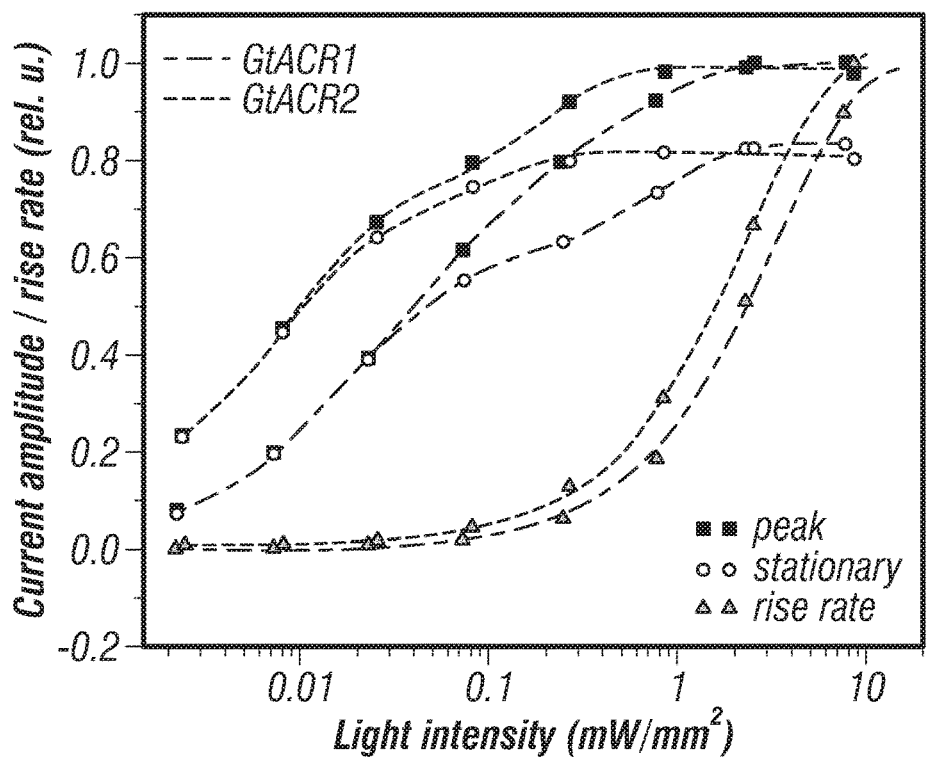
Figure 1F:
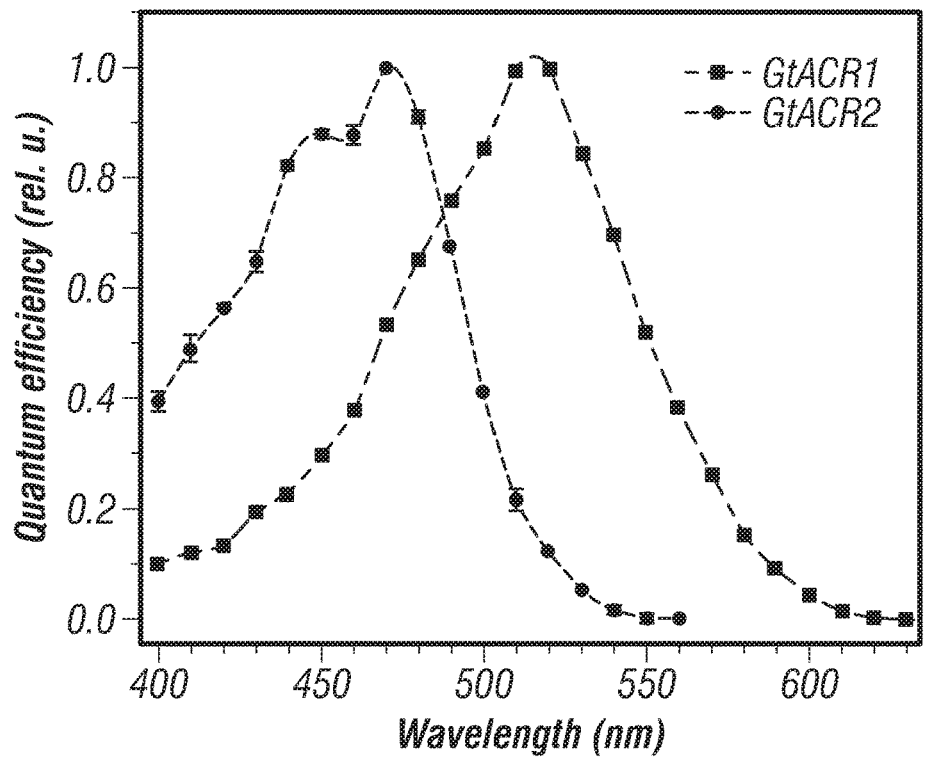

Using standard solutions (126 mM KCl in the pipette and 150 mM NaCl in the bath, pH 7.4; for other components Table 1) the currents generated by GtACR1 and GtACR2 were inward at the holding potential ($E_h$) −60 mV (FIG. 1D, main figure). The mean stationary currents from GtACR1 and GtACR2 were, respectively, 8- and 6-fold larger than those from CrChR2, the most frequently used optogenetic tool, with significantly smaller inactivation (FIG. 1, inset). Half-decay times of photocurrents were 200 and 90 ms for GtACR1 and GtACR2, respectively. The dependence of the current rise rate on the stimulus intensity exhibited a higher saturation level than the amplitude (FIG. 1E) and therefore was used for construction of the action spectra. GtACR1 showed maximal sensitivity to 515 nm light with a shoulder on the short-wavelength slope of the spectrum (FIG. 1F). The sensitivity of GtACR2 peaked at 470 nm with additional bands at 445 and 415 nm (FIG. 1F).

Figure 2A:
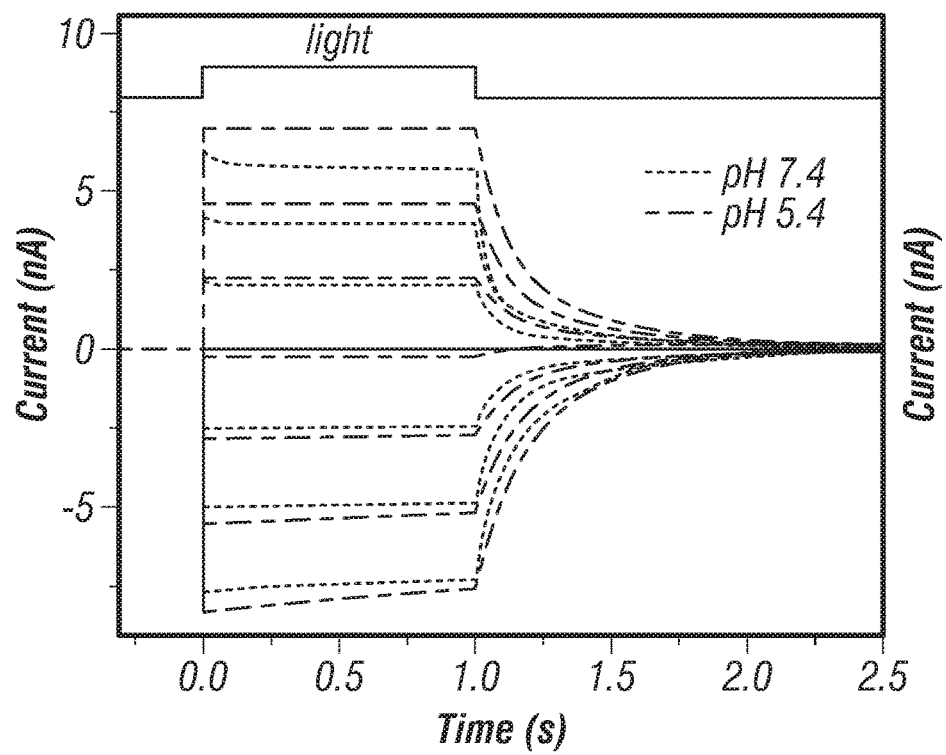
FIG. 2A-D: ACRs do not conduct cations. Photocurrents generated by GtACR1 (A) and GtACR2 (B) in HEK293 cells at $E_h$ changed in 20-mV steps from −60 mV (bottom to top; for liquid junction potentials (LJP) values (Table 1). The pipette solution was standard, whereas the bath solution was as indicated. (C) Current-voltage relationships measured at different pH of the bath. The data (mean values±SEM, n=4-6 cells) were corrected for LJP and normalized to the value measured at −60 mV at pH 7.4. Representative data for CrChR2 are shown for comparison. (D) $E_{rev}$ shifts measured upon variation of the cation composition of the bath. The data are mean values±SEM (n=3-6 cells).
Figure 2B:
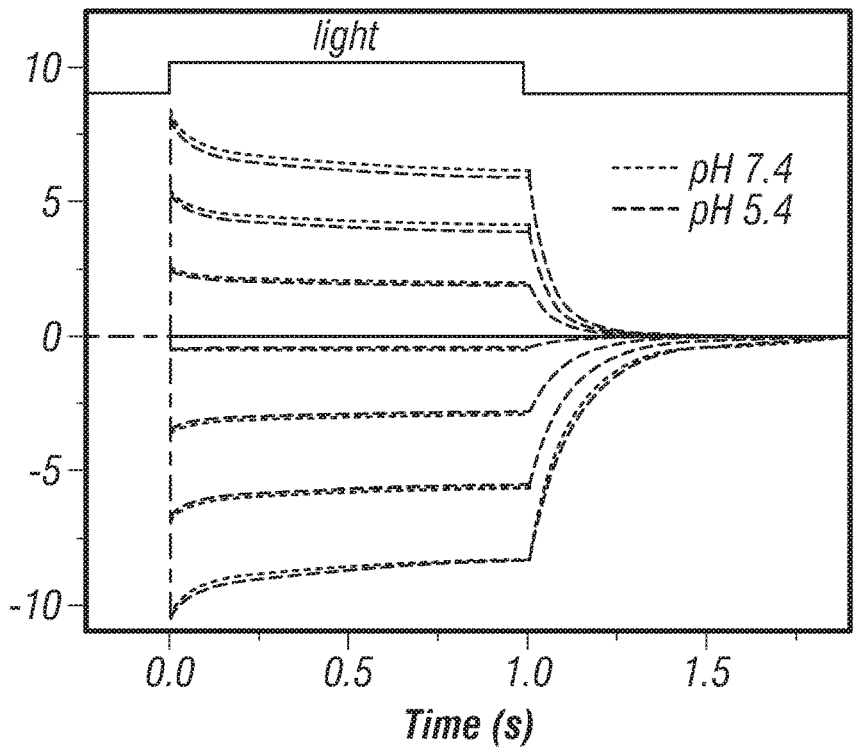
Figure 2C:
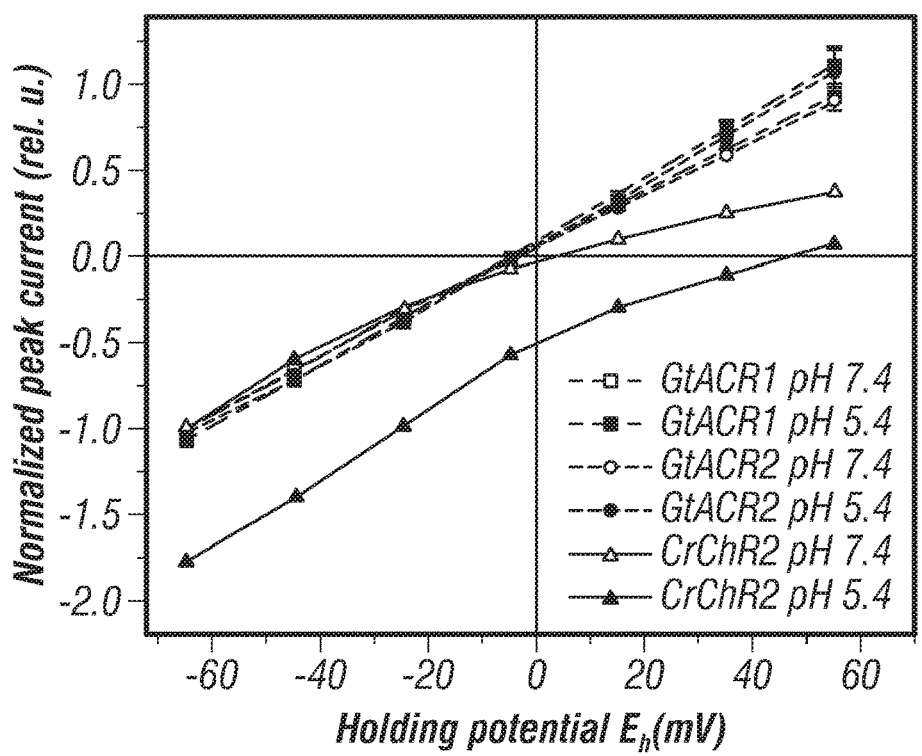
Figure 2D:
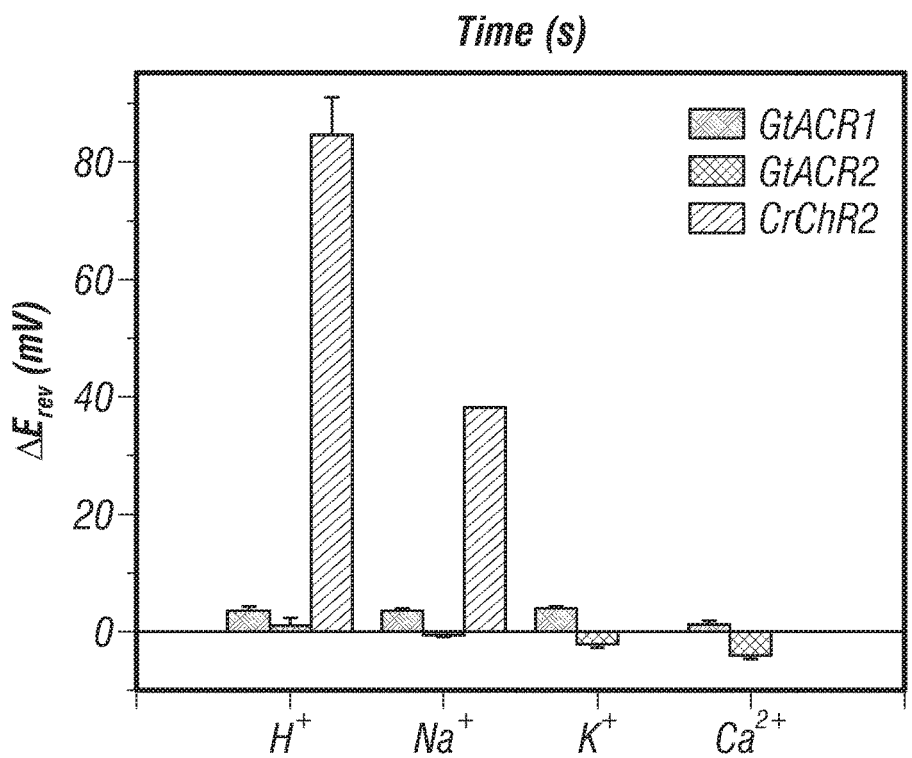

Using standard solutions (see above) the sign of GtACR1 and GtACR2 photocurrents reversed upon membrane depolarization (FIGS. 2A and B, respectively). In the tested range from −60 to 60 mV the current voltage relationships (IE curves) were linear (FIG. 2C), unlike those for chlorophyte ChRs (described in D. Gradmann, A. Berndt, F. Schneider, P. Hegemann, *Biophys. J.* 101, 1057 (2011). To characterize the ion permeability of *G. theta* rhodopsins IE curves were measured and determined $E_{rev}$ upon variation of the ionic composition of the bath solution. In contrast to chlorophyte ChRs, for which protons are the most highly permeant ions, $E_{rev}$ of the currents generated by GtACR1 and GtACR2 were not affected by pH (FIG. 2C). Moreover, no $E_{rev}$ shifts were observed when the large non-permeable organic cation N-methyl-glucamine ($NMG^+$) was replaced with $Na^+$, $K^+$, or $Ca^{2+}$ (FIG. 2D). Indicating that GtACR1 and GtACR2 are not permeable to cations conducted by chlorophyte ChRs.

Figure 3A:
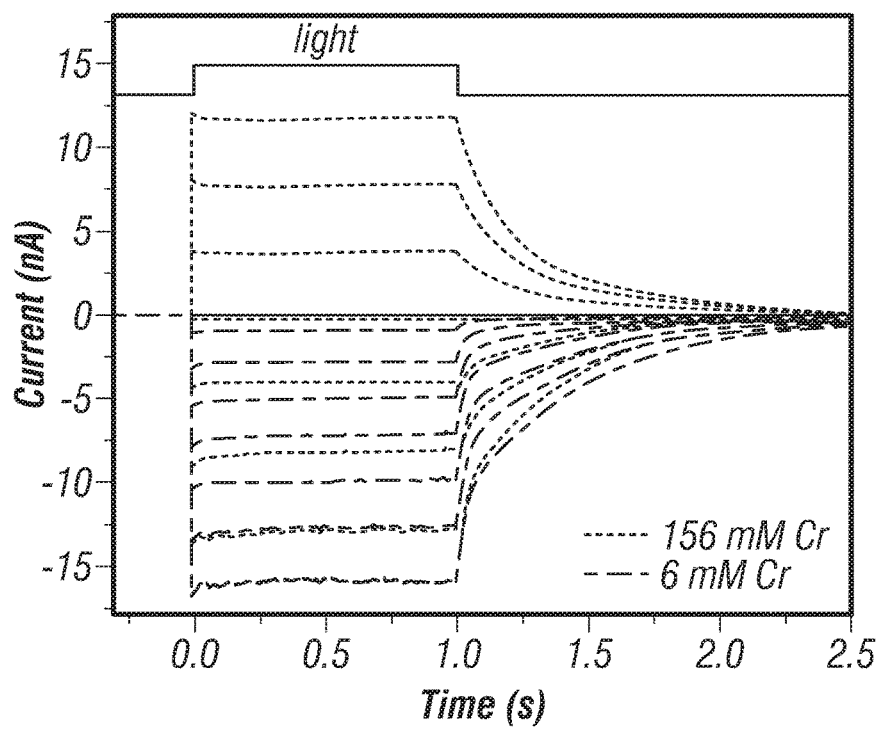
FIG. 3A-D: Anion selectivity of ACRs. Photocurrents generated by GtACR1 (A) and GtACR2 (B) in HEK293 cells at $E_h$ changed in 20-mV steps from −60 mV (bottom to top; for liquid junction potential (LJP) values (Table 1). The pipette solution was standard, whereas the bath solution was as indicated. (C) Current-voltage relationships measured at different Cl⁻ concentrations in the bath. The data (mean values±SEM, n=4-6 cells) were corrected for LJP and normalized to the value measured at −60 mV at 156 mM Cl⁻. The dashed vertical lines show the Nernst equilibrium potential for Cl⁻ at the bath concentrations used. (D) $E_{rev}$ shifts measured upon variation of the anion composition of the bath. The data are mean values±SEM (n=3-6 cells).
Figure 3B:
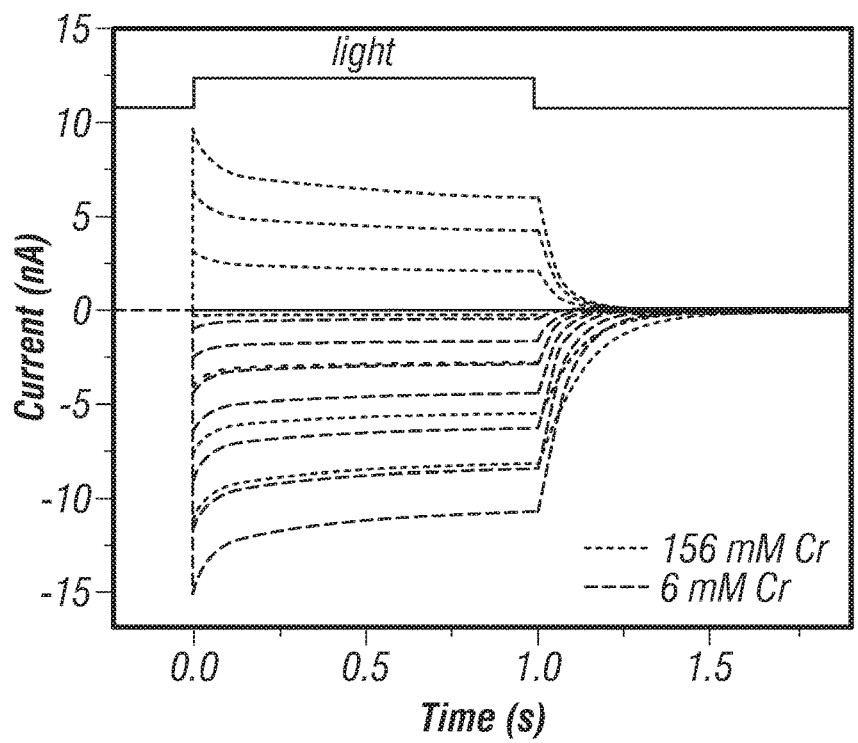
Figure 3C:
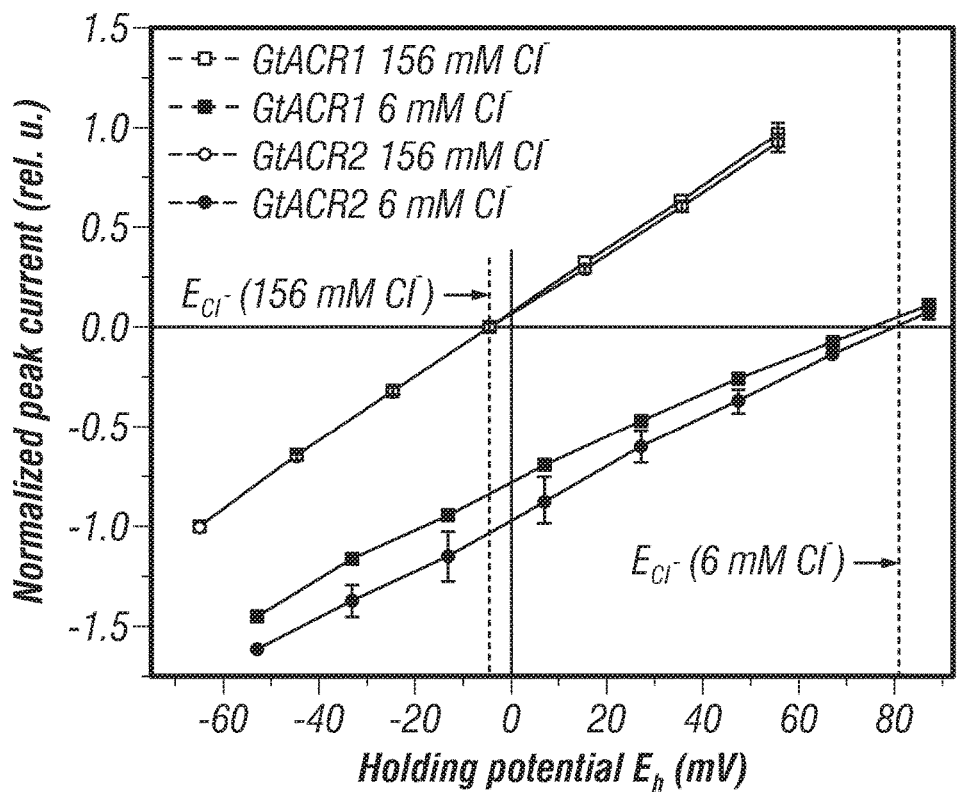
Figure 3D:
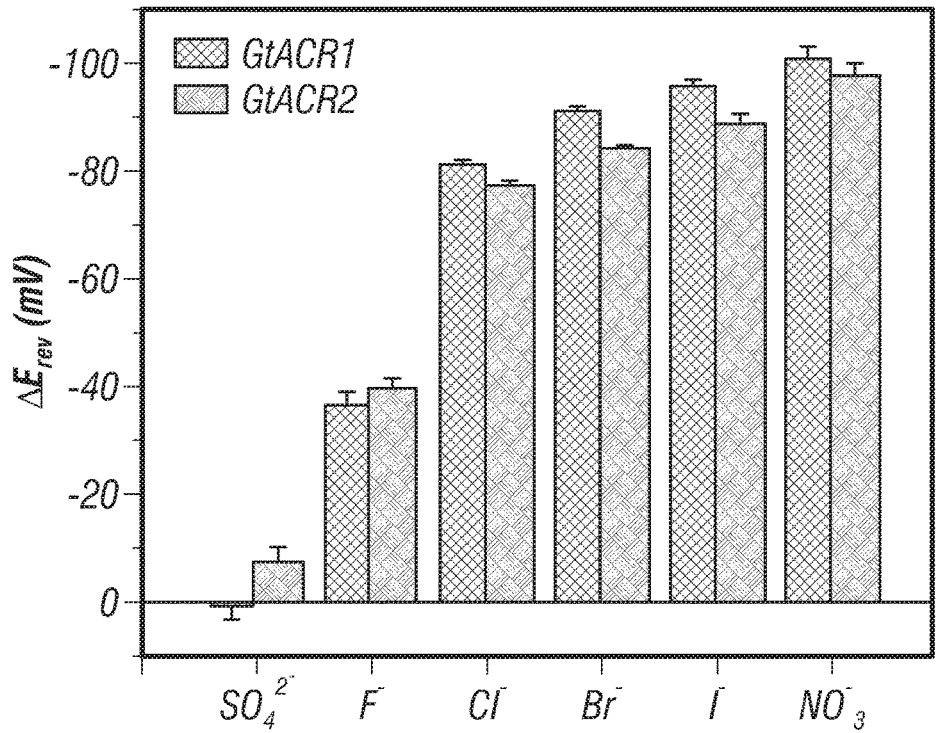

When most of the $Cl^-$ in the bath was replaced with the large organic anion aspartate yielding a Nernst equilibrium potential for $Cl^-$ ($E_{Cl}$) of 81 mV, $E_{rev}$ shifted to 80 mV (FIGS. 3A-C), as would be expected only if the currents generated by the GtACR1 and GtACR2 were exclusively due to passive $Cl^-$ transport. Next, we compared permeabilities of different anions by substituting them for non-permeable $Asp^-$ in the bath. For both *G. theta* ACRs, $I^-$, $NO3^-$, or $Br^-$ caused even greater $E_{rev}$ shifts than $Cl^-$. $F^-$ caused a smaller shift, whereas $SO_4^{2-}$— was non-permeable. The permeability sequence $NO3^->I^->Br^->Cl^->F^->SO_4^{2-}=Asp^-$ determined for ACRs is in accord with the lyotropic series characteristic of many classic $Cl^-$ channels from animal cells.

Figure 6A:
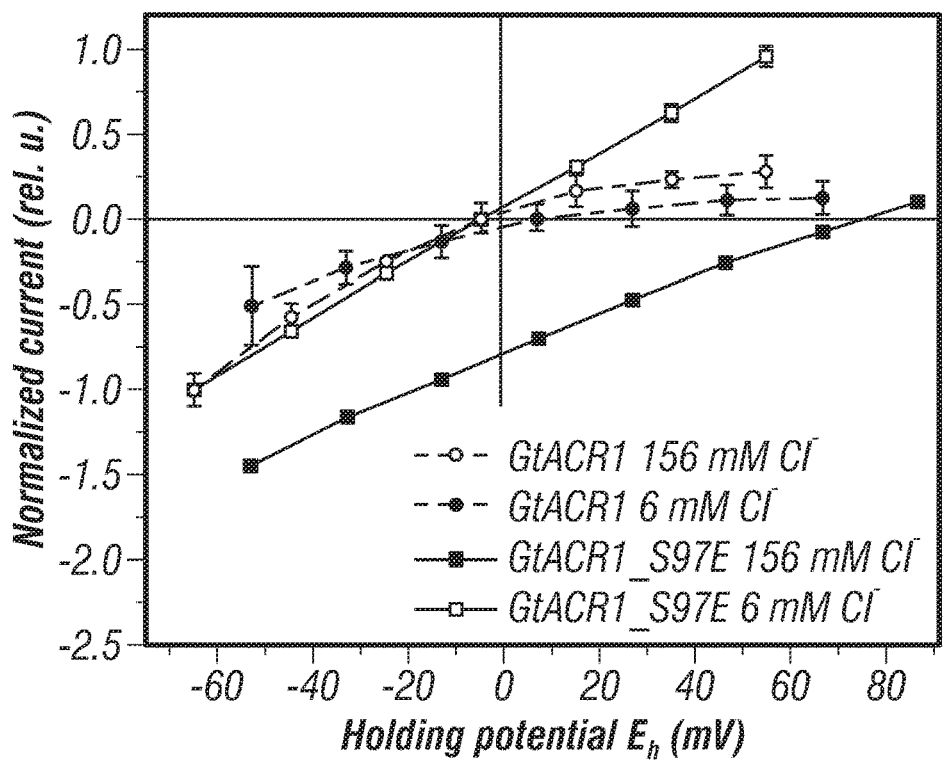
FIG. 6A-B: Current-voltage relationships for GtACR1 measured at different concentrations in the bath. (A) The data (mean values±SEM, n=4-6 cells) were for liquid junction potentials and normalized to the value measured at −60 mV at 156 mM Cl−. The dashed vertical lines show the Nernst equilibrium potential for Cl− at the bath concentrations used. (B) Photocurrents generated by GtACR1 (FIG. 6B) in HEK293 cells with low Cl concentration in the pipette and high Cl concentration in the bath The membrane potentials were changed in 20-mV steps from −80 mV at the amplifier output.

A conspicuous feature of ACRs is a non-carboxylic residue in the position of the proton acceptor Asp85 in bacteriorhodopsin (BR), where nearly all cation-selective ChRs contain a Glu residue (column 5 of helix 3, highlighted red in FIG. 1C). Its replacement with Glu reduced the currents >1000-fold without inhibiting expression. The kinetics of these very small remaining currents changed dramatically. But most importantly, this mutation eliminated anion selectivity of ACRs, as was evident from the practically unchanged $E_{rev}$ after replacement of chloride with aspartate in the bath (FIG. 6A), in a dramatic contrast to the wild type. Therefore, the absence of a carboxylate residue in the proton acceptor position appears to be required for anion selectivity of ACRs. A non-ionizable residue at the corresponding position is also typical of chloride-pumping rhodopsins from haloarchaea and marine flavobacteria (FIG. 1C), where the residue forms part of the chloride binding site in the unphotolyzed state as shown for haloarchaeal halorhodopsin.

Figure 4A:
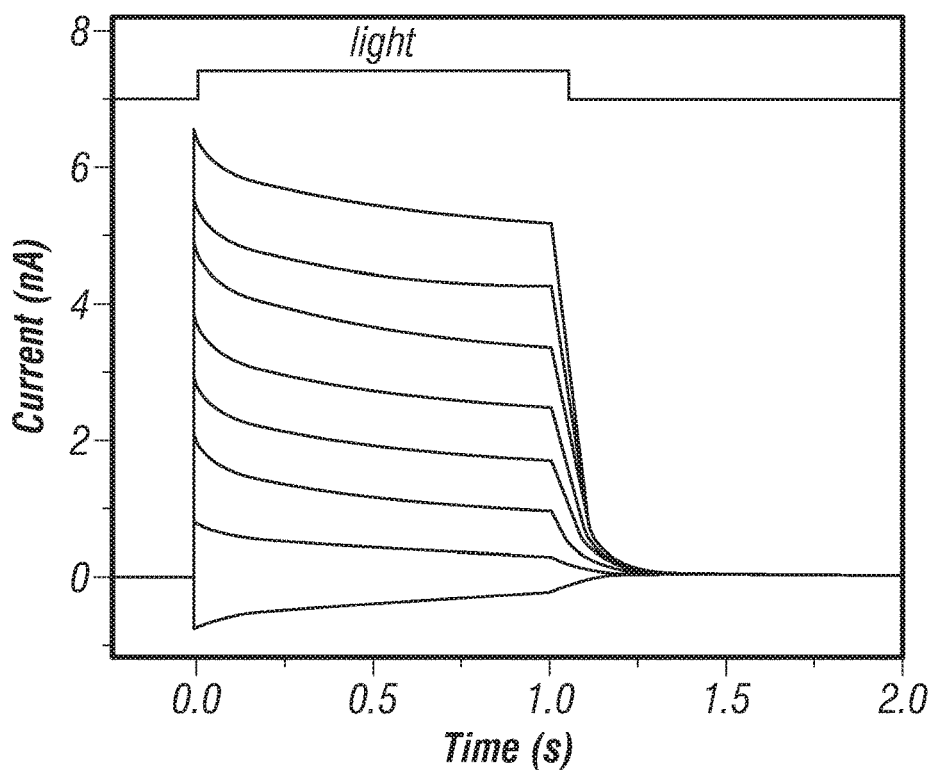
FIG. 4A-F: GtACR2 as a hyperpolarizing tool. (A and C) Photocurrents generated by GtACR2 in HEK293 cells (A) and in cultured pyramidal neurons (C) with low Cl⁻ concentration in the pipette and high Cl⁻ concentration in the bath at En changed in 20-mV steps from −80 mV (bottom to top; for LJP values (Tables 1 and 2). (B) Light intensity dependence of photocurrents generated by GtACR2 and archaerhodopsin-3 (Arch) in HEK293 cells at 20 mV. The data for slow Cl⁻-conducting ChR mutants are from J. Wietek et al., (2014) ibid and A. Berndt, et al., (2014) ibid. The arrows show the difference in light sensitivity. (D) Current-voltage relationship measured in neurons as shown in (C). The data (mean values±SEM, n=5 cells) were corrected for LJP (Table 2). The dashed vertical line shows the resting potential (Erest). The data for Cl⁻-conducting ChR mutants are from J. Wietek et al., (2014) ibid and A. Berndt, et al., (2014) ibid. (E) Photoinhibition of spiking induced by pulsed (10 ms, 10 kHz) current injection in a neuron expressing GtACR2. The light intensity was 8.5E-3 mW/mm². (F) Light intensity dependence of electrically evoked spikes. The difference in the amplitude between electrically evoked signals in the dark and light was calculated as shown.
Figure 4B:
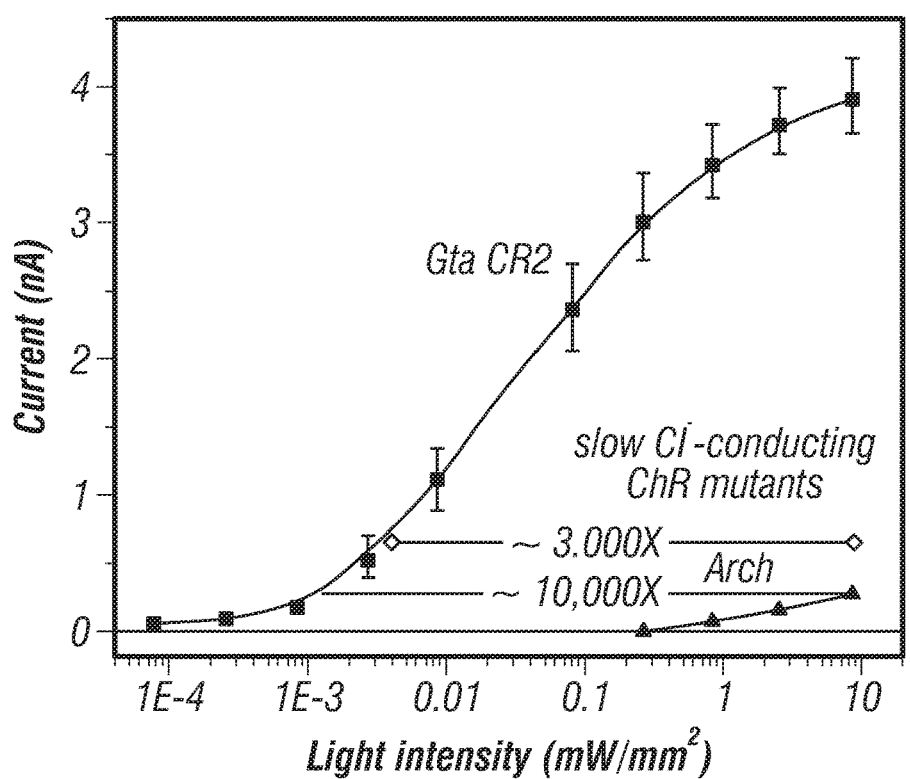
Figure 6B:
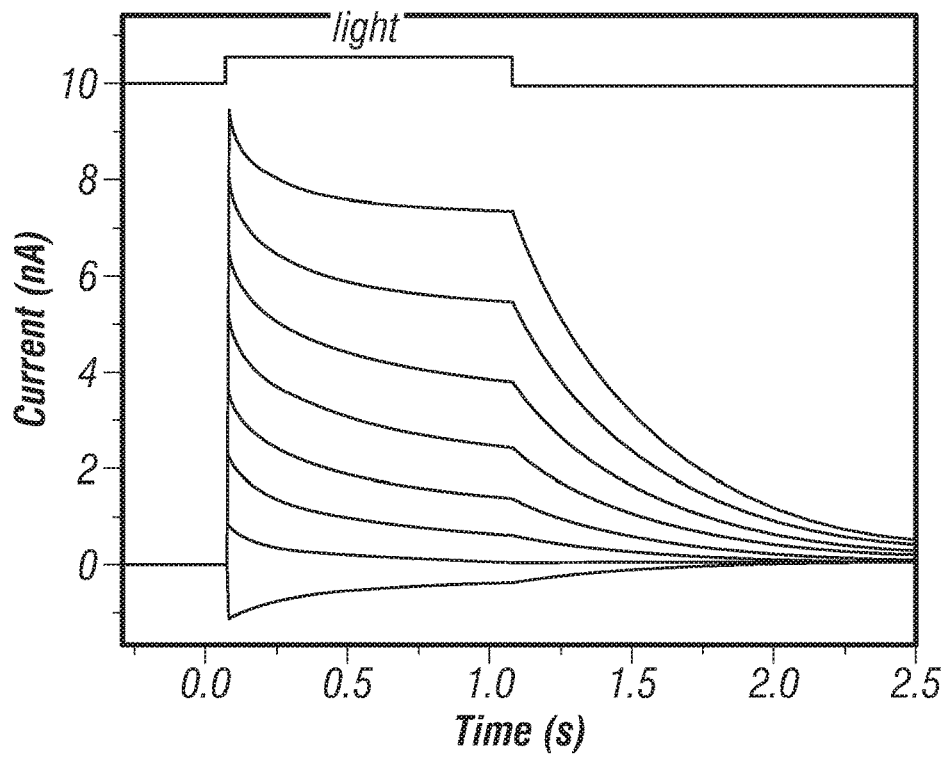

The cytoplasmic $Cl^-$ concentration in most animal cells including neurons is low. Under such conditions (6 mM of $Cl^-$ in the pipette and 156 mM in the bath) *G. theta* ACRs generated hyperpolarizing currents in HEK293 cells at $E_h$ above $E_{Cl}$ (FIG. 4A for GtACR2, FIG. 6B for GtACR1). The amplitude of GtACR2 photocurrents was similar, but the kinetics was faster than of GtACR1 currents, which is advantageous for control of neuronal activity. The high amplitude of the photocurrents makes ACRs very promising as optogenetic tools for light-induced hyperpolarization. GtACR2 generated hyperpolarizing photocurrents of the same amplitude as the proton pump archaerhodopsin-3 (Arch), a popular tool for optogenetic spike suppression, at 10,000-fold lower light intensity (FIG. 4B). The maximal amplitude of hyperpolarizing photocurrents of the most efficient $Cl^-$-conducting ChR mutants was <0.6 nA at the expense of dramatically slower kinetics. With GtACR2 the currents of such amplitude and 100-fold faster kinetics were observed at 3000-fold lower light intensity (FIG. 4B). These properties make *G. theta* ACRs more efficient hyperpolarizing optogenetic tools than previously available.

Figure 4C:
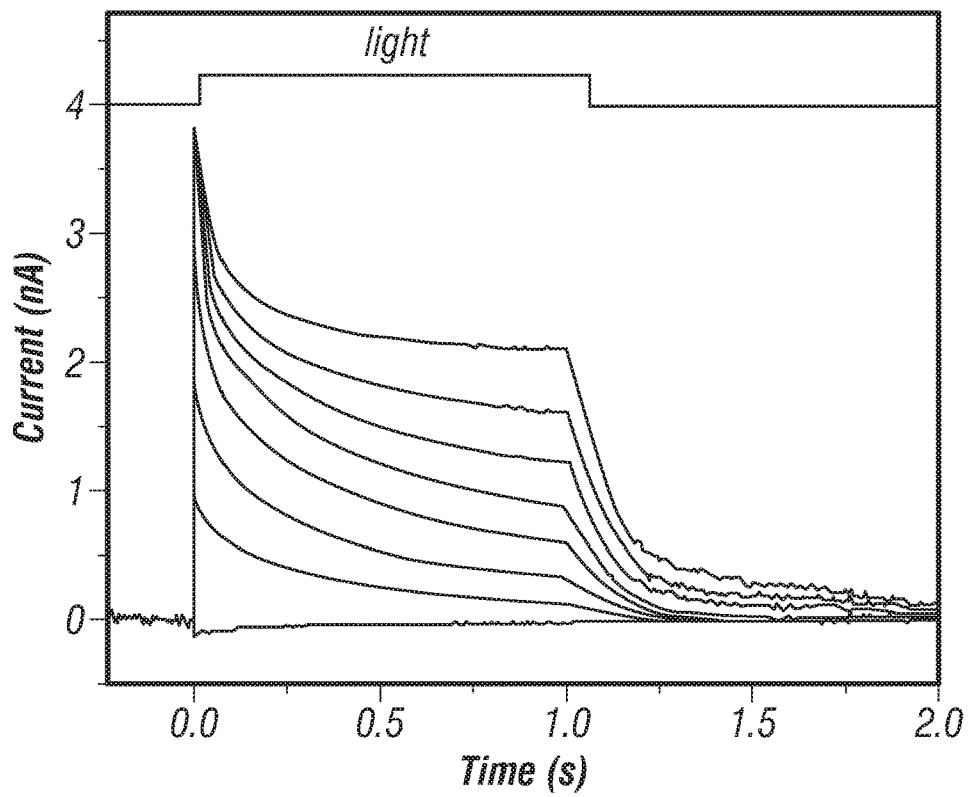
Figure 4D:
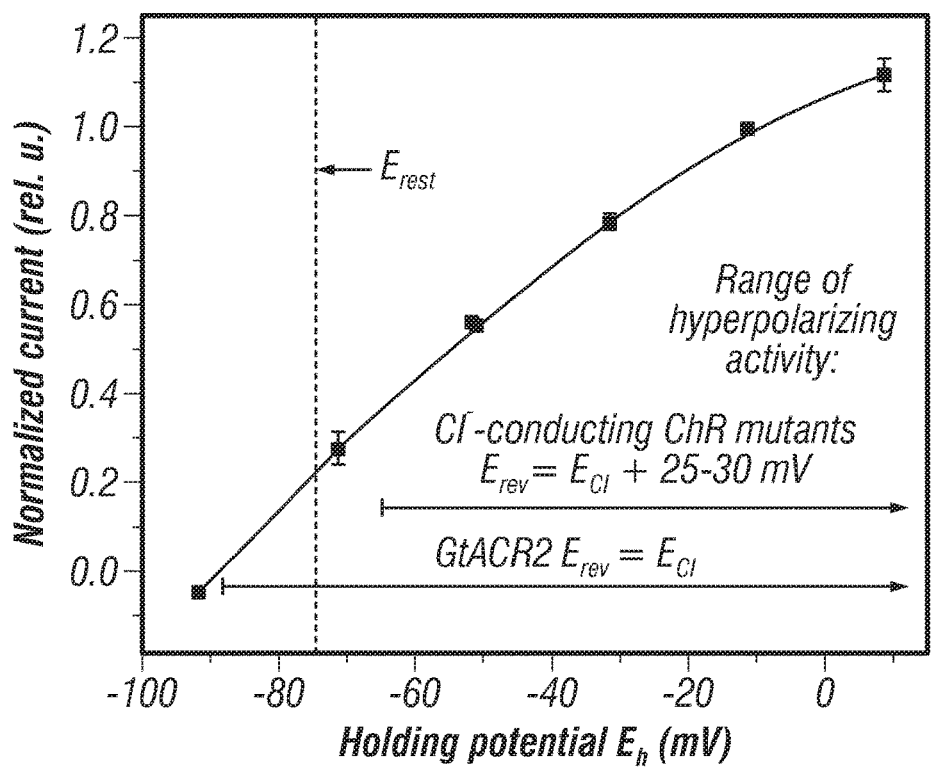
Figure 4E:
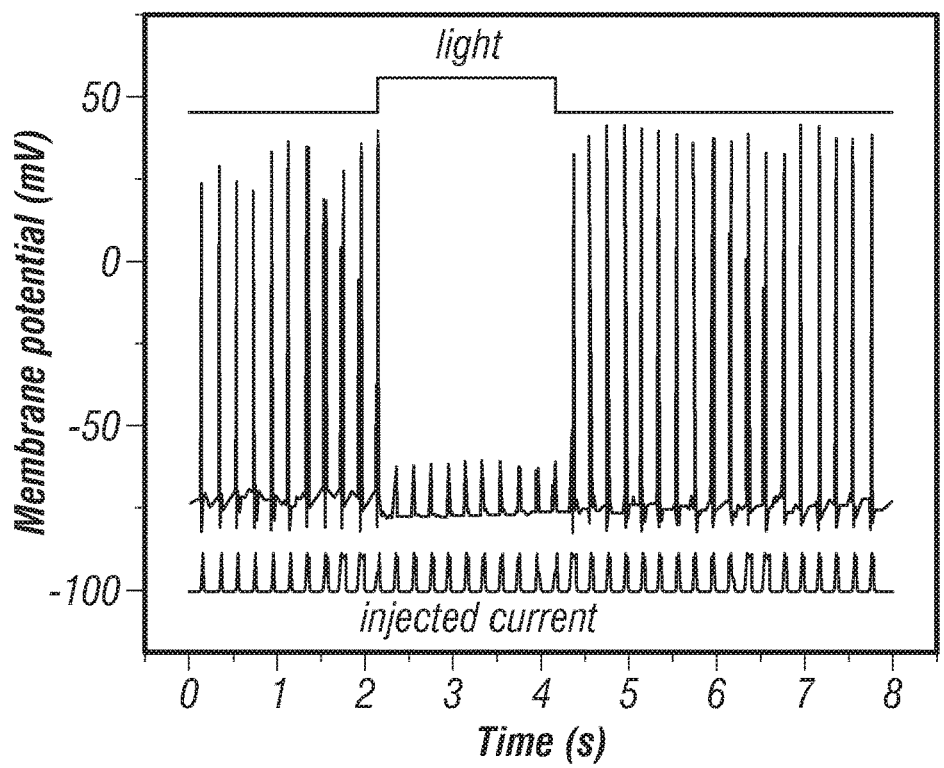
Figure 4F:
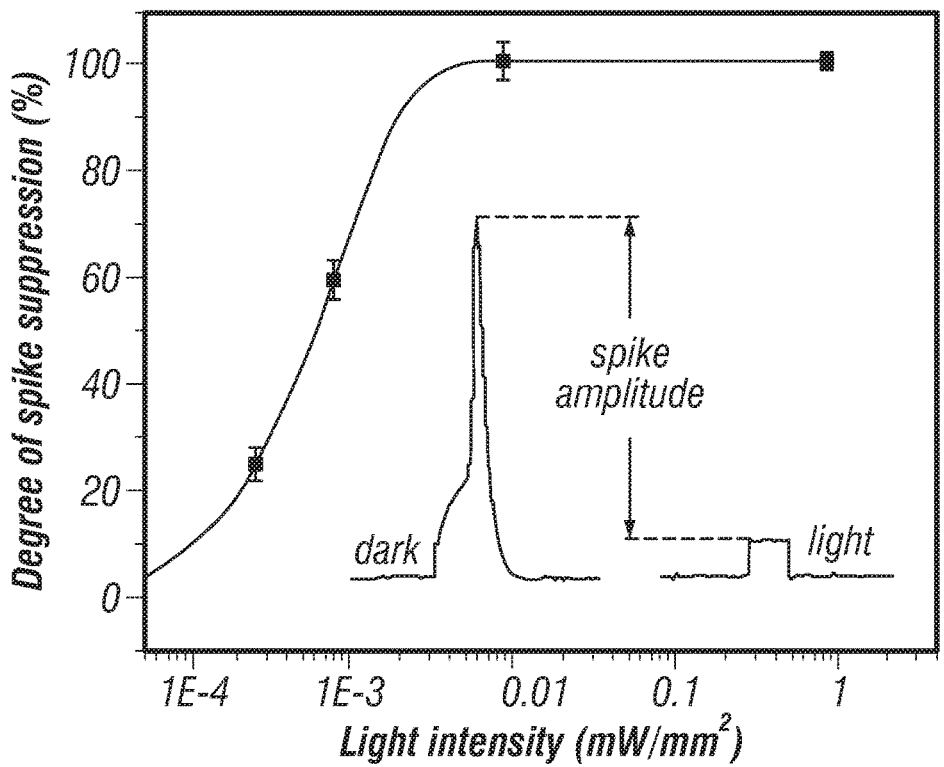
Figure 5:
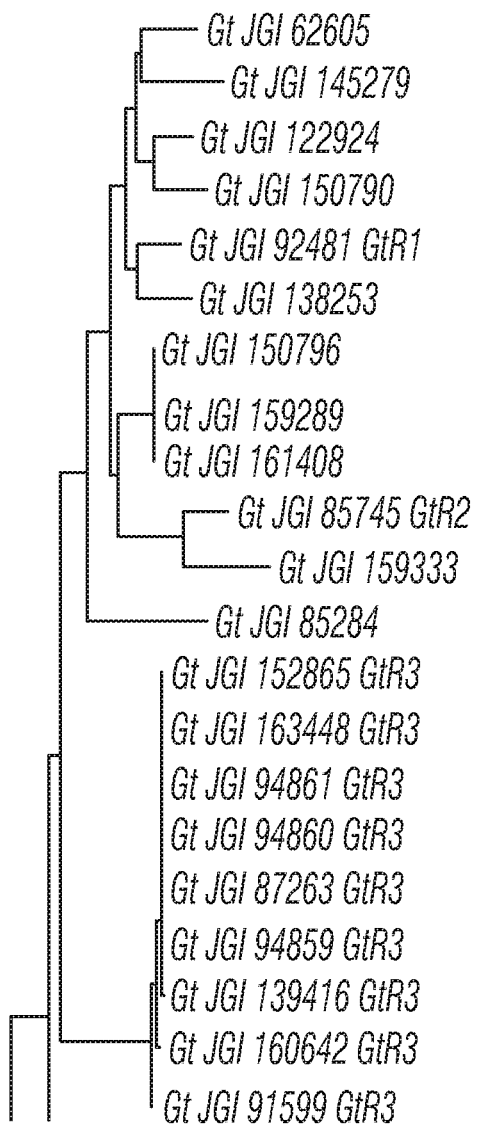
FIG. 5: Phylogenetic tree of *G. theta* protein models. The models homologous to microbial rhodopsins were selected among those predicted by the Joint Genome Institute (JGI) sequencing project (see the world wide web at: genome.jgi-.doe.gov/Guith1/Guith1.home.html) and aligned using ClustalW. The tree was constructed using the neighbor-joining method. GtR1, GtR2 and GtR3 are proteins identified previously. Eight models lack the conserved Lys residue in the seventh transmembrane helix that covalently links to retinal in known rhodopsins, and should therefore be considered opsin-related proteins.
Figure 5:
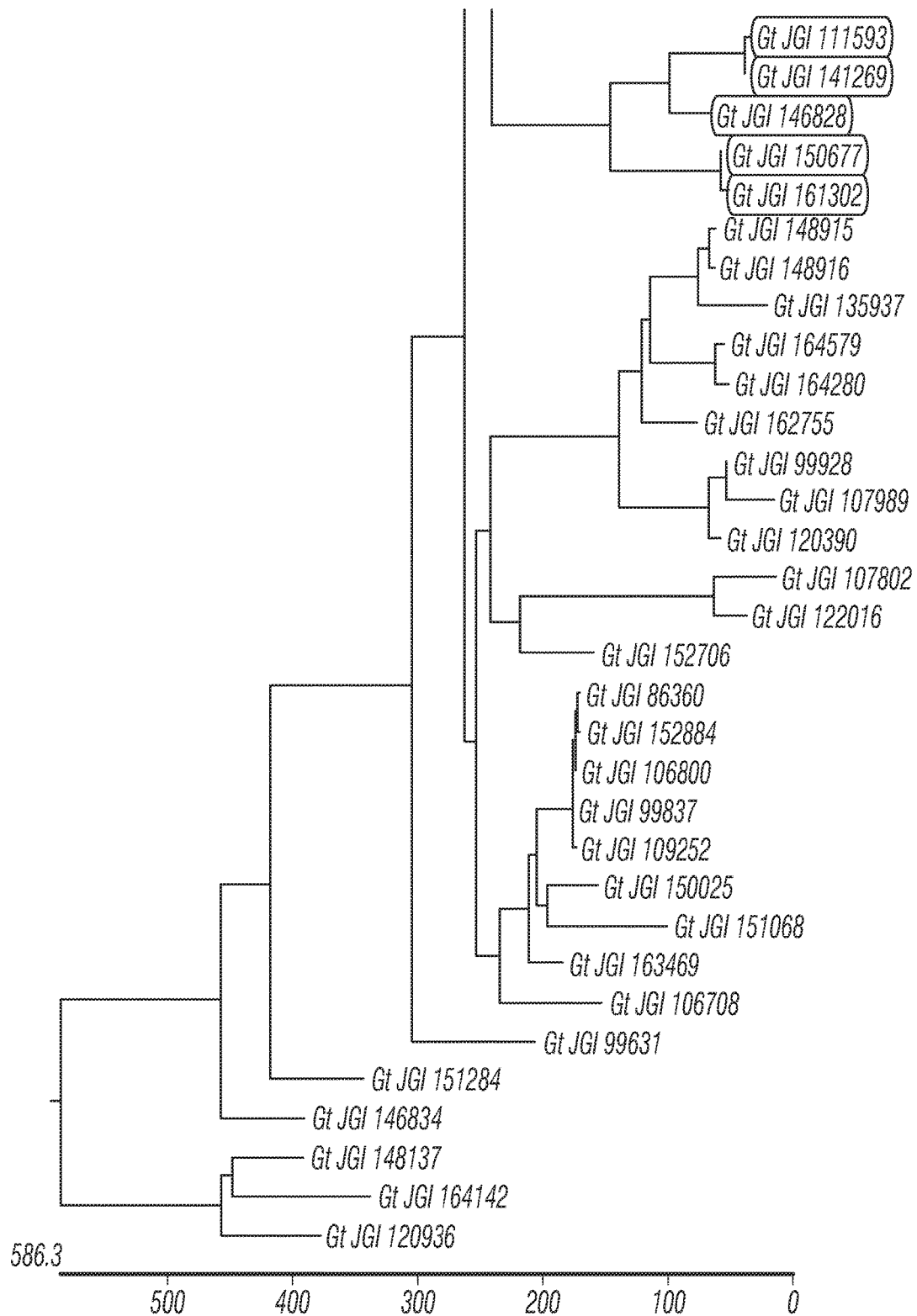

In cultured rat pyramidal neurons GtACR2-generated hyperpolarizing currents at $E_h$ above −88 mV (FIGS. 4C and D). This value corresponds exactly to $E_{Cl}$ under our conditions (Table 2), confirming that GtACR2 exclusively conducts anions in neurons. This strict selectivity is a second advantage of ACRs over the previously reported Cl⁻-conducting ChR mutants for which $E_{rev}$ is 25-30 mV more positive than $E_{Cl}$, due to residual cation permeability. The range of potentials at which GtACR2 hyperpolarizes the membrane is therefore significantly wider and extends through the values typical for resting potentials of neurons (FIG. 4D). In current clamp experiments GtACR2 completely inhibited electrically evoked spikes at light intensities above 3×10-3 mW/mm2 with high temporal precision (FIGS. 4E and F).

Though not wishing to be limited by a particular mechanism, it appears that the mechanism of anion conductance in ACRs is different from that of the Cl⁻-conducting ChR mutants, as might be expected from their large difference in sequence. ACRs contain a Glu residue corresponding to Glu90 of the cation selectivity filter described for CrChR2. To confer Cl⁻ permeability to this cation-conducting channel, Glu90 required replacement with an uncharged (Ser (15)) or cationic (Lys or Arg (14)) residue. However, the presence of the Glu90 homolog in ACRs shows it is not a barrier to anion permeation in the anion channels unlike in the cation channels. Phylogenetically and functionally, ACRs comprise a distinct class of rhodopsins fundamentally different from cation channelrhodopsins (CCRs). As natural anion channels, ACRs provide hyperpolarizing optogenetic tools optimized by evolution for extremely high light-sensitivity, absolute anion selectivity, and rapid kinetics.

Example 3—PsuACR1 is a Light-Gated Anion Channel (ACR)

An additional ACR has been identified in the marine cryptophyte *Proteomonas sulcata* which shows a close similarity to those ACRs described above that were derived from *G. theta*. This sequence, has been identified as PsChR1 (see GenBank: KF992074, incorporated herein by reference) and has been shown to generate photocurrents when expressed in cultured neurons (Klapoetke N C, Murata Y, Kim S S, Pulver S R, Birdsey-Benson A, Cho Y K, Morimoto T K, Chuong A S, Carpenter E J, Tian Z, Wang J, Xie Y, Yan Z, Zhang Y, Chow B Y, Surek B, Melkonian M, Jayaraman V, Constantine-Paton M, Wong G K, Boyden E S. Nat Methods. 2014 March; 11(3):338-46)), but these photocurrents were not characterized in detail and the measurements did not distinguish between cationic and anionic conductance. In the example below it is demonstrated that the corresponding *P. sulcata* protein exhibits light-gated anion conductance similar to that of the ACRs from *G. theta*, although the amplitude of its photocurrents in cultured mammalian cells is smaller. Therefore, it will be referred to herein as PsuACR1 (SEQ ID NO: 13 and SEQ ID NO: 14), the third letter from the species name was added because the abbreviation Ps was used earlier for a CCR from the green alga *Platymonas subcordiformis*.

In addition to, PsuACR1 primary protein sequence exhibits a high overall similarity and several characteristic features found in the *G. theta* derived ACRs (SEQ ID NO: 1 and 3) described above. It contains a Glu residue (Glu-64) corresponding to Glu-90 of CrChR2 that had to be replaced with a neutral or positively charged residue to convert CrChR2 to a Cl⁻ conducting channel. The position of the proton acceptor in bacteriorhodopsin (Asp-85) is occupied by a non-carboxylic residue, although in PsuACR1 it is Ala (Ala-93) rather than Ser, as in *G. theta* derived ACRs (SEQ ID NO: 1 and 3). Finally, neither of the three residues predicted to form an inner cation channel gate according to the crystal structure of C1C2 chimera (Tyr-109, His-173 and His-304) are conserved in either PsuACR1 ACRs (SEQ ID NO: 13 and 14) or *G. theta* derived ACRs (SEQ ID NO: 1 and 3): Tyr-109 is replaced with Met in all three proteins; His-173 (the position, corresponding to Asp-96 in bacteriorhodopsin), with Leu in GtACR1 and Gln (as in rhodopsin sodium pumps) in GtACR2 (SEQ ID NO: 3) and PsuACR1 (SEQ ID NO: 13); His-304 is replaced with Ala in GtACR1, Ser in GtACR2, and Arg in PsuACR1 (SEQ ID NO: 13).

To establish the electrophysiological properties of PsuACR1 (SEQ ID NO: 13 and 14) it was expressed it in human embryonic kidney (HEK293) cells and measured photocurrents under voltage clamp conditions and the findings appear in FIG. 7. A series of current traces recorded with our standard solutions (126 mM KCl in the pipette and 150 mM NaCl in the bath, pH 7.4) in response to a light pulse of the saturating intensity are shown in FIG. 7A. The mean peak amplitude at −60 mV at the amplifier output was 707±184 pA (mean±SEM, n=18 cells), which was roughly ten times less than that of the currents generated by ACRs derived from *G. theta* (SEQ ID NO: 1 and 3) under the same conditions. Another difference was that PsuACR1 (SEQ ID NO: 13 and 14) currents displayed rapid inactivation under continuous illumination to a plateau level of 56±2% (mean±SEM, n=18 cells), whereas inactivation of photocurrents generated by the *G. theta* derived ACRs (SEQ ID NO: 1 and 3) was much smaller and slower. The sign of PsuACR1 (SEQ ID NO: 13 and 14) photocurrents reversed when the membrane potential was shifted to more positive values. The dependence of its peak amplitude on the holding potential (En) (the IE curve) was linear (FIG. 7D, black line), as that for *G. theta* ACRs (SEQ ID NO: 1 and 3), in contrast to the outward rectification typical of CCRs. The reversal potential ($E_{rev}$) of photocurrents recorded in standard solutions was close to zero (FIG. 7D, black symbols and line).

Figure 7A:
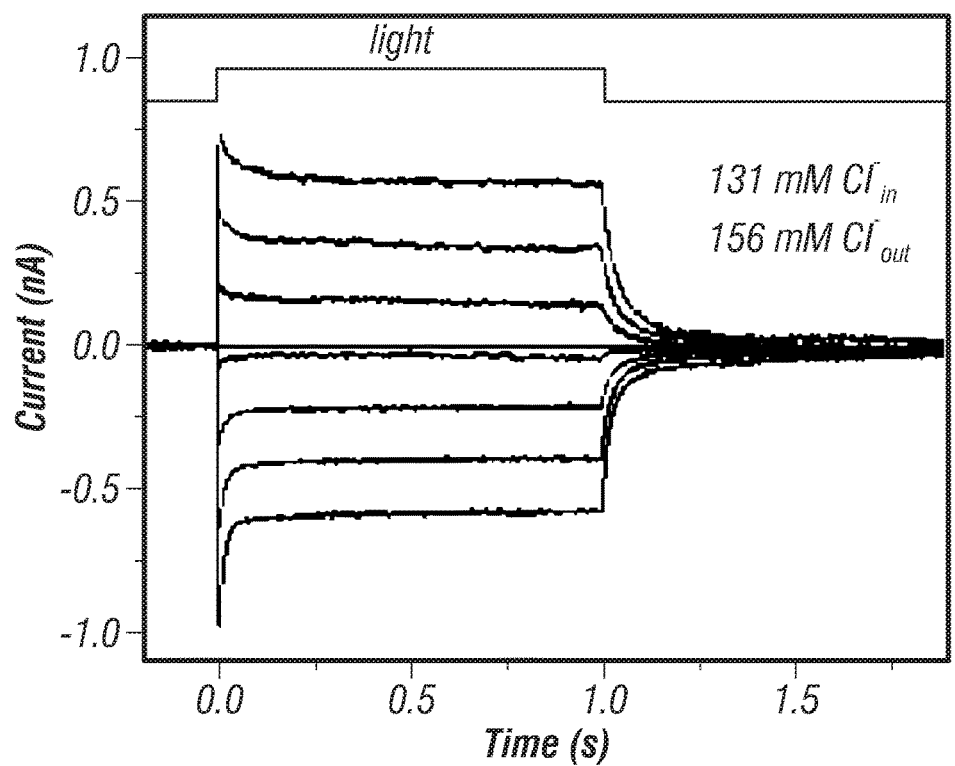
FIGS. 7A-7D: (A-C) Illustrate the photocurrents generated by PsuACR1 in HEK293 cells at the membrane potentials changed in 20-mV steps from −60 mV at the amplifier output (bottom to top) in response to a 1-s light pulse (520 nm). The Cl⁻ concentrations of the pipette and bath solutions were as indicated. (D) The voltage dependencies of the peak current (IE curves) measured with solutions indicated in the legend. The data (mean values±SEM, n=4-9 cells) were normalized to the value measured at −60 mV with standard solutions and corrected for liquid junction potentials.
Figure 7B:
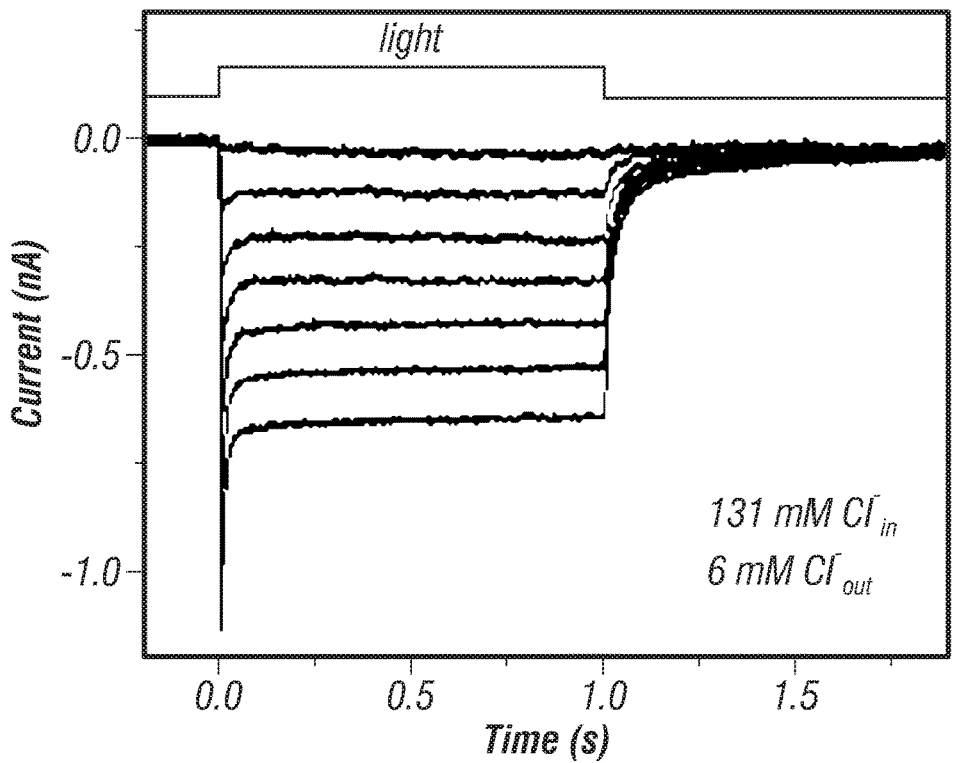
Figure 7C:
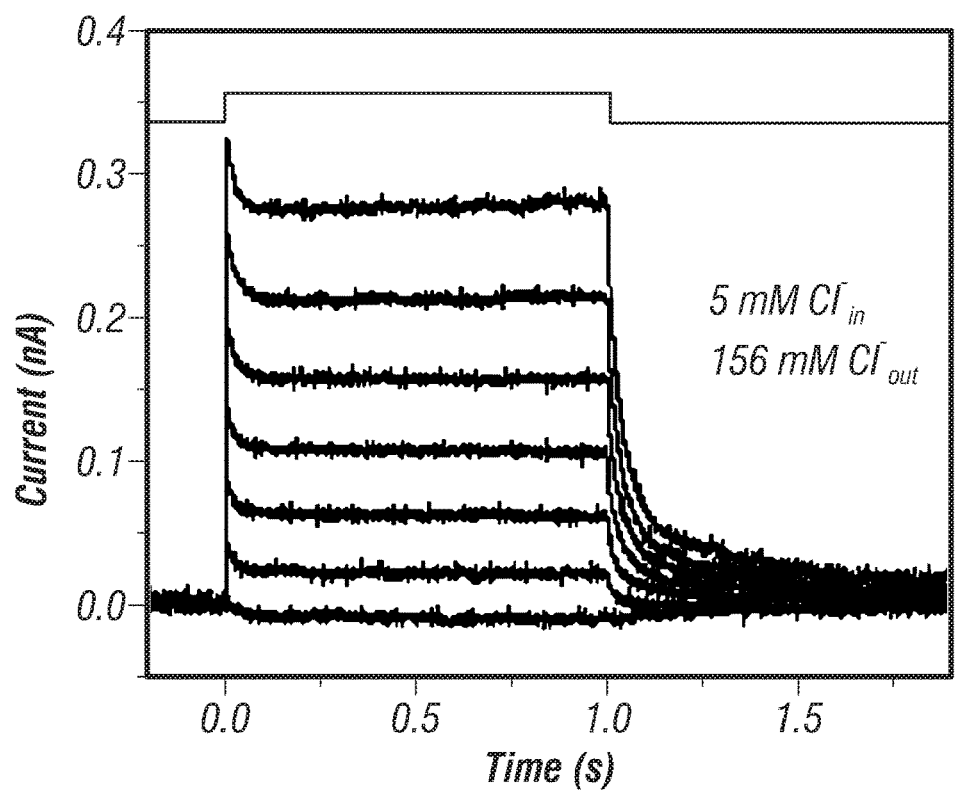
Figure 7D:
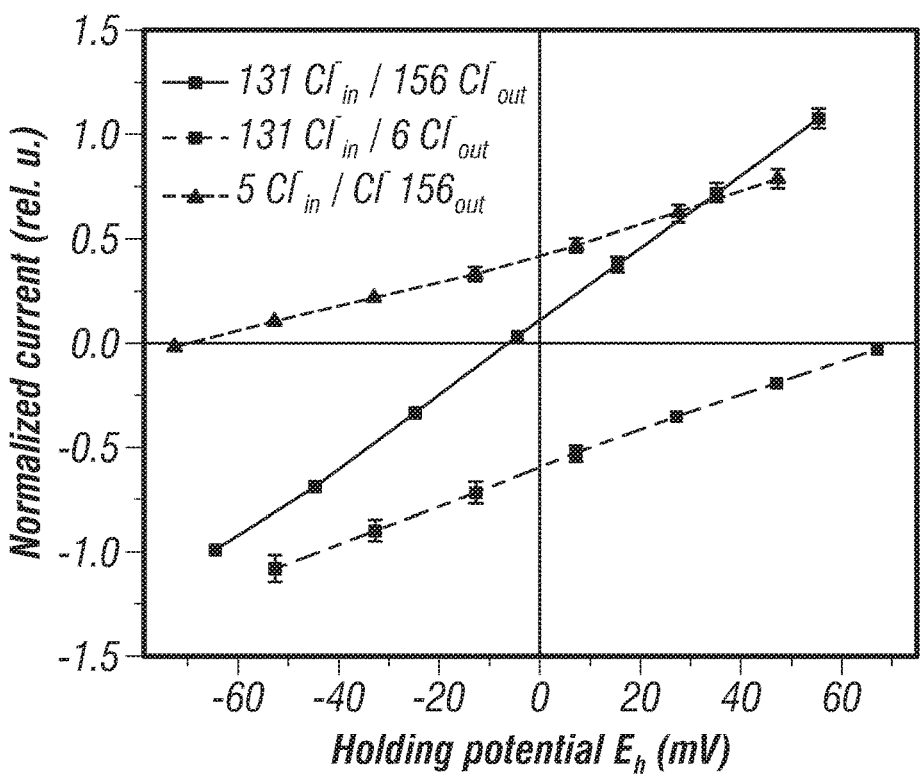

When most of Cl⁻ in the bath was replaced with aspartate, the $E_{rev}$ shifted to 72±2 mV (mean±SEM, n=5 cells). A typical series of photocurrents measured under these conditions is shown in FIG. 7B, and an IE curve, in FIG. 7D (red symbols and line). When Cl⁻ was replaced with Asp⁻ in the pipette, but the bath solution was standard, the $E_{rev}$ shifted to −70±2 mV (mean±SEM, n=4 cells). Photocurrents and an IE curve for these conditions are shown in FIGS. 8C and D (blue symbols and line), respectively. These results indicated that PsuACR1 photocurrents were due to passive Cl⁻ transport.

Figure 8:
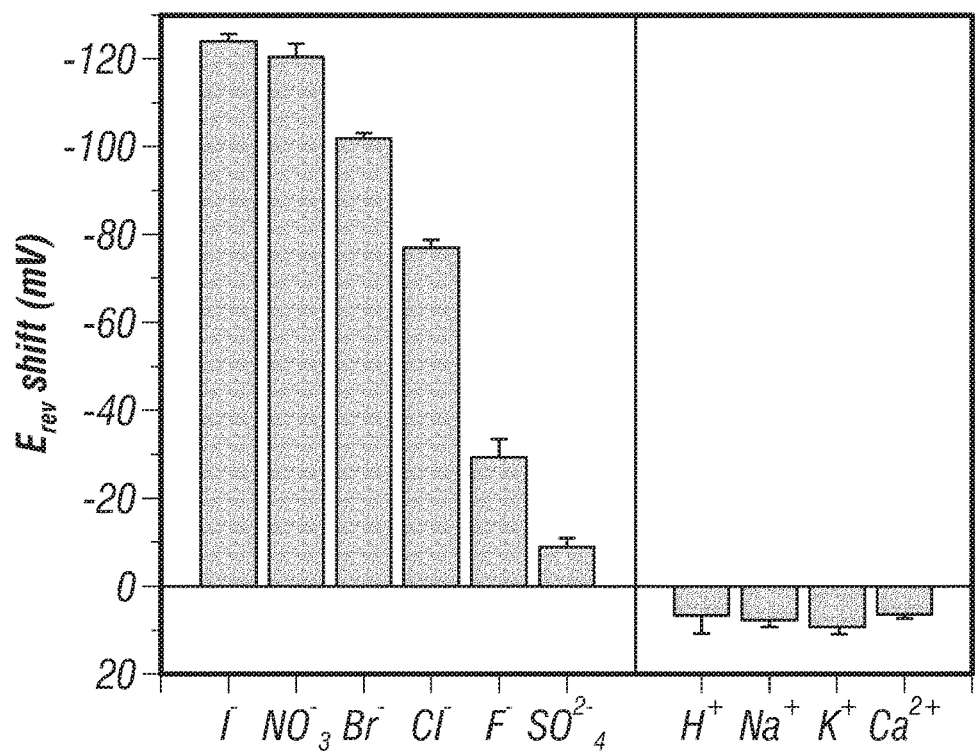
FIG. 8: Illustrates shifts of the $E_{rev}$ of PsuACR1 photocurrents measured upon variation of the anion (left) or cation (right) composition of the bath from the value obtained with non-permeable Asp⁻ (for anions) or non-permeable NMG⁺ (for cations). The data are mean values±SEM (n=3-9 cells).

When Cl⁻ in the bath was replaced with other anions and measured the IE curves. The shifts of the $E_{rev}$ value measured with each anion from that with non-permeable Asp⁻ are shown in FIG. 8. As for *G. theta* ACRs, I⁻ was the most, and F⁻, the least permeable halide, whereas divalent sulphate was practically impermeable. Similarly, practically no shift of the $E_{rev}$ was measured with Na⁺, K⁺ or Ca²⁺ in the bath instead of non-permeable N-methyl-glucamine (NMG⁺), or when the bath pH was decreased from 7.4 to 5.4 (FIG. 8). These results confirmed that PsuACR1 is a light-gated anion channel.

Figure 9:
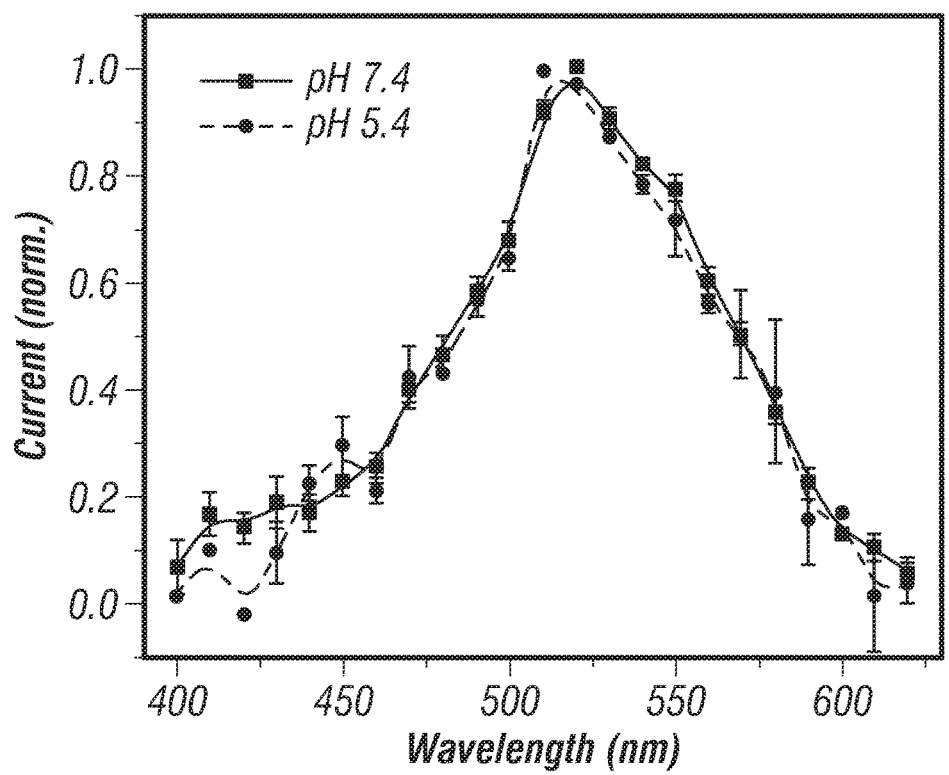
FIG. 9: The action spectrum of PsuACR1 photocurrents.

The action spectrum of PsuACR1 photocurrents measured at pH 7.4 has the maximum at 520 nm and a shoulder at 550 nm (FIG. 9). A decrease to pH 5.4 did not shift the position of the spectral maximum.

Figure 13:
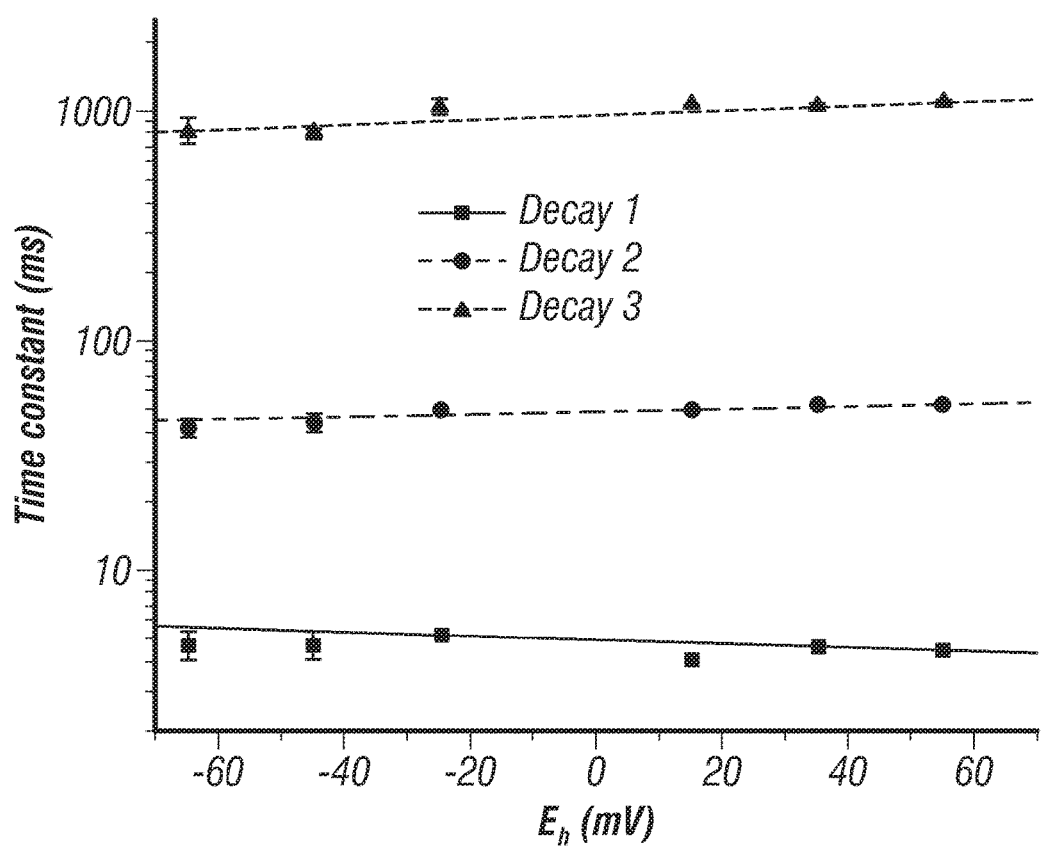
FIG. 13: The voltage dependence of the time constants of PsuACR1 current decay components. The data points are mean values±SEM (n=8 cells).

To characterize the kinetics of PsuACR1 photocurrent under single-turnover conditions, laser flashes (6 ns) were used for photoexcitation (FIG. 10a). Compared to the previously characterized ACRs from G. theta, channel closing in PsuACR1 at pH 7.4 was ~8 times faster (FIG. 10b). The current decay was fit with 3 exponentials. The third, slowest component made the least contribution to the overall amplitude. The voltage dependencies (IE curves) of the amplitudes of the three decay components of PsuACR1 photocurrents are shown in FIG. 10c. The reversal potentials of all components were the same within experimental error. The time constants (τ) of all components were only weakly voltage-dependent (FIG. 13), in contrast to previous observations in GtACR1. The rate of the peak current recovery was measured in double-flash experiments. For PsuACR1 it was ~5 times faster than that for GtACR2, and ~8 times faster than that for GtACR1 (FIG. 10d).

Figure 11A:
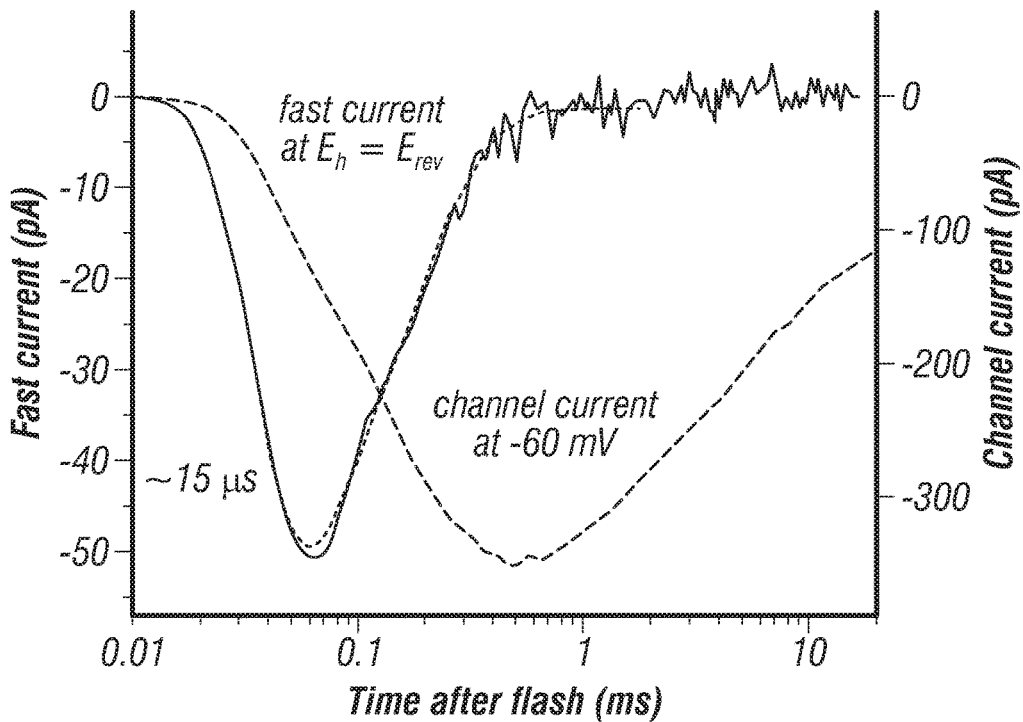
FIG. 11: (a) Fast negative current recorded from PsuACR1 at the reversal potential for channel current (solid line, left axis) and exponential fit of its rise and decay (dotted line), and channel current recorded from the same cell at −60 mV at the amplifier output (dashed line, right axis). (b) Voltage dependencies of fast negative current (squares and solid line, left axis) and channel current (circles and dashed line, right axis) in a typical cell expressing PsuACR1. (c) The dependence of fast negative current on the bath pH. The data points are mean values±SEM (n=3-5 cells).
Figure 11B:
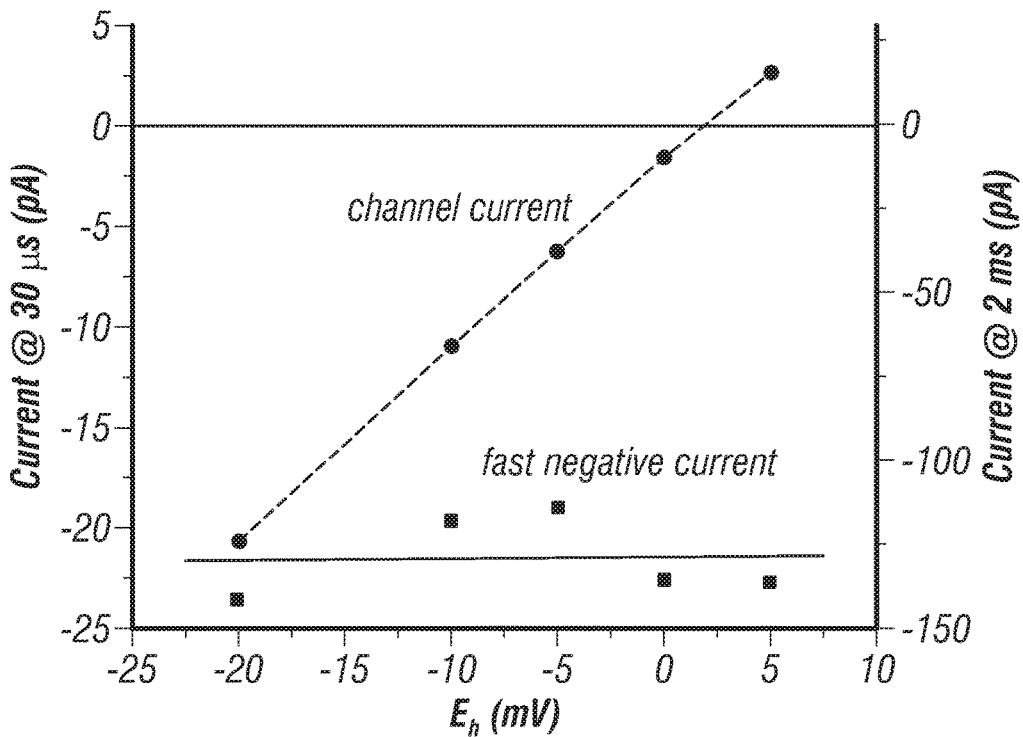
Figure 11C:
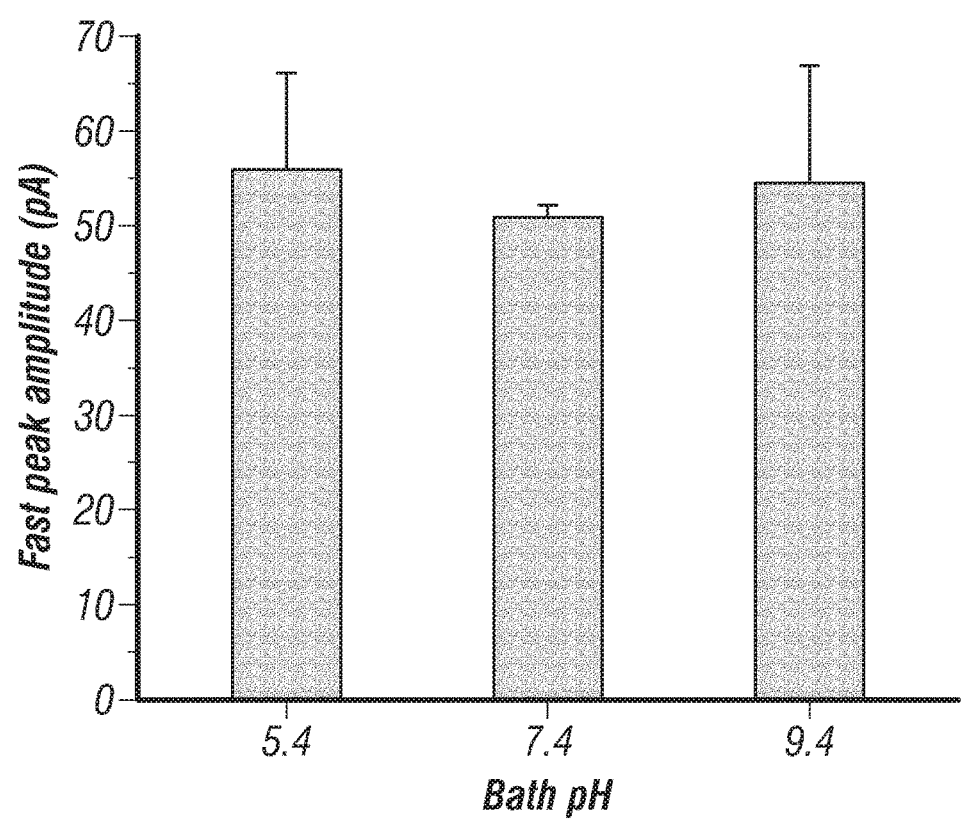

At the reversal potential for channel currents a fast negative signal was recorded, the time course of which was limited by the time resolution of the recording system (FIG. 11a). The inward direction of the fast current recorded from PsuACR1 corresponded to that of the initial charge transfer associated with retinal isomerization. The amplitude of this current in PsuACR1 did not depend on the Vh or pH of the bath in the tested range (FIGS. 11b and c), which further indicated the origin of this current as retinal isomerization.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent they provide exemplary procedural or other details supplementary to those set forth herein, are incorporated herein by reference.

1. J. L. Spudich, O. A. Sineshchekov, E. G. Govorunova, Biochem. Biophys. Acta 1837, 546 (2014).
2. O. P. Ernst et al., Chem. Rev. 114, 126 (2014).
3. K. Deisseroth, Nat. Methods 8, 26 (2011).
4. B. Y. Chow, E. S. Boyden, Sci. Transl. Med. 5, 177ps5 (2013).
5. J. Y. Lin, P. M. Knutsen, A. Muller, D. Kleinfeld, R. Y. Tsien, Nat. Neurosci. 16, 1499 (2013).
6. O. A. Sineshchekov, K.-H. Jung, J. L. Spudich, Proc. Natl. Acad. Sci. USA 99, 8689 (2002).
7. G. Nagel et al., Science 296, 2395 (2002).
8. G. Nagel et al., Proc. Natl. Acad. Sci. USA 100, 13940 (2003).
9. F. Zhang et al., Nature 446, 633 (2007).
10. X. Han, E. S. Boyden, PLoS One 2, e299 (2007).
11. V. Gradinaru, K. R. Thompson, K. Deisseroth, Brain Cell Biol. 36, 129 (2008).
12. B. Y. Chow et al., Nature 463, 98 (2010).
13. A. S. Chuong et al., Nat. Neurosci. 17, 1123 (2014).
14. J. Wietek et al., Science 344, 409 (2014).
15. A. Berndt, S. Y. Lee, C. Ramakrishnan, K. Deisseroth, Science 344, 420 (2014).
16. F. Zhang et al., Cell 147, 1446 (2011).
17. E. G. Govorunova, O. A. Sineshchekov, H. Li, R. Janz, J. L. Spudich, J. Biol. Chem. 288, 29911 (2013).
18. N. C. Klapoetke et al., Nat. Methods 11, 338 (2014).
19. O. A. Sineshchekov et al., Biophys. 1 89, 4310 (2005).
20. V. Gradinaru et al., Cell 141, 154 (2010).
21. B. A. Curtis et al., Nature 492, 59 (2012).
22. D. Gradmann, A. Berndt, F. Schneider, P. Hegemann, Biophys. J. 101, 1057 (2011).
23. T. J. Jentsch, V. Stein, F. Weinreich, A. A. Zdebik, Physiol Rev. 0.82, 503 (2002).
24. M. Kolbe, H. Besir, L. O. Essen, D. Oesterhelt, Science 288, 1390 (2000).
25. P. Bregestovski, T. Waseem, M. Mukhtarov, Front. Mol. Neurosci. 2, 15 (2009).
26. S. J. Husson et al., PLoS One 7, e40937 (2012).
27. K. Ruffert et al., Biochem. Biophys. Res. Commun. 410, 737 (2011).
28. K. Eisenhauer et al., J. Biol. Chem. 287, 6904 (2012).

What is claimed is:

1. A recombinant nucleic acid operatively linked to a heterologous promoter sequence, said recombinant nucleic acid comprising:
   (a) a sequence that encodes a polypeptide with at least 90% identity to an amino acid sequence selected from the group consisting of SEQ ID NO: 1 and SEQ ID NO: 3; or
   (b) a sequence that encodes a polypeptide comprising 225 contiguous amino acids selected from the group consisting of SEQ ID NO: 1 and SEQ ID NO: 3.

2. The recombinant nucleic acid of claim 1, wherein the recombinant nucleic acid comprises an expression vector.

3. A recombinant host cell comprising the recombinant nucleic acid of claim 1.

4. The recombinant host cell of claim 3, wherein said host cell is an isolated human cell.

5. The recombinant host cell of claim 3, wherein said host cell is a non-human mammalian cell.

6. The recombinant host cell of claim 3, wherein said host cell is a bacterial cell.

7. The recombinant host cell of claim 3, wherein said host cell is a yeast cell.

8. The recombinant host cell of claim 3, wherein said host cell is an insect cell.

9. The recombinant host cell of claim 3, wherein said host cell is a plant cell.

10. The recombinant host cell of claim 3, wherein said host cell is an isolated neuronal cell.

11. The recombinant host cell of claim 3, wherein said host cell is an isolated electrically active cell.

12. A cDNA or mRNA comprising a nucleic acid sequence that encodes an amino acid sequence comprising SEQ ID NO: 1 or SEQ ID NO: 3.

* * * * *

SEQUENCE LISTING

```
<160> NUMBER OF SEQ ID NOS: 51

<210> SEQ ID NO 1
<211> LENGTH: 295
<212> TYPE: PRT
<213> ORGANISM: Guillardia theta

<400> SEQUENCE: 1

Met Ser Ser Ile Thr Cys Asp Pro Ala Ile Tyr Gly Glu Trp Ser Arg
1               5                   10                  15

Glu Asn Gln Phe Cys Val Glu Lys Ser Leu Ile Thr Leu Asp Gly Ile
            20                  25                  30

Lys Tyr Val Gln Leu Val Met Ala Val Val Ser Ala Cys Gln Val Phe
        35                  40                  45

Phe Met Val Thr Arg Ala Pro Lys Val Pro Trp Glu Ala Ile Tyr Leu
    50                  55                  60
```

Pro Thr Thr Glu Met Ile Thr Tyr Ser Leu Ala Phe Thr Gly Asn Gly
65                  70                  75                  80

Tyr Ile Arg Val Ala Asn Gly Lys Tyr Leu Pro Trp Ala Arg Met Ala
                85                  90                  95

Ser Trp Leu Cys Thr Cys Pro Ile Met Leu Gly Leu Val Ser Asn Met
            100                 105                 110

Ala Leu Val Lys Tyr Lys Ser Ile Pro Leu Asn Pro Met Met Ile Ala
        115                 120                 125

Ala Ser Ser Ile Cys Thr Val Phe Gly Ile Thr Ala Ser Val Val Leu
    130                 135                 140

Asp Pro Leu His Val Trp Leu Tyr Cys Phe Ile Ser Ser Ile Phe Phe
145                 150                 155                 160

Ile Phe Glu Met Val Val Ala Phe Ala Ile Phe Ala Ile Thr Ile His
                165                 170                 175

Asp Phe Gln Thr Ile Gly Ser Pro Met Ser Leu Lys Val Val Glu Arg
            180                 185                 190

Leu Lys Leu Met Arg Ile Val Phe Tyr Val Ser Trp Met Ala Tyr Pro
        195                 200                 205

Ile Leu Trp Ser Phe Ser Ser Thr Gly Ala Cys Ile Met Ser Glu Asn
    210                 215                 220

Thr Ser Ser Val Leu Tyr Leu Leu Gly Asp Ala Leu Cys Lys Asn Thr
225                 230                 235                 240

Tyr Gly Ile Leu Leu Trp Ala Thr Thr Trp Gly Leu Leu Asn Gly Lys
                245                 250                 255

Trp Asp Arg Asp Tyr Val Lys Gly Arg Asn Val Asp Gly Thr Leu Met
            260                 265                 270

Pro Glu Tyr Glu Gln Asp Leu Glu Lys Gly Asn Thr Glu Arg Tyr Glu
        275                 280                 285

Asp Ala Arg Ala Gly Glu Thr
    290                 295

<210> SEQ ID NO 2
<211> LENGTH: 885
<212> TYPE: DNA
<213> ORGANISM: Guillardia theta

<400> SEQUENCE: 2
atgagcagca tcacctgtga tcccgccatc tacggcgaat ggagcaggga gaaccagttc      60
tgcgtggaga gagcctgat caccctggac ggcatcaagt acgtccagct ggtgatggcc     120
gtcgtgagcg cctgtcaggt gttcttcatg gtgaccagag cccccaaggt gccctgggaa    180
gccatctacc tgcccaccac cgagatgatc acctattccc tggccttcac cggaaacggc    240
tacatcagag tggccaatgg caagtacctg ccctgggcca gaatggccag ctggctgtgc    300
acctgcccta tcatgctggg cctggtgagc aatatggccc tcgtgaagta caagagcatc    360
cccctcaacc ctatgatgat cgccgcctcc agcatctgca ccgtgttcgg catcaccgcc    420
tccgtggtgc tagacccgct gcacgtgtgg ctgtactgtt tcatcagcag catcttcttc    480
atcttcgaga tggtggtggc cttcgccatt ttcgccatta ccatccacga tttccagacc    540
atcggctccc ccatgtccct gaaggtggtg gagaggctga agctgatgag gatcgtgttc    600
tacgtgagct ggatggccta ccctatcctg tggagcttct ccagcaccgg cgcctgcatc    660
atgagcgaga acaccagcag cgtgctgtac ctgctgggcg acgctctgtg caagaacacc    720
tacggcatcc tgctgtgggc tacaacctgg ggcctgctga acggcaagtg ggacagggat    780

```
tacgtgaagg gcaggaacgt ggacggcacc ctgatgcctg agtacgagca ggacctggag    840
aagggcaaca ccgagaggta cgaggacgcc agagccggcg agacc                    885
```

<210> SEQ ID NO 3
<211> LENGTH: 291
<212> TYPE: PRT
<213> ORGANISM: Guillardia theta

<400> SEQUENCE: 3

```
Met Ala Ser Gln Val Val Tyr Gly Glu Trp Ala Ser Thr His Thr Glu
1               5                   10                  15

Cys Tyr Asn Met Ser Arg Ile Asp Ser Thr Phe Val Ser Leu Leu Gln
            20                  25                  30

Leu Val Trp Ala Val Val Ser Gly Cys Gln Thr Ile Phe Met Ile Ser
        35                  40                  45

Arg Ala Pro Lys Val Pro Trp Glu Ser Val Tyr Leu Pro Phe Val Glu
    50                  55                  60

Ser Ile Thr Tyr Ala Leu Ala Ser Thr Gly Asn Gly Thr Leu Gln Met
65                  70                  75                  80

Arg Asp Gly Arg Phe Phe Pro Trp Ser Arg Met Ala Ser Trp Leu Cys
                85                  90                  95

Thr Cys Pro Ile Met Leu Gly Gln Ile Ser Asn Met Ala Leu Val Lys
            100                 105                 110

Tyr Lys Ser Ile Pro Leu Asn Pro Ile Ala Gln Ala Ser Ile Ile
        115                 120                 125

Arg Val Val Met Gly Ile Thr Ala Thr Ile Ser Pro Ala Glu Tyr Met
    130                 135                 140

Lys Trp Leu Phe Phe Phe Phe Gly Ala Thr Cys Leu Val Phe Glu Tyr
145                 150                 155                 160

Ser Val Val Phe Thr Ile Phe Gln Val Gly Leu Tyr Gly Phe Glu Ser
                165                 170                 175

Val Gly Thr Pro Leu Ala Gln Lys Val Val Arg Ile Lys Met Leu
            180                 185                 190

Arg Leu Ile Phe Phe Ile Ala Trp Thr Met Phe Pro Ile Val Trp Leu
    195                 200                 205

Ile Ser Pro Thr Gly Val Cys Val Ile His Glu Asn Val Ser Ala Ile
210                 215                 220

Leu Tyr Leu Leu Ala Asp Gly Leu Cys Lys Asn Thr Tyr Gly Val Ile
225                 230                 235                 240

Leu Trp Ser Thr Ala Trp Gly Val Leu Glu Gly Lys Trp Asp Pro Ala
                245                 250                 255

Cys Leu Pro Gly Gln Glu Lys Pro Glu Ala Asp Asp Pro Phe Gly Leu
            260                 265                 270

Asn His Glu Lys Asn Ala Pro Pro Asn Asp Glu Val Asn Ile Arg Met
        275                 280                 285

Phe Gly Arg
    290
```

<210> SEQ ID NO 4
<211> LENGTH: 873
<212> TYPE: DNA
<213> ORGANISM: Guillardia theta

<400> SEQUENCE: 4

```
atggcctccc aggtcgtgta cggcgagtgg gccagcaccc acacagagtg ctacaacatg    60
```

-continued

```
agcaggatcg acagcacctt cgtgagcctg ctgcagctgg tgtgggccgt ggtgagcgga      120
tgccagacca tcttcatgat cagcagggcc cccaaggtgc cctgggagag cgtgtacctg      180
cccttcgtgg agtccatcac atacgccctg ccagcaccg gcaatggcac actgcagatg       240
agggacggca ggtctcttcc ctggtccagg atggccagct ggctgtgcac atgccccatt      300
atgctgggcc agatctccaa catggctctg gtgaagtaca agagcatccc tctgaacccc      360
atcgcccagg ccgccagcat tatcaggggtg gtgatgggca ttaccgctac catctccccc     420
gccgagtaca tgaagtggct gttcttcttc ttcggcgcta cctgcctggt cttcgaatac      480
agcgtggtgt tcaccatctt ccaggtggga ctgtacggct tcgagtccgt gggcaccccct     540 ctggcccaga aggtggtggt gaggatcaag atgctgaggc tgatcttctt catcgcctgg      600
accatgttcc ccatcgtgtg gctgatttcc cccaccggcg tgtgcgtgat ccacgagaac      660
gtgagcgcca tcctgtatct gctcgccgac ggcctgtgca agaacaccta cggcgtgatc      720
ctgtggtcca ccgcctgggg agtgctcgag ggaaagtggg accggcttg cctccctggc       780 caggagaagc ctgaggccga cgacccttc ggactgaacc acgagaagaa tgccccccc       840 aacgacgagg tcaacatcag aatgttcggc agg                                   873
```

```
<210> SEQ ID NO 5
<211> LENGTH: 288
<212> TYPE: PRT
<213> ORGANISM: Guillardia theta

<400> SEQUENCE: 5

Met Ser Val Val Tyr Gly Glu Trp Ala Ala Gln Asn Pro Ser Cys Val
1               5                   10                  15

Thr Leu Ser Asn Ile Asp Leu Gly Val Arg Thr Phe Glu Leu Cys Trp
            20                  25                  30

Gly Ile Met Cys Ala Cys Gln Ala Val Phe Phe Ala Leu Arg Tyr Pro
        35                  40                  45

Arg Gly Thr Trp Glu Phe Val Leu Val Pro Leu Thr Glu Cys Phe Val
    50                  55                  60

Tyr Gly Leu Gly Tyr Ser Glu Ile Gly Tyr Ile Leu Leu Trp Asp Gly
65                  70                  75                  80

Arg Gln Val Leu Trp Thr Arg Thr Val Leu Trp Leu Ala Thr Val Pro
                85                  90                  95

Ile Ile Leu Asn Gln Ile Asn Gly Met Ala Ala Val Arg Ile Tyr Gly
            100                 105                 110

Val Asp Leu Asn Val Met Gln Met Tyr Phe Ser Thr Leu Met Ile Cys
        115                 120                 125

Phe Gly His Thr Ala Ala Leu Thr His Asn Gln Ser Leu Lys Trp Leu
    130                 135                 140

Phe Phe Ile Ile Ala Met Ala Ile Phe Gly Leu Ile Cys Phe Ile Asn
145                 150                 155                 160

Tyr His Thr Phe Thr Ala Ala Glu Lys His Tyr Lys Glu Ser Gly Ser
                165                 170                 175

Glu Ile Asp Leu Ile Ile Ala Lys Arg Ile Arg Leu Leu Ala Val Ile
            180                 185                 190

Phe Phe Thr Ser Trp Thr Met Tyr Pro Leu Phe Phe Val Leu Ser Val
        195                 200                 205

Glu Gly Ala Cys Val Ala Ser Glu Ser Val Ile Leu Val Cys Phe Ala
    210                 215                 220
```

```
Leu Ala Asp Leu Leu Ser Lys Asn Val Phe Gly Val Leu Phe Trp Asp
225                 230                 235                 240

Thr Leu Trp Asn Leu Gln Asp Gly Lys Trp Ser Ser Tyr Gly Thr Val
                245                 250                 255

Thr Phe Phe Lys Thr Thr Asp Ser Val Thr Lys Thr Ala Ile Ser Thr
            260                 265                 270

Ala Met Glu Glu Phe Ala Lys Gln Lys Ala Ser Arg Ser Asp Asn
        275                 280                 285
```

<210> SEQ ID NO 6
<211> LENGTH: 864
<212> TYPE: DNA
<213> ORGANISM: Guillardia theta

<400> SEQUENCE: 6

```
atgtccgtgg tgtacggaga gtgggccgcc caaaacccta gctgcgtgac cctgagcaat      60
atcgacctgg gcgtgaggac ctttgagctg tgctggggca tcatgtgcgc ttgccaggcc     120
gtgttcttcg ccctcaggta ccccaggggc acatgggagt ttgtgctggt cccccctgaca   180
gagtgtttcg tgtacggact gggctacagc gagattggct acatcctcct gtgggatggc    240
aggcaggtgc tctggaccag gacagtcctg tggctcgcca ccgtgcccat catcctgaac    300
cagatcaacg gcatggccgc cgtcaggatc tacggcgtgg acctgaacgt catgcagatg    360
tacttcagca ccctgatgat ctgctttggc ataccgccg ccctgaccca aaccagagc      420
ctcaagtggc tgttctttat catcgccatg gccattttcg gcctgatctg cttcatcaac    480
taccacacct tcaccgccgc cgagaagcac tacaaggagt ccggctccga gatcgacctc    540
atcatcgcca agaggatcag gctgctggcc gtcatcttct tcaccagctg gaccatgtac    600
cccctcttct tcgtgctgag cgtggaggga gcctgtgtgg ctagcgagtc cgtcatcctc    660
gtgtgcttcg ccctggccga cctgctgagc aagaacgtgt tcggcgtcct cttctgggac    720
accctctgga acctgcagga cggcaaatgg agctcctatg gcaccgtgac cttcttcaag    780
accaccgaca gcgtcaccaa gaccgccatc tccaccgcca tggaagagga gtttgccaag    840
cagaaggcta gcaggagcga caac                                          864
```

<210> SEQ ID NO 7
<211> LENGTH: 712
<212> TYPE: PRT
<213> ORGANISM: Chlamydomonas reinhardtii

<400> SEQUENCE: 7

```
Met Ser Arg Arg Pro Trp Leu Leu Ala Leu Ala Leu Ala Val Ala Leu
1               5                  10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110
```

-continued

```
Thr Trp Lys Ser Thr Cys Gly Trp Glu Glu Ile Tyr Val Ala Thr Ile
            115                 120                 125
Glu Met Ile Lys Phe Ile Ile Glu Tyr Phe His Glu Phe Asp Glu Pro
        130                 135                 140
Ala Val Ile Tyr Ser Ser Asn Gly Asn Lys Thr Val Trp Leu Arg Tyr
145                 150                 155                 160
Ala Glu Trp Leu Leu Thr Cys Pro Val Ile Leu Ile His Leu Ser Asn
                165                 170                 175
Leu Thr Gly Leu Ala Asn Asp Tyr Asn Lys Arg Thr Met Gly Leu Leu
            180                 185                 190
Val Ser Asp Ile Gly Thr Ile Val Trp Gly Thr Thr Ala Ala Leu Ser
        195                 200                 205
Lys Gly Tyr Val Arg Val Ile Phe Phe Leu Met Gly Leu Cys Tyr Gly
210                 215                 220
Ile Tyr Thr Phe Phe Asn Ala Ala Lys Val Tyr Ile Glu Ala Tyr His
225                 230                 235                 240
Thr Val Pro Lys Gly Ile Cys Arg Asp Leu Val Arg Tyr Leu Ala Trp
                245                 250                 255
Leu Tyr Phe Cys Ser Trp Ala Met Phe Pro Val Leu Phe Leu Leu Gly
            260                 265                 270
Pro Glu Gly Phe Gly His Ile Asn Gln Phe Asn Ser Ala Ile Ala His
        275                 280                 285
Ala Ile Leu Asp Leu Ala Ser Lys Asn Ala Trp Ser Met Met Gly His
290                 295                 300
Phe Leu Arg Val Lys Ile His Glu His Ile Leu Leu Tyr Gly Asp Ile
305                 310                 315                 320
Arg Lys Lys Gln Lys Val Asn Val Ala Gly Gln Glu Met Glu Val Glu
                325                 330                 335
Thr Met Val His Glu Glu Asp Glu Thr Gln Lys Val Pro Thr Ala
            340                 345                 350
Lys Tyr Ala Asn Arg Asp Ser Phe Ile Ile Met Arg Asp Arg Leu Lys
        355                 360                 365
Glu Lys Gly Phe Glu Thr Arg Ala Ser Leu Asp Gly Asp Pro Asn Gly
370                 375                 380
Asp Ala Glu Ala Asn Ala Ala Gly Gly Lys Pro Gly Met Glu Met
385                 390                 395                 400
Gly Lys Met Thr Gly Met Gly Met Ser Met Gly Ala Gly Met Gly Met
                405                 410                 415
Ala Asn Ile Asp Ser Gly Arg Val Ile Leu Ala Val Pro Asp Ile Ser
            420                 425                 430
Met Val Asp Phe Phe Arg Glu Gln Phe Ala Arg Leu Pro Val Pro Tyr
        435                 440                 445
Glu Leu Val Pro Ala Leu Gly Ala Glu Asn Thr Leu Gln Leu Val Gln
450                 455                 460
Gln Ala Gln Ser Leu Gly Gly Cys Asp Phe Val Leu Met His Pro Glu
465                 470                 475                 480
Phe Leu Arg Asp Arg Ser Pro Thr Gly Leu Leu Pro Arg Leu Lys Met
                485                 490                 495
Gly Gly Gln Arg Ala Ala Ala Phe Gly Trp Ala Ala Ile Gly Pro Met
            500                 505                 510
Arg Asp Leu Ile Glu Gly Ser Gly Val Asp Gly Trp Leu Glu Gly Pro
        515                 520                 525
Ser Phe Gly Ala Gly Ile Asn Gln Gln Ala Leu Val Ala Leu Ile Asn
```

```
                530             535             540
Arg Met Gln Gln Ala Lys Lys Met Gly Met Met Gly Met Gly Met
545                 550             555             560

Gly Met Gly Gly Gly Met Gly Met Gly Met Gly Met Gly Met Met
                565             570             575

Ala Pro Ser Met Asn Ala Gly Met Thr Gly Gly Met Gly Ala Ser
                580             585             590

Met Gly Gly Ala Val Met Gly Met Gly Met Gly Gln Pro Met Gln
                595             600             605

Gln Ala Met Pro Ala Met Ser Pro Met Met Thr Gln Gln Pro Ser Met
610                 615             620

Met Ser Gln Pro Ser Ala Met Ser Ala Gly Gly Ala Met Gln Ala Met
625                 630             635             640

Gly Gly Val Met Pro Ser Pro Ala Pro Gly Gly Arg Val Gly Thr Asn
                645             650             655

Pro Leu Phe Gly Ser Ala Pro Ser Pro Leu Ser Ser Gln Pro Gly Ile
                660             665             670

Ser Pro Gly Met Ala Thr Pro Pro Ala Ala Thr Ala Ala Pro Ala Ala
                675             680             685

Gly Gly Ser Glu Ala Glu Met Leu Gln Gln Leu Met Ser Glu Ile Asn
690                 695             700

Arg Leu Lys Asn Glu Leu Gly Glu
705                 710
```

<210> SEQ ID NO 8
<211> LENGTH: 737
<212> TYPE: PRT
<213> ORGANISM: Chlamydomonas reinhardtii

<400> SEQUENCE: 8

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ala Gly Phe Ser Ile
                50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Cys
                115                 120                 125

Pro Val Ile Leu Ile His Leu Ser Asn Leu Thr Gly Leu Ser Asn Asp
                130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190
```

-continued

```
Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Asn Lys Gly Thr Gly Lys Tyr Ala Ser Arg Glu
305                 310                 315                 320

Ser Phe Leu Val Met Arg Asp Lys Met Lys Glu Lys Gly Ile Asp Val
            325                 330                 335

Arg Ala Ser Leu Asp Asn Ser Lys Glu Val Glu Gln Glu Gln Ala Ala
            340                 345                 350

Arg Ala Ala Met Met Met Met Asn Gly Asn Gly Met Gly Met Gly Met
            355                 360                 365

Gly Met Asn Gly Met Asn Gly Met Gly Gly Met Asn Gly Met Ala Gly
            370                 375                 380

Gly Ala Lys Pro Gly Leu Glu Leu Thr Pro Gln Leu Gln Pro Gly Arg
385                 390                 395                 400

Val Ile Leu Ala Val Pro Asp Ile Ser Met Val Asp Phe Phe Arg Glu
            405                 410                 415

Gln Phe Ala Gln Leu Ser Val Thr Tyr Glu Leu Val Pro Ala Leu Gly
            420                 425                 430

Ala Asp Asn Thr Leu Ala Leu Val Thr Gln Ala Gln Asn Leu Gly Gly
            435                 440                 445

Val Asp Phe Val Leu Ile His Pro Glu Phe Leu Arg Asp Arg Ser Ser
            450                 455                 460

Thr Ser Ile Leu Ser Arg Leu Arg Gly Ala Gly Gln Arg Val Ala Ala
465                 470                 475                 480

Phe Gly Trp Ala Gln Leu Gly Pro Met Arg Asp Leu Ile Glu Ser Ala
            485                 490                 495

Asn Leu Asp Gly Trp Leu Glu Gly Pro Ser Phe Gly Gln Gly Ile Leu
            500                 505                 510

Pro Ala His Ile Val Ala Leu Val Ala Lys Met Gln Gln Met Arg Lys
            515                 520                 525

Met Gln Gln Met Gln Gln Ile Gly Met Met Thr Gly Met Asn Gly
            530                 535                 540

Met Gly Gly Gly Met Gly Gly Met Asn Gly Met Gly Gly Gly Asn
545                 550                 555                 560

Gly Met Asn Asn Met Gly Asn Gly Met Gly Gly Met Gly Asn Gly
            565                 570                 575

Met Gly Gly Asn Gly Met Asn Gly Met Gly Gly Asn Gly Met Asn
            580                 585                 590

Asn Met Gly Gly Asn Gly Met Ala Gly Asn Gly Met Gly Gly Met
            595                 600                 605

Gly Gly Asn Gly Met Gly Gly Ser Met Asn Gly Met Ser Ser Gly Val
```

```
                610                 615                 620
Val Ala Asn Val Thr Pro Ser Ala Ala Gly Gly Met Gly Gly Met Met
625                 630                 635                 640

Asn Gly Gly Met Ala Ala Pro Gln Ser Pro Gly Met Asn Gly Gly Arg
                645                 650                 655

Leu Gly Thr Asn Pro Leu Phe Asn Ala Ala Pro Ser Pro Leu Ser Ser
                660                 665                 670

Gln Leu Gly Ala Glu Ala Gly Met Gly Ser Met Gly Gly Met Gly Gly
                675                 680                 685

Met Ser Gly Met Gly Gly Met Gly Gly Met Gly Gly Met Gly Gly Ala
                690                 695                 700

Gly Ala Ala Thr Thr Gln Ala Ala Gly Gly Asn Ala Glu Ala Glu Met
705                 710                 715                 720

Leu Gln Asn Leu Met Asn Glu Ile Asn Arg Leu Lys Arg Glu Leu Gly
                725                 730                 735

Glu

<210> SEQ ID NO 9
<211> LENGTH: 352
<212> TYPE: PRT
<213> ORGANISM: Chlamydomonas (Chloromonas) augustae

<400> SEQUENCE: 9

Met Asp Thr Leu Ala Trp Val Ala Arg Glu Leu Leu Ser Thr Ala His
1               5                   10                  15

Asp Ala Thr Pro Ala Thr Ala Thr Pro Ser Thr Asp His Ser Thr Pro
                20                  25                  30

Ser Thr Asp His Gly Ser Gly Glu Thr Phe Asn Val Thr Ile Thr Ile
                35                  40                  45

Gly Gly Gly His His Gly Gly His Ala Gly Pro Val Asp Asn Ser Ile
            50                  55                  60

Val Ile Gly Gly Ile Asp Gly Trp Ile Ala Ile Pro Ala Gly Asp Cys
65                  70                  75                  80

Tyr Cys Ala Gly Trp Tyr Val Ser His Gly Ser Ser Phe Glu Ala Thr
                85                  90                  95

Phe Ala His Val Cys Gln Trp Ser Ile Phe Ala Val Cys Ile Leu Ser
                100                 105                 110

Leu Leu Trp Tyr Ala Trp Gln Tyr Trp Lys Ala Thr Cys Gly Trp Glu
            115                 120                 125

Glu Val Tyr Val Cys Cys Ile Glu Leu Val Phe Ile Cys Phe Glu Leu
            130                 135                 140

Tyr His Glu Phe Asp Ser Pro Cys Ser Leu Tyr Leu Ser Thr Ala Asn
145                 150                 155                 160

Ile Val Asn Trp Leu Arg Tyr Ser Glu Trp Leu Leu Cys Cys Pro Val
                165                 170                 175

Ile Leu Ile His Leu Ser Asn Val Thr Gly Leu Ser Asp Asp Tyr Gly
            180                 185                 190

Arg Arg Thr Met Gly Leu Leu Val Ser Asp Ile Ala Thr Ile Val Phe
            195                 200                 205

Gly Ile Thr Ala Ala Met Leu Val Ser Trp Pro Lys Ile Ile Phe Tyr
            210                 215                 220

Leu Leu Gly Phe Thr Met Cys Cys Tyr Thr Phe Tyr Leu Ala Ala Lys
225                 230                 235                 240

Val Leu Ile Glu Ser Phe His Gln Val Pro Lys Gly Ile Cys Arg His
```

```
                    245                 250                 255
Leu Val Lys Ala Met Ala Ile Thr Tyr Tyr Val Gly Trp Ser Phe Phe
                260                 265                 270

Pro Leu Ile Phe Leu Phe Gly Gln Ser Gly Phe Lys Lys Ile Ser Pro
                275                 280                 285

Tyr Ala Asp Val Ile Ala Ser Ser Phe Gly Asp Leu Ile Ser Lys Asn
                290                 295                 300

Met Phe Gly Leu Leu Gly His Phe Leu Arg Val Lys Ile His Glu His
305                 310                 315                 320

Ile Leu Lys His Gly Asp Ile Arg Lys Thr Thr His Leu Arg Ile Ala
                325                 330                 335

Gly Glu Glu Lys Glu Val Glu Thr Phe Val Glu Glu Asp Glu Asp
                340                 345                 350

<210> SEQ ID NO 10
<211> LENGTH: 593
<212> TYPE: PRT
<213> ORGANISM: Mesostigma viride

<400> SEQUENCE: 10

Met Ser Pro Pro Thr Ser Pro Thr Pro Asp Thr Gly His Asp Thr Pro
1               5                   10                  15

Asp Thr Gly His Asp Thr Gly Gly His Gly Ala Val Glu Ile Cys Phe
                20                  25                  30

Ala Pro Cys Glu Glu Asp Cys Val Thr Ile Arg Tyr Phe Val Glu Asn
                35                  40                  45

Asp Phe Glu Gly Cys Ile Pro Gly His Phe Asp Gln Tyr Ser Ser His
            50                  55                  60

Gly Ser Leu His Asp Ile Val Lys Ala Ala Leu Tyr Ile Cys Met Val
65              70                  75                  80

Ile Ser Ile Leu Gln Ile Leu Phe Tyr Gly Phe Gln Trp Trp Arg Lys
                85                  90                  95

Thr Cys Gly Trp Glu Val Trp Phe Val Ala Cys Ile Glu Thr Ser Ile
                100                 105                 110

Tyr Ile Ile Ala Ile Thr Ser Glu Ala Asp Ser Pro Phe Thr Leu Tyr
                115                 120                 125

Leu Thr Asn Gly Gln Ile Ser Pro Gln Leu Arg Tyr Met Glu Trp Leu
            130                 135                 140

Met Thr Cys Pro Val Ile Leu Ile Ala Leu Ser Asn Ile Thr Gly Met
145                 150                 155                 160

Ala Glu Glu Tyr Asn Lys Arg Thr Met Thr Leu Leu Thr Ser Asp Val
                165                 170                 175

Cys Cys Ile Val Leu Gly Met Met Ser Ala Ala Ser Lys Pro Arg Leu
                180                 185                 190

Lys Gly Ile Leu Tyr Ala Val Gly Trp Ala Phe Gly Ala Trp Thr Tyr
                195                 200                 205

Trp Thr Ala Leu Gln Val Tyr Arg Asp Ala His Lys Ala Val Pro Lys
            210                 215                 220

Pro Leu Ala Trp Tyr Val Arg Ala Met Gly Tyr Val Phe Phe Thr Ser
225                 230                 235                 240

Trp Leu Thr Phe Pro Gly Trp Phe Leu Leu Gly Pro Glu Gly Leu Glu
                245                 250                 255

Val Val Thr Gly Thr Val Ser Thr Leu Met His Ala Cys Ser Asp Leu
                260                 265                 270
```

Ile Ser Lys Asn Leu Trp Gly Phe Met Asp Trp His Leu Arg Val Leu
275                 280                 285

Val Ala Arg His His Arg Lys Leu Phe Lys Ala Glu Glu His Ala
290                 295                 300

Leu Lys Lys Gly Gln Thr Leu Glu Pro Gly Met Pro Arg Ser Thr Ser
305                 310                 315                 320

Phe Val Arg Gly Leu Gly Asp Asp Val Glu Ile Asp Pro Ser Tyr Glu
                325                 330                 335

Leu Tyr Arg Leu Lys Arg Gln Asn His Pro Glu Tyr Phe Leu Ser Pro
            340                 345                 350

Ala Gln Thr Pro Arg Arg Gly Pro Ser Phe Asp Lys Arg Thr Ser Phe
        355                 360                 365

Glu Met Asp Gly Gly Lys Asn Gly Met Leu Gln Met Met Pro Val Thr
370                 375                 380

Gly Met Gly Met Gly Met Gly Met Gly Met Gly Gly Lys Thr Val
385                 390                 395                 400

Leu Phe Leu Asp Tyr Thr Gly Gly Tyr Val Ser Phe Phe Glu Gln
                405                 410                 415

Gln Leu Ser Asn Met Gly Val Asn Val Thr Lys Cys Trp Ser Asp Asp
            420                 425                 430

Asp Met Tyr Asn Thr Ala Gly Val Ala Asn Val Lys Gln Leu Phe His
        435                 440                 445

Phe Ala Met Ile Pro Asn Asn Ala Leu Gly Gly Gln Met Val Met Asp
    450                 455                 460

Leu Arg Gly Thr Gly Leu Leu Val Val Ala Tyr Gly Pro Glu Pro Pro
465                 470                 475                 480

Met Pro Gly Met Gly Gln Asp Glu Phe Val Pro Leu Gln Met Pro Gly
                485                 490                 495

Val Pro Tyr Asp Glu Ser Ile Leu His Asn Leu Val Met Arg His Ala
            500                 505                 510

Ile Thr Gln Gly Leu Gly Met Asn Gly Met Gly Asn Met Gly Gln
        515                 520                 525

Gln Gln Gln Met Met Gly Met Gln Gly Asn Met Asn Gly Met Gln Gly
530                 535                 540

Asn Met Asn Gly Met Gln Gly Asn Met Asn Gly Met Gln Gly Asn Met
545                 550                 555                 560

Ser Gly Met Gln Gly Asn Met Asn Gly Met Gln Gly Asn Ser Gly Met
                565                 570                 575

Asn Gln Gly Trp Asn Asn Gln Gly Phe Thr Asn Thr Gly Ala Phe Gly
            580                 585                 590

Tyr

<210> SEQ ID NO 11
<211> LENGTH: 274
<212> TYPE: PRT
<213> ORGANISM: Halobacterium salinarum

<400> SEQUENCE: 11

Met Ser Ile Thr Ser Val Pro Gly Val Val Asp Ala Gly Val Leu Gly
1               5                   10                  15

Ala Gln Ser Ala Ala Val Arg Glu Asn Ala Leu Leu Ser Ser Ser
            20                  25                  30

Leu Trp Val Asn Val Ala Leu Ala Gly Ile Ala Ile Leu Val Phe Val
        35                  40                  45

```
Tyr Met Gly Arg Thr Ile Arg Pro Gly Arg Pro Leu Ile Trp Gly
    50              55                  60

Ala Thr Leu Met Ile Pro Leu Val Ser Ile Ser Ser Tyr Leu Gly Leu
65              70                  75                  80

Leu Ser Gly Leu Thr Val Gly Met Ile Glu Met Pro Ala Gly His Ala
                85                  90                  95

Leu Ala Gly Glu Met Val Arg Ser Gln Trp Gly Arg Tyr Leu Thr Trp
            100                 105                 110

Ala Leu Ser Thr Pro Met Ile Leu Ala Leu Gly Leu Leu Ala Asp
            115                 120                 125

Val Asp Leu Gly Ser Leu Phe Thr Val Ile Ala Asp Ile Gly Met
130                 135                 140

Cys Val Thr Gly Leu Ala Ala Ala Met Thr Thr Ser Ala Leu Leu Phe
145                 150                 155                 160

Arg Trp Ala Phe Tyr Ala Ile Ser Cys Ala Phe Phe Val Val Val Leu
                165                 170                 175

Ser Ala Leu Val Thr Asp Trp Ala Ala Ser Ala Ser Ala Gly Thr
            180                 185                 190

Ala Glu Ile Phe Asp Thr Leu Arg Val Leu Thr Val Val Leu Trp Leu
            195                 200                 205

Gly Tyr Pro Ile Val Trp Ala Val Gly Val Glu Gly Leu Ala Leu Val
210                 215                 220

Gln Ser Val Gly Val Thr Ser Trp Ala Tyr Ser Val Leu Asp Val Phe
225                 230                 235                 240

Ala Lys Tyr Val Phe Ala Phe Ile Leu Leu Arg Trp Val Ala Asn Asn
                245                 250                 255

Glu Arg Thr Val Ala Val Ala Gly Gln Thr Leu Gly Thr Met Ser Ser
            260                 265                 270

Asp Asp

<210> SEQ ID NO 12
<211> LENGTH: 272
<212> TYPE: PRT
<213> ORGANISM: Nonlabens marinus

<400> SEQUENCE: 12

Met Lys Asn Ile Glu Ser Leu Phe Asp Tyr Ser Ala Gly Gln Phe Glu
1               5                   10                  15

Phe Ile Asp His Leu Leu Thr Met Gly Val Gly Val His Phe Ala Ala
                20                  25                  30

Leu Ile Phe Phe Leu Val Val Ser Gln Phe Val Ala Pro Lys Tyr Arg
            35                  40                  45

Ile Ala Thr Ala Leu Ser Cys Ile Val Met Val Ser Ala Gly Leu Ile
50                  55                  60

Leu Asn Ser Gln Ala Val Met Trp Thr Asp Ala Tyr Ala Tyr Val Asp
65                  70                  75                  80

Gly Ser Tyr Gln Leu Gln Asp Leu Thr Phe Ser Asn Gly Tyr Arg Tyr
                85                  90                  95

Val Asn Trp Met Ala Thr Ile Pro Cys Leu Leu Leu Gln Leu Leu Ile
            100                 105                 110

Val Leu Asn Leu Lys Gly Lys Glu Leu Phe Ser Thr Ala Thr Trp Leu
            115                 120                 125

Ile Leu Ala Ala Trp Gly Met Ile Ile Thr Gly Tyr Val Gly Gln Leu
130                 135                 140
```

-continued

```
Tyr Glu Val Asp Asp Ile Ala Gln Leu Met Ile Trp Gly Ala Val Ser
145                 150                 155                 160

Thr Ala Phe Phe Val Val Met Asn Trp Ile Val Gly Thr Lys Ile Phe
                165                 170                 175

Lys Asn Arg Ala Thr Met Leu Gly Gly Thr Asp Ser Thr Ile Thr Lys
            180                 185                 190

Val Phe Trp Leu Met Met Phe Ala Trp Thr Leu Tyr Pro Ile Ala Tyr
        195                 200                 205

Leu Val Pro Ala Phe Met Asn Asn Ala Asp Gly Val Val Leu Arg Gln
210                 215                 220

Leu Leu Phe Thr Ile Ala Asp Ile Ser Ser Lys Val Ile Tyr Gly Leu
225                 230                 235                 240

Met Ile Thr Tyr Ile Ala Ile Gln Gln Ser Ala Ala Ala Gly Tyr Val
                245                 250                 255

Pro Ala Gln Gln Ala Leu Gly Arg Ile Gly Met Asp Ser Lys Ala Ala
            260                 265                 270

<210> SEQ ID NO 13
<211> LENGTH: 291
<212> TYPE: PRT
<213> ORGANISM: Proteomonas sulcata

<400> SEQUENCE: 13

Met Thr Thr Ile Ser Glu Val Cys Gly Val Trp Ala Leu Asp Asn Pro
1               5                   10                  15

Glu Cys Ile Glu Val Ser Gly Thr Asn Asp Asn Val Lys Met Ala Gln
            20                  25                  30

Leu Cys Phe Cys Met Val Cys Val Cys Gln Ile Leu Phe Met Ala Ser
        35                  40                  45

Gln Tyr Pro Lys Val Gly Trp Glu Ala Ile Tyr Leu Pro Ser Cys Glu
    50                  55                  60

Cys Phe Leu Tyr Gly Leu Ala Ser Ser Gly Asn Gly Phe Ile Gln Leu
65                  70                  75                  80

Tyr Asp Gly Arg Leu Ile Pro Trp Ala Arg Tyr Ala Ala Trp Ile Cys
                85                  90                  95

Thr Cys Pro Ser Ile Leu Leu Gln Ile Asn Thr Ile His Lys Cys Lys
            100                 105                 110

Ile Ser His Phe Asn Leu Asn Thr Phe Ile Val Gln Ala Asp Leu Ile
        115                 120                 125

Met Asn Ile Met Gly Val Thr Gly Ala Leu Thr Thr Asn Ile Ala Phe
130                 135                 140

Lys Trp Ile Tyr Phe Ala Ile Gly Cys Ile Leu Phe Ile Phe Ile Val
145                 150                 155                 160

Leu Val Val Tyr Asp Ile Met Thr Ser Ala Ala Lys Glu Trp Lys Ala
                165                 170                 175

Lys Gly Asp Ser Lys Gly Asn Leu Val Ser Thr Arg Leu Ile Leu Leu
            180                 185                 190

Arg Trp Ile Phe Ile Val Ser Trp Cys Val Tyr Pro Leu Leu Trp Ile
        195                 200                 205

Leu Ser Pro Gln Ala Thr Cys Ala Val Ser Glu Asp Val Ile Ser Val
210                 215                 220

Ala His Phe Ile Cys Asp Ala Phe Ala Lys Asn Met Phe Gly Phe Ile
225                 230                 235                 240

Met Trp Arg Thr Leu Trp Arg Asp Leu Asp Gly His Trp Asp Ile Ser
                245                 250                 255
```

```
Arg His Tyr Pro Gln Ser Ser Tyr Ala Lys Asp Gly Lys Glu Glu Glu
            260                 265                 270

Gln Met Thr Ala Met Ser Gln Thr Asp Asp Thr Glu Lys Pro His Ser
        275                 280                 285

Ser Gln Gly
    290

<210> SEQ ID NO 14
<211> LENGTH: 873
<212> TYPE: DNA
<213> ORGANISM: Artificial sequence
<220> FEATURE:
<223> OTHER INFORMATION: Synthetic nucleic acid

<400> SEQUENCE: 14
atgaccacca tcagcgaagt ctgcggcgtg tgggcactgg acaaccccga gtgtatcgaa      60
gtgtccggca ccaacgacaa cgtgaagatg gcccagctct gcttctgcat ggtgtgcgtc     120
tgccagatcc tgttcatggc cagccagtac cccaaagtcg gttgggaggc catctacctg     180
ccctcttgcg agtgcttcct gtacggactg gcctctagcg aaacggctt catccagctg      240 tacgacggca ggctgatccc ttgggctaga tacgccgctt ggatctgcac ctgtccctct     300
atcctgctgc agatcaacac catccacaag tgcaagatca gccacttcaa cctgaacacc     360
ttcatcgtgc aggccgacct gatcatgaac atcatgggcg tgacaggcgc cctgacaaca     420
aacatcgcct tcaagtggat ctacttcgcc atcggctgca tcctgttcat cttcatcgtg     480
ctggtggtgt acgacatcat gaccagcgcc gccaaggagt ggaaggctaa gggtgactcc     540
aagggcaacc tggtgtccac acggctgatc ctcctccgct ggatcttcat cgtcagttgg     600
tgcgtgtacc cactcctctg gattctgagc cctcaggcta cttgcgcagt gtccgaagac     660
gtgatcagcg tggcccactt catttgcgac gccttcgcca gaacatgtt cggcttcatc      720 atgtggcgca ccctctggag agatctggac ggccattggg acatcagcag acactacccc     780
cagagcagct acgctaagga cggcaaggag gaggagcaga tgacagccat gagccagacc     840
gacgataccg agaagcctca cagcagccag gga                                  873

<210> SEQ ID NO 15
<211> LENGTH: 873
<212> TYPE: DNA
<213> ORGANISM: Artificial sequence
<220> FEATURE:
<223> OTHER INFORMATION: Synthetic nucleic acid

<400> SEQUENCE: 15
atgaccacca tcagcgaggt gtgcggcgtg tgggcccgg acaaccccga gtgcatcgag       60
gtgagcggca ccaacgacaa cgtgaagatg gcccagctgt gcttctgcat ggtgtgcgtg     120
tgccagatcc tgttcatggc cagccagtac cccaaggtgg gctgggaggc catctacctg     180
cccagctgcg agtgcttcct gtacggcctg gccagcagcg gcaacggctt catccagctg     240
tacgacggcc gcctgatccc ctgggcccgc tacgccgcct ggatctgcac ctgccccagc     300
atcctgctgc agatcaacac catccacaag tgcaagatca gccacttcaa cctgaacacc     360
ttcatcgtgc aggccgacct gatcatgaac atcatgggcg tgaccggcgc cctgaccacc     420
aacatcgcct tcaagtggat ctacttcgcc atcggctgca tcctgttcat cttcatcgtg     480
ctggtggtgt acgacatcat gaccagcgcc gccaaggagt ggaaggccaa gggcgacagc     540
aagggcaacc tggtgagcac ccgcctgatc ctgctgcgct ggatcttcat cgtgagctgg     600
```

```
tgcgtgtacc ccctgctgtg gatcctgagc ccccaggcca cctgcgccgt gagcgaggac    660
gtgatcagcg tggcccactt catctgcgac gccttcgcca agaacatgtt cggcttcatc    720
atgtggcgca ccctgtggcg cgacctggac ggcactggg  acatcagccg ccactacccc    780
cagagcagct acgccaagga cggcaaggag gaggagcaga tgaccgccat gagccagacc    840
gacgacaccg agaagcccca cagcagccag ggc                                  873
```

<210> SEQ ID NO 16
<211> LENGTH: 885
<212> TYPE: DNA
<213> ORGANISM: Artificial sequence
<220> FEATURE:
<223> OTHER INFORMATION: Synthetic nucleic acid

<400> SEQUENCE: 16

```
atgagcagca tcacctgcga ccccgccatc tacggcgagt ggagccgcga gaaccagttc     60
tgcgtggaga gagcctgat  caccctggac ggcatcaagt acgtgcagct ggtgatggcc    120
gtggtgagcg cctgccaggt gttcttcatg gtgacccgcg cccccaaggt gccctgggag    180
gccatctacc tgcccaccac cgagatgatc acctacagcc tggccttcac cggcaacggc    240
tacatccgcg tggccaacgg caagtacctg ccctgggccc gcatggccag ctggctgtgc    300
acctgcccca tcatgctggg cctggtgagc aacatggccc tggtgaagta caagagcatc    360
cccctgaacc ccatgatgat cgccgccagc agcatctgca ccgtgttcgg catcaccgcc    420
agcgtggtgc tggacccccct gcacgtgtgg ctgtactgct tcatcagcag catcttcttc    480
atcttcgaga tggtggtggc cttcgccatc ttcgccatca ccatccacga cttccagacc    540
atcggcagcc ccatgagcct gaaggtggtg agcgcctga  agctgatgcg catcgtgttc    600
tacgtgagct ggatggccta ccccatcctg tggagcttca gcagcaccgg cgcctgcatc    660
atgagcgaga acaccagcag cgtgctgtac ctgctgggcg acgccctgtg caagaacacc    720
tacggcatcc tgctgtgggc caccacctgg ggcctgctga acggcaagtg ggaccgcgac    780
tacgtgaagg gccgcaacgt ggacggcacc ctgatgcccg agtacgagca ggacctggag    840
aagggcaaca ccgagcgcta cgaggacgcc cgcgccggcg agacc                     885
```

<210> SEQ ID NO 17
<211> LENGTH: 873
<212> TYPE: DNA
<213> ORGANISM: Artificial sequence
<220> FEATURE:
<223> OTHER INFORMATION: Synthetic nucleic acid

<400> SEQUENCE: 17

```
atggccagcc aggtggtgta cggcgagtgg gccagcaccc acaccgagtg ctacaacatg     60
agccgcatcg acagcacctt cgtgagcctg ctgcagctgg tgtgggccgt ggtgagcggc    120
tgccagacca tcttcatgat cagccgcgcc cccaaggtgc cctgggagag cgtgtacctg    180
cccttcgtgg agagcatcac ctacgccctg ccagcaccg  gcaacggcac cctgcagatg    240
cgcgacggcc gcttcttccc ctggagccgc atggccagct ggctgtgcac ctgccccatc    300
atgctgggcc agatcagcaa catggccctg gtgaagtaca agagcatccc cctgaacccc    360
atcgcccagg ccgccagcat catccgcgtg gtgatgggca tcaccgccac catcagcccc    420
gccgagtaca tgaagtggct gttcttcttc ttcggcgcca cctgcctggt gttcgagtac    480
agcgtggtgt tcaccatctt ccaggtgggc ctgtacggct tcgagagcgt gggcaccccc    540
```

```
ctggcccaga aggtggtggt gcgcatcaag atgctgcgcc tgatcttctt catcgcctgg      600
accatgttcc ccatcgtgtg gctgatcagc cccaccggcg tgtgcgtgat ccacgagaac      660
gtgagcgcca tcctgtacct gctggccgac ggcctgtgca agaacaccta cggcgtgatc      720
ctgtggagca ccgcctgggg cgtgctggag ggcaagtggg accccgcctg cctgcccggc      780
caggagaagc ccgaggccga cgacccttc ggcctgaacc acgagaagaa cgcccccccc      840
aacgacgagg tgaacatccg catgttcggc cgc                                  873
```

<210> SEQ ID NO 18
<211> LENGTH: 864
<212> TYPE: DNA
<213> ORGANISM: Artificial sequence
<220> FEATURE:
<223> OTHER INFORMATION: Synthetic nucleic acid

<400> SEQUENCE: 18

```
atgagcgtgg tgtacggcga gtgggccgcc cagaacccca gctgcgtgac cctgagcaac       60
atcgacctgg gcgtgcgcac cttcgagctg tgctggggca tcatgtgcgc ctgccaggcc      120
gtgttcttcg ccctgcgcta ccccgcggc acctgggagt tcgtgctggt gcccctgacc       180
gagtgcttcg tgtacggcct gggctacagc gagatcggct acatcctgct gtgggacggc      240
cgccaggtgc tgtggacccg caccgtgctg tggctggcca ccgtgcccat catcctgaac      300
cagatcaacg gcatggccgc cgtgcgcatc tacggcgtgg acctgaacgt gatgcagatg      360
tacttcagca ccctgatgat ctgcttcggc cacaccgccg ccctgaccca aaccagagc      420 ctgaagtggc tgttcttcat catcgccatg gccatcttcg gcctgatctg cttcatcaac      480
taccacacct tcaccgccgc cgagaagcac tacaaggaga gcggcagcga gatcgacctg      540
atcatcgcca agcgcatccg cctgctggcc gtgatcttct tcaccagctg gaccatgtac      600
cccctgttct tcgtgctgag cgtggagggc gcctgcgtgg ccagcgagag cgtgatcctg      660
gtgtgcttcg ccctggccga cctgctgagc aagaacgtgt cggcgtgct gttctgggac      720 accctgtgga acctgcagga cggcaagtgg agcagctacg gcaccgtgac cttcttcaag      780
accaccgaca cgtgaccaa gaccgccatc agcaccgcca tggaggagga gttcgccaag      840
cagaaggcca ccgcagcga caac                                             864
```

<210> SEQ ID NO 19
<211> LENGTH: 2136
<212> TYPE: DNA
<213> ORGANISM: Artificial sequence
<220> FEATURE:
<223> OTHER INFORMATION: Synthetic nucleic acid

<400> SEQUENCE: 19

```
atgagccgcc gccctggct gctggccctg gccctggccg tggccctggc cgccggcagc       60
gccggcgcca gcaccggcag cgacgccacc gtgcccgtgg ccacccagga cggccccgac      120
tacgtgttcc accgcgccca cgagcgcatg ctgttccaga ccagctacac cctggagaac      180
aacggcagcg tgatctgcat ccccaacaac ggccagtgct ctgcctggc ctggctgaag      240 agcaacggca ccaacgccga gaagctggcc gccaacatcc tgcagtggat caccttcgcc      300
ctgagcgccc tgtgcctgat gttctacggc taccagacct ggaagagcac ctgcggctgg      360
gaggagatct acgtggccac catcgagatg atcaagttca tcgagta cttccacgag      420 ttcgacgagc ccgccgtgat ctacagcagc aacggcaaca agaccgtgtg gctgcgctac      480
gccgagtggc tgctgaccct ccccgtgatc ctgatccacc tgagcaacct gaccggcctg      540
```

| | |
|---|---|
| gccaacgact acaacaagcg caccatgggc ctgctggtga gcgacatcgg caccatcgtg | 600 |
| tggggcacca ccgccgccct gagcaagggc tacgtgcgcg tgatcttctt cctgatgggc | 660 |
| ctgtgctacg gcatctacac cttcttcaac gccgccaagg tgtacatcga ggcctaccac | 720 |
| accgtgccca agggcatctg ccgcgacctg gtgcgctacc tggcctggct gtacttctgc | 780 |
| agctgggcca tgttccccgt gctgttcctg ctgggccccg agggcttcgg ccacatcaac | 840 |
| cagttcaaca cgccatcgc ccacgccatc ctggacctgg ccagcaagaa cgcctggagc | 900 |
| atgatgggcc acttcctgcg cgtgaagatc cacgagcaca tcctgctgta cggcgacatc | 960 |
| cgcaagaagc agaaggtgaa cgtggccggc caggagatgg aggtggagac catggtgcac | 1020 |
| gaggaggacg acgagaccca gaaggtgccc accgccaagt acgccaaccg cgacagcttc | 1080 |
| atcatcatgc gcgaccgcct gaaggagaag ggcttcgaga cccgcgccag cctggacggc | 1140 |
| gaccccaacg cgacgccga ggccaacgcc gccgccggcg gcaagcccgg catggagatg | 1200 |
| ggcaagatga ccggcatggg catgagcatg ggcgccggca tgggcatggc caacatcgac | 1260 |
| agcggccgcg tgatcctggc cgtgcccgac atcagcatgg tggacttctt ccgcgagcag | 1320 |
| ttcgcccgcc tgcccgtgcc ctacgagctg gtgcccgccc tgggcgccga gaacaccctg | 1380 |
| cagctggtgc agcaggccca gagcctgggc ggctgcgact tcgtgctgat gcaccccgag | 1440 |
| ttcctgcgcg accgcagccc caccggcctg ctgccccgcc tgaagatggg cggccagcgc | 1500 |
| gccgccgcct tcggctgggc cgccatcggc ccatgcgcg acctgatcga gggcagcggc | 1560 |
| gtggacggct ggctggaggg ccccagcttc ggcgccggca tcaaccagca ggccctggtg | 1620 |
| gccctgatca accgcatgca gcaggccaag aagatgggca tgatgggcgg catgggcatg | 1680 |
| ggcatgggcg gcggcatggg catgggcatg gcatgggca tgggcatggc ccccagcatg | 1740 |
| aacgccggca tgaccggcgg catgggcggc gccagcatgg gcggcgccgt gatgggcatg | 1800 |
| ggcatgggca tgcagcccat gcagcaggcc atgcccgcca tgagcccat gatgacccag | 1860 |
| cagcccagca tgatgagcca gcccagcgcc atgagcgccg gcggcgccat gcaggccatg | 1920 |
| ggcggcgtga tgcccagccc cgccccggc ggccgcgtgg gcaccaaccc cctgttcggc | 1980 |
| agcgcccca gccccctgag cagccagccc ggcatcagcc ccggcatggc cacccccccc | 2040 |
| gccgccaccg ccgcccccgc cgccggcggc agcgaggccg agatgctgca gcagctgatg | 2100 |
| agcgagatca accgcctgaa gaacgagctg ggcgag | 2136 |

<210> SEQ ID NO 20
<211> LENGTH: 2211
<212> TYPE: DNA
<213> ORGANISM: Artificial sequence
<220> FEATURE:
<223> OTHER INFORMATION: Synthetic nucleic acid

<400> SEQUENCE: 20

| | |
|---|---|
| atggactacg gcggcgccct gagcgccgtg ggccgcgagc tgctgttcgt gaccaacccc | 60 |
| gtggtggtga acgcagcgt gctggtgccc gaggaccagt gctactgcgc cggctggatc | 120 |
| gagagccgcg gcaccaacgg cgcccagacc gccagcaacg tgctgcagtg gctggccgcc | 180 |
| ggcttcagca tcctgctgct gatgttctac gcctaccaga cctggaagag cacctgcggc | 240 |
| tgggaggaga tctacgtgtg cgccatcgag atggtgaagg tgatcctgga gttcttcttc | 300 |
| gagttcaaga ccccagcat gctgtacctg gccaccggcc accgcgtgca gtggctgcgc | 360 |
| tacgccgagt ggctgctgac ctgccccgtg atcctgatcc acctgagcaa cctgaccggc | 420 |

```
ctgagcaacg actacagccg ccgcaccatg ggcctgctgg tgagcgacat cggcaccatc    480
gtgtggggcg ccaccagcgc catggccacc ggctacgtga aggtgatctt cttctgcctg    540
ggcctgtgct acggcgccaa caccttcttc cacgccgcca aggcctacat cgagggctac    600
cacaccgtgc ccaagggccg ctgccgccag gtggtgaccg gcatggcctg gctgttcttc    660
gtgagctggg gcatgttccc catcctgttc atcctgggcc ccgagggctt cggcgtgctg    720
agcgtgtacg gcagcaccgt gggccacacc atcatcgacc tgatgagcaa gaactgctgg    780
ggcctgctgg gccactacct gcgcgtgctg atccacgagc acatcctgat ccacggcgac    840
atccgcaaga ccaccaagct gaacatcggc ggcaccgaga tcgaggtgga ccctggtg     900 gaggacgagg ccgaggccgg cgccgtgaac aagggcaccg gcaagtacgc cagccgcgag    960
agcttcctgg tgatgcgcga caagatgaag gagaagggca tcgacgtgcg cgccagcctg   1020
gacaacagca aggaggtgga gcaggagcag gccgcccgcg ccgccatgat gatgatgaac   1080
ggcaacggca tgggcatggg catgggcatg aacggcatga acggcatggg cggcatgaac   1140
ggcatggccg gcggcgccaa gcccggcctg gagctgaccc ccagctgca gcccggccgc    1200 gtgatcctgg ccgtgcccga catcagcatg gtggacttct ccgcgagca gttcgcccag   1260 ctgagcgtga cctacgagct ggtgcccgcc ctgggcgccg acaacaccct ggccctggtg   1320
acccaggccc agaacctggg cggcgtggac ttcgtgctga ccaccccga gttcctgcgc   1380 gaccgcagca gcaccagcat cctgagccgc ctgcgcggcg ccggccagcg cgtggccgcc   1440
ttcggctggg cccagctggg ccccatgcgc gacctgatcg agagcgccaa cctggacggc   1500
tggctggagg gccccagctt cggccagggc atcctgcccg cccacatcgt ggccctggtg   1560
gccaagatgc agcagatgcg caagatgcag cagatgcagc agatcggcat gatgaccggc   1620
ggcatgaacg gcatgggcgg cggcatgggc ggcggcatga acggcatggg cggcggcaac   1680
ggcatgaaca acatgggcaa cggcatgggc ggcggcatgg gcaacggcat gggcggcaac   1740
ggcatgaacg gcatgggcgg cggcaacggc atgaacaaca tgggcggcaa cggcatggcc   1800
ggcaacggca tgggcggcgg catgggcggc aacggcatgg gcggcagcat gaacggcatg   1860
agcagcggcg tggtggccaa cgtgaccccc agccgccg gcggcatggg cggcatgatg    1920
aacggcggca tggccgcccc ccagagcccc ggcatgaacg gcggccgcct gggcaccaac   1980
cccctgttca acgccgcccc cagcccctg agcagccagc tgggcgccga ggccggcatg   2040
ggcagcatgg gcggcatggg cggcatgagc ggcatgggcg gcatgggcgg catgggcggc   2100
atgggcggcg ccggcgccgc caccacccag ccgccggcg gcaacgccga ggccgagatg   2160
ctgcagaacc tgatgaacga gatcaaccgc ctgaagcgcg agctgggcga g           2211
```

<210> SEQ ID NO 21
<211> LENGTH: 1056
<212> TYPE: DNA
<213> ORGANISM: Artificial sequence
<220> FEATURE:
<223> OTHER INFORMATION: Synthetic nucleic acid

<400> SEQUENCE: 21

```
atggacaccc tggcctgggt ggcccgcgag ctgctgagca ccgccacga cgccacccc      60 gccaccgcca cccccagcac cgaccacagc acccccagca ccgaccacgg cagcggcgag    120
accttcaacg tgaccatcac catcggcggc ggccaccacg gcggccacgc cggccccgtg    180
gacaacagca tcgtgatcgg cggcatcgac ggctggatcc catcccgc cggcgactgc     240 tactgcgccg gctggtacgt gagccacggc agcagcttcg aggccacctt cgcccacgtg    300
```

```
tgccagtgga gcatcttcgc cgtgtgcatc ctgagcctgc tgtggtacgc ctggcagtac    360
tggaaggcca cctgcggctg ggaggaggtg tacgtgtgct gcatcgagct ggtgttcatc    420
tgcttcgagc tgtaccacga gttcgacagc ccctgcagcc tgtacctgag caccgccaac    480
atcgtgaact ggctgcgcta cagcgagtgg ctgctgtgct gccccgtgat cctgatccac    540
ctgagcaacg tgaccggcct gagcgacgac tacggccgcc gcaccatggg cctgctggtg    600
agcgacatcg ccaccatcgt gttcggcatc accgccgcca tgctggtgag ctggcccaag    660
atcatcttct acctgctggg cttcaccatg tgctgctaca ccttctacct ggccgccaag    720
gtgctgatcg agagcttcca ccaggtgccc aagggcatct gccgccacct ggtgaaggcc    780
atggccatca cctactacgt gggctggagc ttcttccccc tgatcttcct gttcggccag    840
agcggcttca gaagatcag cccctacgcc gacgtgatcg ccagcagctt cggcgacctg    900
atcagcaaga acatgttcgg cctgctgggc cacttcctgc gcgtgaagat ccacgagcac    960
atcctgaagc acgccgacat ccgcaagacc acccacctgc gcatcgccgg cgaggagaag   1020
gaggtggaga ccttcgtgga ggaggaggac gaggac                             1056
```

<210> SEQ ID NO 22
<211> LENGTH: 1779
<212> TYPE: DNA
<213> ORGANISM: Artificial sequence
<220> FEATURE:
<223> OTHER INFORMATION: Synthetic nucleic acid

<400> SEQUENCE: 22

```
atgagccccc ccaccagccc caccccccgac accggccacg acaccccccga caccggccac     60 gacaccggcg ccacggcgc cgtggagatc tgcttcgccc cctgcaggga ggactgcgtg    120
accatccgct acttcgtgga gaacgacttc gagggctgca tccccggcca cttcgaccag    180
tacagcagcc acggcagcct gcacgacatc gtgaaggccg ccctgtacat ctgcatggtg    240
atcagcatcc tgcagatcct gttctacggc ttccagtggt ggcgcaagac ctgcggctgg    300
gaggtgtggt tcgtggcctg catcgagacc agcatctaca tcatcgccat caccagcgag    360
gccgacagcc ccttcaccct gtacctgacc aacggccaga tcagccccca gctgcgctac    420
atggagtggc tgatgacctg ccccgtgatc ctgatcgccc tgagcaacat caccggcatg    480
gccgaggagt acaacaagcg caccatgacc ctgctgacca cgacgtgtg ctgcatcgtg    540 ctgggcatga tgagcgccgc cagcaagccc cgcctgaagg gcatcctgta cgccgtgggc    600
tgggccttcg cgcctggac ctactggacc gccctgcagg tgtaccgcga cgcccacaag    660
gccgtgccca gcccctggc ctggtacgtg cgcgccatgg gctacgtgtt cttccaccagc    720 tggctgacct cccccggctg gttcctgctg ggccccgagg gctggaggt ggtgaccggc    780 accgtgagca ccctgatgca cgcctgcagc gacctgatca gcaagaacct gtggggcttc    840
atggactggc acctgcgcgt gctggtggcc gccaccacc gcaagctgtt caaggccgag    900
gaggagcacg ccctgaagaa gggccagacc ctggagcccg gcatgccccg cagcaccagc    960
ttcgtgcgcg gcctgggcga cgacgtggag atcgacccca gctacgagct gtaccgcctg   1020
aagcgccaga accaccccga gtacttcctg agccccgccc agacccccg ccgcggcccc   1080 agcttcgaca gcgcaccag cttcgagatg gacggcggca agaacggcat gctgcagatg   1140
atgcccgtga ccggcatggg catgggcatg gcatgggca tgggcggcgg caagaccgtg   1200
ctgttcctgg actacaccgg cggcggctac gtgagcttct cgagcagca gctgagcaac   1260
```

```
atgggcgtga acgtgaccaa gtgctggagc gacgacgaca tgtacaacac cgccggcgtg    1320
gccaacgtga agcagctgtt ccacttcgcc atgatcccca acaacgccct gggcggccag    1380
atggtgatgg acctgcgcgg caccggcctg ctggtggtgg cctacggccc cgagcccccc    1440
atgcccggca tgggccagga cgagttcgtg cccctgcaga tgcccggcgt gcccctacgac    1500 gagagcatcc tgcacaacct ggtgatgcgc cacgccatca cccagggcct gggcatgaac    1560
ggcatgcagg gcaacatggg ccagcagcag cagatgatgg gcatgcaggg caacatgaac    1620
ggcatgcagg gcaacatgaa cggcatgcag gcaacatga acggcatgca gggcaacatg    1680
agcggcatgc agggcaacat gaacggcatg cagggcaaca gcggcatgaa ccagggctgg    1740
aacaaccagg gcttcaccaa caccggcgcc ttcggctac                           1779

<210> SEQ ID NO 23
<211> LENGTH: 822
<212> TYPE: DNA
<213> ORGANISM: Artificial sequence
<220> FEATURE:
<223> OTHER INFORMATION: Synthetic nucleic acid

<400> SEQUENCE: 23
atgagcatca ccagcgtgcc cggcgtggtg gacgccggcg tgctgggcgc ccagagcgcc      60
gccgccgtgc gcgagaacgc cctgctgagc agcagcctgt gggtgaacgt ggccctggcc     120
ggcatcgcca tcctggtgtt cgtgtacatg ggccgcacca tccgcccccgg ccgccccgc     180 ctgatctggg gcgccaccct gatgatcccc ctggtgagca tcagcagcta cctgggcctg     240
ctgagcggcc tgaccgtggg catgatcgag atgcccgccg ccacgccct ggccggcgag      300 atggtgcgca gccagtgggg ccgctacctg acctgggccc tgagcacccc catgatcctg     360
ctggccctgg gcctgctggc cgacgtggac ctgggcagcc tgttcaccgt gatcgccgcc     420
gacatcggca tgtgcgtgac cggcctggcc gccgccatga ccaccagcgc cctgctgttc     480
cgctgggcct tctacgccat cagctgcgcc ttcttcgtgg tggtgctgag cgccctggtg     540
accgactggg ccgccagcgc cagcagcgcc ggcaccgccg agatcttcga caccctgcgc     600
gtgctgaccg tggtgctgtg gctgggctac cccatcgtgt gggccgtggg cgtggagggc     660
ctggccctgg tgcagagcgt gggcgtgacc agctgggcct acagcgtgct ggacgtgttc     720
gccaagtacg tgttcgcctt catcctgctg cgctgggtgg ccaacaacga gcgcaccgtg     780
gccgtggccg ccagaccct gggcaccatg agcagcgacg ac                         822

<210> SEQ ID NO 24
<211> LENGTH: 816
<212> TYPE: DNA
<213> ORGANISM: Artificial sequence
<220> FEATURE:
<223> OTHER INFORMATION: Synthetic nucleic acid

<400> SEQUENCE: 24
atgaagaaca tcgagagcct gttcgactac agcgccggcc agttcgagtt catcgaccac      60
ctgctgacca tgggcgtggg cgtgcacttc gccgccctga tcttcttcct ggtggtgagc     120
cagttcgtgg cccccaagta ccgcatcgcc accgccctga gctgcatcgt gatggtgagc     180
gccggcctga tcctgaacag ccaggccgtg atgtggaccg acgcctacgc ctacgtggac     240
ggcagctacc agctgcagga cctgaccttc agcaacggct accgctacgt gaactggatg     300
gccaccatcc cctgcctgct gctgcagctg ctgatcgtgc tgaacctgaa gggcaaggag     360
ctgttcagca ccgccacctg gctgatcctg gccgcctggg gcatgatcat caccggctac     420
```

```
gtgggccagc tgtacgaggt ggacgacatc gcccagctga tgatctgggg cgccgtgagc    480
accgccttct tcgtggtgat gaactggatc gtgggcacca agatcttcaa gaaccgcgcc    540
accatgctgg gcggcaccga cagcaccatc accaaggtgt tctggctgat gatgttcgcc    600
tggaccctgt accccatcgc ctacctggtg cccgccttca tgaacaacgc cgacggcgtg    660
gtgctgcgcc agctgctgtt caccatcgcc gacatcagca gcaaggtgat ctacggcctg    720
atgatcacct acatcgccat ccagcagagc cgccgccgcg gctacgtgcc cgcccagcag    780
gccctgggcc gcatcggcat ggacagcaag gccgcc                              816
```

```
<210> SEQ ID NO 25
<211> LENGTH: 13
<212> TYPE: PRT
<213> ORGANISM: Artificial sequence
<220> FEATURE:
<223> OTHER INFORMATION: Synthetic peptide

<400> SEQUENCE: 25

Gly Arg Lys Lys Arg Arg Gln Arg Arg Arg Pro Pro Gln
1               5                   10

<210> SEQ ID NO 26
<211> LENGTH: 16
<212> TYPE: PRT
<213> ORGANISM: Artificial sequence
<220> FEATURE:
<223> OTHER INFORMATION: Synthetic peptide

<400> SEQUENCE: 26

Arg Gln Ile Lys Ile Trp Phe Gln Asn Arg Arg Met Lys Trp Lys Lys
1               5                   10                  15

<210> SEQ ID NO 27
<211> LENGTH: 26
<212> TYPE: PRT
<213> ORGANISM: Artificial sequence
<220> FEATURE:
<223> OTHER INFORMATION: Synthetic peptide

<400> SEQUENCE: 27

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 28
<211> LENGTH: 10
<212> TYPE: PRT
<213> ORGANISM: Artificial sequence
<220> FEATURE:
<223> OTHER INFORMATION: Synthetic peptide

<400> SEQUENCE: 28

Thr Lys Ile Glu Ser Leu Lys Glu His Gly
1               5                   10

<210> SEQ ID NO 29
<211> LENGTH: 10
<212> TYPE: PRT
<213> ORGANISM: Artificial sequence
<220> FEATURE:
<223> OTHER INFORMATION: Synthetic peptide

<400> SEQUENCE: 29
```

Thr Gln Ile Glu Asn Leu Lys Glu Lys Gly
1               5                   10

<210> SEQ ID NO 30
<211> LENGTH: 26
<212> TYPE: PRT
<213> ORGANISM: Artificial sequence
<220> FEATURE:
<223> OTHER INFORMATION: Synthetic peptide

<400> SEQUENCE: 30

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala
            20                  25

<210> SEQ ID NO 31
<211> LENGTH: 25
<212> TYPE: PRT
<213> ORGANISM: Artificial sequence
<220> FEATURE:
<223> OTHER INFORMATION: Synthetic peptide

<400> SEQUENCE: 31

Gly Leu Phe Glu Ala Ile Glu Gly Phe Ile Glu Asn Gly Trp Glu Gly
1               5                   10                  15

Met Ile Glu Gly Trp Tyr Gly Cys Gly
            20                  25

<210> SEQ ID NO 32
<211> LENGTH: 16
<212> TYPE: PRT
<213> ORGANISM: Artificial sequence
<220> FEATURE:
<223> OTHER INFORMATION: Synthetic peptide

<400> SEQUENCE: 32

Trp Glu Ala Ile Tyr Leu Pro Thr Thr Glu Met Ile Thr Tyr Ser Leu
1               5                   10                  15

<210> SEQ ID NO 33
<211> LENGTH: 16
<212> TYPE: PRT
<213> ORGANISM: Artificial sequence
<220> FEATURE:
<223> OTHER INFORMATION: Synthetic peptide

<400> SEQUENCE: 33

Trp Glu Ser Val Tyr Leu Pro Phe Val Glu Ser Ile Thr Tyr Ala Leu
1               5                   10                  15

<210> SEQ ID NO 34
<211> LENGTH: 16
<212> TYPE: PRT
<213> ORGANISM: Artificial sequence
<220> FEATURE:
<223> OTHER INFORMATION: Synthetic peptide

<400> SEQUENCE: 34

Trp Glu Phe Val Leu Val Pro Leu Thr Glu Cys Phe Val Tyr Gly Leu
1               5                   10                  15

<210> SEQ ID NO 35
<211> LENGTH: 20
<212> TYPE: PRT

```
<213> ORGANISM: Artificial sequence
<220> FEATURE:
<223> OTHER INFORMATION: Synthetic peptide

<400> SEQUENCE: 35

Trp Glu Glu Ile Tyr Val Ala Thr Ile Glu Met Ile Lys Phe Ile Ile
1               5                   10                  15

Glu Tyr Phe His
            20

<210> SEQ ID NO 36
<211> LENGTH: 20
<212> TYPE: PRT
<213> ORGANISM: Artificial sequence
<220> FEATURE:
<223> OTHER INFORMATION: Synthetic peptide

<400> SEQUENCE: 36

Trp Glu Glu Ile Tyr Val Cys Ala Ile Glu Met Val Lys Val Ile Leu
1               5                   10                  15

Glu Phe Phe Phe
            20

<210> SEQ ID NO 37
<211> LENGTH: 20
<212> TYPE: PRT
<213> ORGANISM: Artificial sequence
<220> FEATURE:
<223> OTHER INFORMATION: Synthetic peptide

<400> SEQUENCE: 37

Trp Glu Glu Val Tyr Val Cys Cys Ile Glu Leu Val Phe Ile Cys Phe
1               5                   10                  15

Glu Leu Tyr His
            20

<210> SEQ ID NO 38
<211> LENGTH: 20
<212> TYPE: PRT
<213> ORGANISM: Artificial sequence
<220> FEATURE:
<223> OTHER INFORMATION: Synthetic peptide

<400> SEQUENCE: 38

Trp Glu Val Trp Phe Val Ala Cys Ile Glu Thr Ser Ile Tyr Ile Ile
1               5                   10                  15

Ala Ile Thr Ser
            20

<210> SEQ ID NO 39
<211> LENGTH: 20
<212> TYPE: PRT
<213> ORGANISM: Artificial sequence
<220> FEATURE:
<223> OTHER INFORMATION: Synthetic peptide

<400> SEQUENCE: 39

Arg Pro Arg Leu Ile Trp Gly Ala Thr Leu Met Ile Pro Leu Val Ser
1               5                   10                  15

Ile Ser Ser Tyr
            20

<210> SEQ ID NO 40
<211> LENGTH: 20
```

```
<212> TYPE: PRT
<213> ORGANISM: Artificial sequence
<220> FEATURE:
<223> OTHER INFORMATION: Synthetic peptide

<400> SEQUENCE: 40

Ala Leu Ser Cys Ile Val Met Val Ser Ala Gly Leu Ile Leu Asn Ser
1               5                   10                  15

Gln Ala Val Met
            20

<210> SEQ ID NO 41
<211> LENGTH: 21
<212> TYPE: PRT
<213> ORGANISM: Artificial sequence
<220> FEATURE:
<223> OTHER INFORMATION: Synthetic peptide

<400> SEQUENCE: 41

Ala Arg Met Ala Ser Trp Leu Cys Thr Cys Pro Ile Met Leu Gly Leu
1               5                   10                  15

Val Ser Asn Met Ala
            20

<210> SEQ ID NO 42
<211> LENGTH: 21
<212> TYPE: PRT
<213> ORGANISM: Artificial sequence
<220> FEATURE:
<223> OTHER INFORMATION: Synthetic peptide

<400> SEQUENCE: 42

Ser Arg Met Ala Ser Trp Leu Cys Thr Cys Pro Ile Met Leu Gly Gln
1               5                   10                  15

Ile Ser Asn Met Ala
            20

<210> SEQ ID NO 43
<211> LENGTH: 21
<212> TYPE: PRT
<213> ORGANISM: Artificial sequence
<220> FEATURE:
<223> OTHER INFORMATION: Synthetic peptide

<400> SEQUENCE: 43

Thr Arg Thr Val Leu Trp Leu Ala Thr Val Pro Ile Ile Leu Asn Gln
1               5                   10                  15

Ile Asn Gly Met Ala
            20

<210> SEQ ID NO 44
<211> LENGTH: 21
<212> TYPE: PRT
<213> ORGANISM: Artificial sequence
<220> FEATURE:
<223> OTHER INFORMATION: Synthetic peptide

<400> SEQUENCE: 44

Leu Arg Tyr Ala Glu Trp Leu Leu Thr Cys Pro Val Ile Leu Ile His
1               5                   10                  15

Leu Ser Asn Leu Thr
            20

<210> SEQ ID NO 45
```

```
<211> LENGTH: 21
<212> TYPE: PRT
<213> ORGANISM: Artificial sequence
<220> FEATURE:
<223> OTHER INFORMATION: Synthetic peptide

<400> SEQUENCE: 45

Leu Arg Tyr Ala Glu Trp Leu Leu Thr Cys Pro Val Ile Leu Ile His
1               5                   10                  15

Leu Ser Asn Leu Thr
            20

<210> SEQ ID NO 46
<211> LENGTH: 21
<212> TYPE: PRT
<213> ORGANISM: Artificial sequence
<220> FEATURE:
<223> OTHER INFORMATION: Synthetic peptide

<400> SEQUENCE: 46

Leu Arg Tyr Ser Glu Trp Leu Leu Cys Cys Pro Val Ile Leu Ile His
1               5                   10                  15

Leu Ser Asn Val Thr
            20

<210> SEQ ID NO 47
<211> LENGTH: 21
<212> TYPE: PRT
<213> ORGANISM: Artificial sequence
<220> FEATURE:
<223> OTHER INFORMATION: Synthetic peptide

<400> SEQUENCE: 47

Leu Arg Tyr Met Glu Trp Leu Met Thr Cys Pro Val Ile Leu Ile Ala
1               5                   10                  15

Leu Ser Asn Ile Thr
            20

<210> SEQ ID NO 48
<211> LENGTH: 21
<212> TYPE: PRT
<213> ORGANISM: Artificial sequence
<220> FEATURE:
<223> OTHER INFORMATION: Synthetic peptide

<400> SEQUENCE: 48

Gly Arg Tyr Leu Thr Trp Ala Leu Ser Thr Pro Met Ile Leu Leu Ala
1               5                   10                  15

Leu Gly Leu Ile Ala
            20

<210> SEQ ID NO 49
<211> LENGTH: 21
<212> TYPE: PRT
<213> ORGANISM: Artificial sequence
<220> FEATURE:
<223> OTHER INFORMATION: Synthetic peptide

<400> SEQUENCE: 49

Tyr Arg Tyr Val Asn Trp Met Ala Thr Ile Pro Cys Leu Leu Leu Gln
1               5                   10                  15

Leu Leu Ile Val Leu
            20
```

<210> SEQ ID NO 50
<211> LENGTH: 345
<212> TYPE: PRT
<213> ORGANISM: Chlamydomonas reinhardtii

<400> SEQUENCE: 50

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
            260                 265                 270

Pro Glu Gly Phe Gly His Ile Asn Gln Phe Asn Ser Ala Ile Ala His
        275                 280                 285

Ala Ile Leu Asp Leu Ala Ser Lys Asn Ala Trp Ser Met Met Gly His
    290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
                325                 330                 335

Thr Met Val His Glu Glu Asp Asp Glu
            340                 345

<210> SEQ ID NO 51
<211> LENGTH: 315
<212> TYPE: PRT
<213> ORGANISM: Chlamydomonas reinhardtii

```
<400> SEQUENCE: 51

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
        130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
        290                 295                 300

Glu Ala Gly Ala Val Asn Lys Gly Thr Gly Lys
305                 310                 315
```